United States Patent
Chen et al.

(10) Patent No.: US 11,623,012 B2
(45) Date of Patent: Apr. 11, 2023

(54) BICYCLIC PEPTIDE LIGANDS SPECIFIC FOR EPHA2

(71) Applicant: BicycleRD Limited, Cambridge (GB)

(72) Inventors: Liuhong Chen, Cambridge (GB); Silvia Pavan, Cambridge (GB); Catherine Stace, Cambridge (GB); Daniel Teufel, Cambridge (GB); Katerine Van Rietschoten, Cambridge (GB)

(73) Assignee: BicycleRD Limited, Cambridge (GB)

( * ) Notice: Subject to any disclaimer, the term of this patent is extended or adjusted under 35 U.S.C. 154(b) by 0 days.

(21) Appl. No.: 16/771,142

(22) PCT Filed: Dec. 19, 2018

(86) PCT No.: PCT/GB2018/053676
§ 371 (c)(1),
(2) Date: Jun. 9, 2020

(87) PCT Pub. No.: WO2019/122861
PCT Pub. Date: Jun. 27, 2019

(65) Prior Publication Data
US 2020/0338203 A1      Oct. 29, 2020

(30) Foreign Application Priority Data

Dec. 19, 2017   (GB) ..................................... 1721265

(51) Int. Cl.
*C07K 7/64*       (2006.01)
*A61K 47/64*      (2017.01)

(52) U.S. Cl.
CPC ............ *A61K 47/6415* (2017.08); *C07K 7/64* (2013.01)

(58) Field of Classification Search
CPC ....... A61K 47/6415; A61K 47/64; C07K 7/64
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 6,326,144 B1 | 12/2001 | Bawendi et al. |
| 6,468,808 B1 | 10/2002 | Nie et al. |
| 7,151,047 B2 | 12/2006 | Chan et al. |
| 7,192,785 B2 | 3/2007 | Nie et al. |
| 8,138,347 B2 | 3/2012 | Knight et al. |
| 8,680,022 B2 | 3/2014 | Gregory et al. |
| 8,685,890 B2 * | 4/2014 | Winter ............... C12N 15/1044 506/9 |
| 8,778,844 B2 | 7/2014 | Winter et al. |
| 9,518,081 B2 | 12/2016 | Winter et al. |
| 9,644,201 B2 | 5/2017 | Winter et al. |
| 9,657,288 B2 | 5/2017 | Winter et al. |
| 9,670,482 B2 | 6/2017 | Winter et al. |
| 9,670,484 B2 | 6/2017 | Winter et al. |
| 9,868,767 B2 | 1/2018 | Pei et al. |
| 9,932,367 B2 | 4/2018 | Stace et al. |
| 9,994,617 B2 | 6/2018 | Tite et al. |
| 10,118,947 B2 | 11/2018 | Teufel et al. |
| 10,294,274 B2 | 5/2019 | Teufel et al. |
| 10,441,663 B2 | 10/2019 | Bennett et al. |
| 10,532,106 B2 | 1/2020 | Teufel et al. |
| 10,624,968 B2 | 4/2020 | Bennett et al. |
| 10,800,813 B2 | 10/2020 | Tite et al. |
| 10,919,937 B2 | 2/2021 | Beswick et al. |
| 11,306,123 B2 | 4/2022 | Mudd et al. |
| 11,312,749 B2 | 4/2022 | Mudd et al. |
| 11,332,500 B2 | 5/2022 | Mudd et al. |
| 2002/0164788 A1 | 11/2002 | Ellis et al. |
| 2017/0067045 A1 | 3/2017 | Winter et al. |
| 2017/0190743 A1 | 7/2017 | Pei et al. |

(Continued)

FOREIGN PATENT DOCUMENTS

| | | |
|---|---|---|
| WO | 2001042246 A2 | 6/2001 |
| WO | 2002088112 A1 | 11/2002 |

(Continued)

OTHER PUBLICATIONS

Deyle etal (Accounts of Chemical Research, 2017, 50, 1866-1874) (Year: 2017).*
Heinis etal (Nature Chemical Biology, 2009, vol. 5, No. 7, 502-507). (Year: 2009).*
Annunziata et al., "Phase 1, open-label study of MEDI-547 in patients with relapsed or refractory solid tumors", Investigational New Drugs, vol. 1, No. 1, pp. 77-84, (2013).

(Continued)

*Primary Examiner* — Sudhakar Katakam

(74) *Attorney, Agent, or Firm* — Dechert LLP; Andrea L. C. Reid; Gang Wang

(57) ABSTRACT

The present invention relates to polypeptides which are covalently bound to aromatic molecular scaffolds such that two or more peptide loops are subtended between attachment points to the scaffold. In particular, the invention describes peptides which are high affinity binders of the Eph receptor tyrosine kinase A2 (EphA2). The invention also includes drug conjugates comprising said peptides, conjugated to one or more effector and/or functional groups, to pharmaceutical compositions comprising said peptide ligands and drug conjugates and to the use of said peptide ligands and dmg conjugates in preventing, suppressing or treating a disease or disorder characterised by overexpression of EphA2 in diseased tissue (such as a tumour).

9 Claims, No Drawings

Specification includes a Sequence Listing.

(56) References Cited

U.S. PATENT DOCUMENTS

| | | |
|---|---|---|
| 2018/0311300 A1 | 11/2018 | Beswick et al. |
| 2018/0362585 A1 | 12/2018 | Teufel et al. |
| 2018/0371020 A1 | 12/2018 | Bennett et al. |
| 2019/0134213 A1 | 5/2019 | Teufel et al. |
| 2019/0184025 A1 | 6/2019 | Chen et al. |
| 2019/0263866 A1 | 8/2019 | Chen et al. |
| 2019/0307836 A1 | 10/2019 | Keen et al. |
| 2019/0389906 A1 | 12/2019 | Beswick et al. |
| 2020/0338203 A1 | 10/2020 | Chen et al. |
| 2021/0040154 A1 | 2/2021 | Mudd et al. |
| 2021/0069287 A1 | 3/2021 | Mudd et al. |
| 2021/0101937 A1 | 4/2021 | Mudd et al. |
| 2021/0147484 A1 | 5/2021 | Beswick et al. |
| 2021/0261620 A1 | 8/2021 | Teufel et al. |
| 2021/0299210 A2 | 9/2021 | Keen et al. |
| 2022/0184222 A1 | 6/2022 | Bennett et al. |
| 2022/0227811 A1 | 7/2022 | Mudd et al. |

FOREIGN PATENT DOCUMENTS

| | | | |
|---|---|---|---|
| WO | 2003063794 A2 | 8/2003 | |
| WO | 2004005348 A1 | 1/2004 | |
| WO | 2004019973 A1 | 3/2004 | |
| WO | 2004077062 A2 | 9/2004 | |
| WO | 2004089925 A1 | 10/2004 | |
| WO | 2005007623 A2 | 1/2005 | |
| WO | 2005103083 A2 | 11/2005 | |
| WO | 2005113554 A2 | 12/2005 | |
| WO | 2006078161 A1 | 7/2006 | |
| WO | 2006078846 A1 | 7/2006 | |
| WO | 2006122806 A2 | 11/2006 | |
| WO | 2007016176 A2 | 2/2007 | |
| WO | 2007044729 A2 | 4/2007 | |
| WO | 2007053452 A1 | 5/2007 | |
| WO | 2007070514 A1 | 6/2007 | |
| WO | 2007084786 A1 | 7/2007 | |
| WO | 2007129161 A2 | 11/2007 | |
| WO | 2008033561 A2 | 3/2008 | |
| WO | 2008039218 A2 | 4/2008 | |
| WO | 2008109943 A1 | 9/2008 | |
| WO | 2008157490 A1 | 12/2008 | |
| WO | WO-2009/098450 A2 | 8/2009 | |
| WO | 2009114512 A1 | 9/2009 | |
| WO | 2011018227 A2 | 2/2011 | |
| WO | 2011090760 A1 | 7/2011 | |
| WO | 2013050617 A1 | 4/2013 | |
| WO | 2014164693 A2 | 10/2014 | |
| WO | 2015171938 A1 | 11/2015 | |
| WO | WO-2016067035 A1 * | 5/2016 | ........... A61K 31/195 |
| WO | 2016171242 A1 | 10/2016 | |
| WO | 2016174103 A1 | 11/2016 | |
| WO | 2017161069 A1 | 9/2017 | |
| WO | WO-2017/191460 A1 | 11/2017 | |
| WO | 2018115204 A1 | 6/2018 | |
| WO | WO-2018/115203 A1 | 6/2018 | |
| WO | 2018127699 A1 | 7/2018 | |
| WO | 2018197509 A1 | 11/2018 | |
| WO | 2019122861 A1 | 6/2019 | |
| WO | WO-2019/122860 A1 | 6/2019 | |
| WO | WO-2019/122863 A1 | 6/2019 | |
| WO | WO-2019/193328 A1 | 10/2019 | |
| WO | WO-2019/243313 A1 | 12/2019 | |
| WO | WO-2020/084305 A1 | 4/2020 | |
| WO | WO-2020/201753 A1 | 10/2020 | |
| WO | 2021019245 A1 | 2/2021 | |
| WO | WO-2021/019243 A1 | 2/2021 | |
| WO | WO-2021/064428 A1 | 4/2021 | |
| WO | WO-2021/105694 A1 | 6/2021 | |
| WO | 2021250418 A1 | 12/2021 | |

OTHER PUBLICATIONS

Bennett et al., "Bicycle Drug Conjugates targeting EphA2 for the treatment of solid tumors: Discovery and selection of BT5528", AACR Annual Meeting 2018, URL:http://www.abstractsonline.com/pp8/#1/4562/presentation/6717.

Bennett et al., "BT5528, a Bicycle Toxin Conjugate targeting EphA2 has potent anti-tumor activity without bleeding or coagulation abnormalities in pre", AACR Annual Meeting 2018.

Bennett et al., "Development of BT1718, a Bicycle Drug Conjugate (BDC) targeting MT1-MMP for treatment of solid tumours", European Journal of Cancer, vol. 69, p. S21, (2016).

Deonarain et al., "Small-Format Drug Conjugates: A Viable Alternative to ADCs for Solid Tumours?", Antibodies, vol. 7, No. 2, p. 16, (2018).

Deyle et al., "Phage Selection of Cyclic Peptides for Application in Research and Drug Development", Accounts of Chemical Research, vol. 50, No. 8, pp. 1866-1874, (2017).

Harrison et al., "Abstract 5144: BT1718, a novel bicyclic peptide-maytansinoid conjugate targeting MT1-MMP for the treatment of solid tumors: Design of bicyclic peptide and linker selection", Cancer Research, vol. 77, No. 13, p. 5144, (2017).

Heinis et al., "Phage-encoded combinatorial chemical libraries based on bicyclic peptides", Nature Chemical Biology, vol. 5, No. 7, pp. 502-507, (2009).

PCT International Search Report for PCT/GB2018/053676 dated Mar. 21, 2018, all pages.

Bennett et al., "Abstract 5855: Bicycle Drug Conjugates Targeting EphA2 for the Treatment of Solid Tumors: Discovery and Selection of BT5528," Cancer Research, 2018, 4 Pages.

Bennett, "BT5528, an EphA2-Targeting Bicycle Toxin Conjugate (BTC): Profound Efficacy Without Bleeding and Coagulation Abnormalities in Animal Models," Association for Cancer Research Annual Meeting, 2019, 11 Pages.

Chen et al., "Peptide Ligands Stabilized by Small Molecules," Angewandte Chemie International Edition. 2014;56(6):1602-1606.

Deyle et al., "Phage Selection of Cyclic Peptides for Application in Research and Drug Development," Accounts of Chemical Research, 2017, vol. 50(8), pp. 1866-1874.

Heinis et al., "Phage-encoded combinatorial chemical libraries based on bicyclic peptides," Nature Chemical Biology 2009; 5(7): 502-507.

Mitra et al., "Structure-Activity Relationship Analysis of Peptides Targeting the EphA2 Receptor," Biochemistry. 2010;49(31):6687-95.

Shi et al., "One-Bead-Two-Compound Thioether Bridged Macrocyclic [gamma] -AApeptide Screening Library Against EphA2," J. Med. Chem. 2017;60(22):9290-9298.

Wu et al., "Design and Characterization of Novel EphA2 Agonists for Targeted Delivery of Chemotherapy to Cancer Cells," Chem. Biol. 2015;22(7):876-887.

PCT International Search Report and Written Opinion for PCT/GB2018/053678 dated Mar. 20, 2018.

PCT International Search Report for PCT Application No. PCT/EP2019/065993, mailed by the European Patent Office dated Sep. 24, 2019, 5 Pages.

Adams, "Molecular control of arterial-venous blood vessel identity," Journal of Anatomy, vol. 202, No. 1, Jan. 2003 (pp. 105-112).

Anonymous, "Bicycle Therapeutics to Present on BT5528, a Bicycle Toxin Conjugate Targeting EphA2 for the Treatment of Solid Tumours, at World ADC 2019", Business Wire, 2019.

Ausiello et al., "Functional topography of discrete domains of human CD38," Tissue Antigens, vol. 56, No. 6, Dec. 2000 (539-547).

Bennett et al., "Abstract 4481: BT5528, an EphA2-targeting Bicycle Toxin Conjugate (BTC): Profound efficacy without bleeding and coagulation abnormalities in animal models." Cancer Res. 2019;79(13 Supplemental):4481.

Bennett et al., "Abstract 5854: BT5528, a Bicycle Toxin Conjugate targeting EphA2 has potent anti-tumor activity without bleeding or coagulation abnormalities in preclinical models." Cancer Research. 2018;78(13 Supplement):5854-5854.

Bennett et al., "Development of BT1718, a Bicycle Drug Conjugate (BTC): Profound Efficacy Without Bleeding and Coagulation Abnormalities in Animal Models," Assocation for Cancer Research Annual Meeting, 2019, 11 pages.

(56) References Cited

OTHER PUBLICATIONS

Bennett et al., "MMAE Delivery Using the Bicycle Toxin Conjugate BT5528." Mol Cancer Ther. 2020;19 (7):1385-1394.
Berge et al., "Pharmaceutical Salts," Journal of Pharmaceutical Sciences, vol. 66, No. 1, Jan. 1977 (pp. 1-19).
Binda et al., "The EphA2 Receptor Drives Self-Renewal and Tumorigenicity in Stem-Like Tumor-Propagating Cells from Human Glioblastomas," Cancer Cell, vol. 22, No. 6, Dec. 2012 (pp. 765-780).
Booth et al., "Crowd control in the crypt," Nature Medicine, vol. 8, No. 12, Dec. 2002 (pp. 1360-1361).
Brannan et al., "EphA2 in the Early Pathogenesis and Progression on Non-Small Cell Lung Cancer," Cancer Prevention Research, vol. 2, No. 12, Dec. 2009 (pp. 1039-1049).
Brantley-Sieders et al., "Eph receptor tyrosine kinases in tumor and tumor microenvironment," Current Pharmaceutical Design, vol. 10, No. 27, No Month Listed 2004 (pp. 3431-3442).
Brantley-Sieders et al., "Eph/Ephrin Profiling in Human Breast Cancer Reveals Significant Associations between Expression Level and Clinical Outcome," PLoS One, vol. 6, No. 9, Sep. 2011 (9 pages).
Brantley-Sieders et al., "Impaired tumor microenvironment in EphA2-deficient mice inhibits tumor angiogenesis and metastatic progression," FASEB Journal, vol. 19, No. 13, Nov. 2005 (pp. 1884-1886).
Center for Diseases, "What Can I Do to Reduce My Risk of Ovarian Cancer," 2021.
Chan and Nie, "Quantum dot bioconjugates for ultrasensitive nonisotopic detection," Science, vol. 281, No. 5385, Sep. 1998 (pp. 2016-2018).
Chang et al., "Five different anti-prostate-specific membrane antigen (PSMA) antibodies confirm PSMA expression in tumor-associated neovasculature," Cancer Research, vol. 59, No. 13, Jul. 1999 (pp. 3192-3198).
Chen et al., "Structurally diverse cyclisation linkers impose different backbone conformations in bicyclic peptides," ChemBioChem, vol. 13, No. 7, May 2012 (pp. 1032-1038).
Cheng et al., "Blockade of EphA receptor tyrosine kinase activation inhibits vascular endothelial cell growth factor-induced angiogenesis," Molecular Cancer Research, vol. 1, No. 1, Nov. 2002 (pp. 2-11).
Cherney et al., "Macrocyclic Amino Carboxylates as Selective MMP-8 Inhibitors," Journal of Medicinal Chemistry, vol. 41, No. 11, May 1998 (pp. 1749-1751).
Chiche et al., "Hypoxia-inducible carbonic anhydrase IX and XII promote tumor cell growth by counteracting acidosis through the regulation of the intracellular pH," Cancer Research, vol. 69, No. 1, Jan. 2009 (pp. 358-368).
Dagher et al., "c-Kit and CD38 are expressed by long-term reconstituting hematopoietic cells present in the murine yolk sac," Biology of Blood and Marrow Transplantation, vol. 4, No. 2, Jun. 1998 (pp. 69-74).
Deaglio et al., "CD38 is a signaling molecule in B-cell chronic lymphocytic leukemia cells," Blood, vol. 102, No. 6, Sep. 2003 (pp. 2146-2155).
Di, "Strategic approaches to optimizing peptide ADME properties," The AAPS Journal, vol. 17, No. 1, Jan. 2015 (pp. 134-143).
Driggers et al., "The exploration of macrocycles for drug discovery—an underexploited structural class," Nature Reviews Drug Discovery, vol. 7, No. 7, Jul. 2008 (pp. 608-624).
Dunne et al., "EphA2 Expression is a Key Driver of Migration and Invasion and a Poor Prognostic Marker in Colorectal Cancer." Clin Cancer Res. 2016;22 (1);230-242.
Duong and Rodan, "The role of integrins in osteoclast function," Journal of Bone and Mineral Metabolism, vol. 17, No. 1, Feb. 1999 (pp. 1-6).
Funaro et al., "Human CD38 is associated to distinct molecules which mediate transmembrane signaling in different Tineages," European Journal of Immunology, vol. 23, No. 10, Oct. 1993 (pp. 2407-2411).
Funaro et al., "Involvement of the multilineage CD38 molecule in a unique pathway of cell activation and proliferation," Journal of Immunology, vol. 145, No. 8, Oct. 1999 (pp. 2390-2396).

Gandhi et al., "MP69-11 Carbonic Anhydrase IX Assay: A Paradigm Shift in Diagnosis of Malignant Cystic Renal Lesions," The Journal of Urology, vol. 193, No. 4S, Supplement, Apr. 2015 (pp. e870-e871).
Guo et al., "Prognostic Significance of Combinations of RNA-Dependent Protein Kinase and EphA2 Biomarkers for NSCLC," Journal of Thoracic Oncology, vol. 8, No. 3, Mar. 2013 (pp. 301-308).
Hess et al., "Molecular Regulation of Tumor Cell Vasculogenic Mimicry by Tyrosine Phosphorylation: Role of Epithelial Cell Kinase (Eck/EphA2)1," Cancer Research, vol. 61, Apr. 2001 (pp. 3250-3255).
Hoshino et al., "Mapping of the catalytic and epitopic sites of human CD38/NAD+ glycohydrolase to a functional domain in the carboxyl terminus," Journal of Immunology, vol. 158, No. 2, Jan. 1997 (pp. 741-747).
International Search Report and Written Opinion issued by the European Patent Office as International Searching Authority for International Application No. PCT/GB2018/051779, dated Sep. 3, 2018 (14 pages).
Jackson et al., "A Human Antibody-Drug Conjugate Targeting EphA2 Inhibits Tumor Growth in vivo." Cancer Research. 2008;68(22):9367-74.
Jin et al., "?V?3 Integrin-Targeted Radionuclide Therapy with 64Cu-cyclam-RAFT-c(-RGDfK-)4," Molecular Cancer Therapy, vol. 15, No. 9, Sep. 2016 (pp. 2076-2085).
Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog," The Journal of Organic Chemistry, vol. 50, No. 26, Dec. 1985 (pp. 5834-5838).
Kinch et al., "Predictive Value of the EphA2 Receptor Tyrosine Kinase in Lung Cancer Recurrence and Survival," Clinical Cancer Research, vol. 9, No. 2, Feb. 2003 (pp. 613-618).
Kitanaka et al., "CD38 ligation in human B cell progenitors triggers tyrosine phosphorylation of CD19 and association o CD19 with lyn and phosphatidylinositol 3-kinase," The Journal of Immunology, vol. 159, No. 1, Jul. 1997 (pp. 184-192).
Kitanaka et al., "CD38-Mediated Signaling Events in Murine Pro-B Cells Expressing Human CD38 With or Without its Cytoplasmic Domain," The Journal of Immunology, vol. 162, Feb. 1999 (pp. 1952-1958).
Konopleva et al., "Ligation of Cell Surface CD38 Protein with Agonistic Monoclonal Antibody Induces a Cell Growth Signal in Myeloid Leukemia Cells," The Journal of Immunology, vol. 161, No. 9, Nov. 1998 (pp. 4702-4708).
Kumagai et al., "Ligation of CD38 Suppresses Human B Lymphopoiesis," The Journal of Experimental Medicine, vol. 181, Mar. 1995 (pp. 1101-1110).
Lee et al., "ADP-ribosyl cyclase and CD38. Multi-functional enzymes in Ca+2 signaling," Advances in Experimental Medicine and Biology, vol. 419, Jun. 1997 (pp. 411-419).
Lee et al., "ADP-ribosyl cyclase: an enzyme that cyclizes NAD+ into a calcium-mobilizing metabolite," Cell Regulation, vol. 2, No. 3, Mar. 1991 (pp. 203-209).
Lee et al., "Structural determination of a cyclic metabolite of NAD+ with intracellular Ca2+-mobilizing activity," The Journal of Biological Chemistry, vol. 264, No. 3, Jan. 1989 (pp. 1608-1615).
Li et al., Up-regulation of EphA2 and down-regulation of EphrinAI are associated with the aggressive phenotype and poor prognosis of malignant glioma, Tumor Biology, vol. 31, No. 5, Oct. 2010 (pp. 477-488).
Lin et al., "EphA2 Overexpression is Associated With Angiogenesis in Ovarian Cancer," Cancer, vol. 109, No. 2, Jan. 2007 (pp. 332-340).
Lund et al., "CD38 Signaling in B Lymphocytes is Controlled by its Ectodomain but Occurs Independently of Enzymatically Generated ADP-Ribose or Cyclic ADP-Ribose," The Journal of Immunology, vol. 162, No. 5, Mar. 1999 (pp. 2693-2702).
Mallone et al., "Signaling through CD38 induces NK cell activation," International Immunology, vol. 13, No. 4, Apr. 2001 (pp. 397-409).

(56) References Cited

OTHER PUBLICATIONS

Marme, "VEGFs, angiopoietins, Ephrins and their receptors: putative targets for tumor therapy?," Annals of Hematology, vol. 81, Suppl. 2, No Month Listed 2002 (S66).
Merritt et al., "Analysis of EphA2 expression and mutant p53 in ovarian carcinoma." Cancer Biol Ther. 2006;5(10):1357-60.
Morra et al., "CD38 is functionally dependent on the TCR/CD3 complex in human T cells," The FASEB Journal, vol. 12, No. 7, May 1998 (pp. 581-592).
Mudali et al., "Patterns of EphA2 protein expression in primary and metastatic pancreatic carcinoma and correlation with genetic status," Clinical and Experimental Metstasis, vol. 23, No. 7-8, Dec. 2006 (pp. 357-365).
Mudd et al., "Identification and Optimization of EphA2-Selective Biccyles for the Delivery of Cytotoxic Payloads," J Med Chem. 2020; 63(8) 4107-4116.
N. N.: "Study BT5528-100 in Patients With Advanced Solid Tumors Associated With EphA2 Expression—Full Text View—ClinicalTrials Study Details Tabular View No Results Posted Disclaimer How to Read a Study Record Study BT5528-100 in Patients With Advanced Solid Tumors Associated With EphA2 Expression Sponsor", U.S. National Library of Medicine, 2019.
N.N., "Bicycle Therapeutics to Present New BT1718 Data in the "New Drugs on the Horizon" Session at the 2018 American Association for Cancer Research Meeting—MarketWatch." 2019.
Nakamoto et al., "Diverse roles for the Eph family of receptor tyrosine kinases in carcinogenesis," Microscopy Research and Techniques, vol. 59, No. 1, Oct. 2002 (pp. 58-67).
Nakamura et al., "EPHA2/EFNA1 expression in human gastric cancer," Cancer Science, vol. 96, No. 1, Jan. 2005 (pp. 42-47).
Nakamura et al., "Involvement of ?v?3 integrins in osteoclast function," Journal of Bone and Mineral Metabolism, vol. 25, No. 6, Nov. 2007 (pp. 337-344).
Nan et al., "Dual Function Glutamate-Related Ligands:? Discovery of a Novel, Potent Inhibitor of Glutamate Carboxypeptidase II Possessing mGluR3 Agonist Activity," Journal of Medicinal Chemistry, vol. 43, No. 5, Feb. 2000 (pp. 772-774).
Neri et al., "Interfering with pH regulation in tumours as a therapeutic strategy," Nature Reviews, vol. 10, Oct. 2011 (pp. 767-777).
Oliver et al., "Mouse CD38 is down-regulated on germinal center B cells and mature plasma cells," Journal of Immunology, vol. 158, No. 3, Feb. 1997 (pp. 1108-1115).
Partida-Sanchez et al., "Cyclic ADP-ribose production by CD38 regulates intracellular calcium release, extracellular calcium influx and chemotaxis in neutrophils and is required for bacterial clearance in vivo," Nature Medicine, vol. 7, No. 11, Nov. 2001 (pp. 1209-1216).
Partida-Sanchez et al., "Regulation of dendritic cell trafficking by the ADP-ribosyl cyclase CD38: impact on the development of humoral immunity," Immunity, vol. 20, No. 3, Mar. 2004 (pp. 279-291).
PCT International Search Report and Written Opinion from PCT/GB2018/053676 dated Mar. 12, 2019.
PCT International Search Report and Written Opinion from PCT/GB2020/050874 dated Jun. 17, 2020.
PCT International Search Report and Written Opinion from PCT/GB2021/051451 dated Sep. 22, 2021.
PCT International Search Report for PCT Application No. PCT/GB2020/051829, mailed by the European Patent Office dated Oct. 30, 2020, 5 Pages.
Pietraszek et al., "Lumican: A new inhibitor of matrix metalloproteinase-14 activity," FEBS Letters, vol. 588, No. 23, Nov. 2014 (pp. 4319-4324).
Poliakov et al., "Diverse roles of eph receptors and ephrins in the regulation of cell migration and tissue assembly," Developmental Cell, vol. 7, No. 4, Oct. 2004 (pp. 465-480).
Ramirez et al., "Defining Causative Factors Contributing in the Activation of Hedgehog Signaling in Diffuse Large B-Cell Lymphoma," Leuk Res. 2012;36(10):1267-1273.

Randall et al., "Expression of murine CD38 defines a population of long-term reconstituting hematopoietic stem cells," Blood, vol. 87, No. 10, May 1996 (pp. 4057-4067).
Remacle et al., "Novel MT1-MMP small-molecule inhibitors based on insights into hemopexin domain function in tumor growth," Cancer Research, vol. 72, No. 9, May 2012 (pp. 2339-2349).
Ridderstad et al., "Kinetics of Establishing the Memory B Cell Population as Revealed by CD38 Expression," Journal of Immunology, vol. 160, No. 10, May 1998 (pp. 4688-4695).
Rodan et al., "Integrin function in osteoclasts," Journal of Endocrinology, vol. 154, No. 3, Sep. 1997 (pp. S47-S56).
Ross et al., "Nothing but skin and bone," The Journal of Clinical Investigation, vol. 116, No. 5, May 2006 (pp. 1140-1149).
Rostovtsev et al., "A Stepwise Huisgen Cycloaddition Process: Copper(I)-Catalyzed Regioselective Ligation of Azides and Terminal Alkynes," Angewandte Chemie International Edition, vol. 41, Jul. 2002 (pp. 2596-2599).
Schulke et al., "The homodimer of prostate-specific membrane antigen is a functional target for cancer therapy," Proceedings of the National Academy of Sciences of the United States of America, vol. 100, No. 22, Oct. 2003 (pp. 12590-12595).
Sounni et al., "MT1-MMP expression promotes tumor growth and angiogenesis through an up-regulation of vascular endothelial growth factor expression," The FASEB Journal, vol. 16, Apr. 2002 (pp. 555-564).
Stein et al., "Eph receptors discriminate specific ligand oligomers to determine alternative signaling complexes, attachment, and assembly? responses," Genes & Development, vol. 12, 1998 (pp. 667-678).
Stevenson et al., "Preliminary Studies for an Immunotherapeutic Approach to the Treatment of Human Myeloma Using Chimeric Anti-CD38 Antibody," Blood, vol. 77, No. 5, Mar. 1991 (pp. 1071-1079).
Sun et al., "Carbohydrate and Protein Immobilization onto Solid Surfaces by Sequential Diels-Alder and Azide-Alkyne Cycloadditions," Bioconjugate Chemistry, vol. 17, No. 1, Jan.-Feb. 2006 (pp. 52-57).
Superan, "Carbonic anhydrases: novel therapeutic applications for inhibitors and activators," Nature Reviews Drug Discovery, vol. 7, No. 2, Feb. 2008 (pp. 168-181).
Tandon et al., "Emerging strategies for EphA2 receptor targeting for cancer therapeutics." Expert Opin Ther Targets. 2011;15(1):31-51.
Tasch et al., "A unique folate hydrolase, prostate-specific membrane antigen (PSMA): A target for immunotherapy?" Critical Reviews in Immunology, vol. 21, No. 1-3, No Month Listed 2001 (pp. 249-261).
Teitelbaum, "Osteoclasts, integrins, and osteoporosis," Journal of Bone and Mineral Metabolism, vol. 18, No. 6, Oct. 2000 (pp. 344-349).
Teitelbaum, "Osteoporosis and Integrins," The Journal of Clinical Endocrinology & Metabolism, vol. 90, No. 4, Apr. 2005 (pp. 2466-2468).
Teti et al., "The Role of the AlphaVbeta3 Integrin in the Development of Osteolytic Bone Metastases: A Pharmacological Target for Alternative Therapy?" Calcified Tissue International, vol. 71, No. 4, Oct. 2002 (pp. 293-299).
Teufel et al., "Backbone-driven collapse in unfolded protein chains," Journal of Molecular Biology, vol. 409, No. 2, Jun. 2011 (pp. 250-262).
Timmerman et al., "Rapid and quantitative cyclization of multiple peptide loops onto synthetic scaffolds for structural mimicry of protein surfaces," Chembiochem, vol. 6, No. 5, May 2005 (pp. 821-824).
Todisco et al., "CD38 ligation inhibits normal and leukemic myelopoiesis," Blood, vol. 95, No. 2, Jan. 2000 (pp. 535-542).
U.S. Appl. No. 16/771,186, filed Jun. 9, 2020.
U.S. Appl. No. 17/592,966, filed Feb. 4, 2022.
U.S. Appl. No. 17/630,314, filed Jan. 26, 2022.
U.S. Appl. No. 17/630,747, filed Jan. 27, 2022.
U.S. Appl. No. 17/655,822, filed Mar. 22, 2022.
U.S. Appl. No. 17/663,169, filed May 12, 2022.
U.S. Appl. No. 17/779,226, filed May 24, 2022.
Uckun, "Regulation of Human B-Cell Ontogeny," Blood, vol. 76, No. 10, Nov. 1990 (pp. 1908-1923).

(56) References Cited

OTHER PUBLICATIONS

Walker-Daniels et al., "Overexpression of the EphA2 tyrosine kinase in prostate cancer," Prostate, vol. 41, No. 4, Dec. 1999 (pp. 275-280).
Wallbrecher et al., "Exploration of the Design Principles of a Cell-Penetrating Bicyclic Peptide Scaffold," Bioconjugate Chem. 2014, vol. 25, pp. 955-964.
Wang et al., "Probing for Integrin ?v?3 Binding of RGD Peptides Using Fluorescence Polarization," Bioconjugate Chemistry, vol. 16, No. 3, May-Jun. 2005 (pp. 729-734).
Wang, "An exact mathematical expression for describing competitive binding of two different ligands to a protein molecule," FEBS Letters, vol. 360, No. 2, Feb. 1995 (pp. 111-114).
Wind et al., "Measuring carbonic anhydrase IX as a hypoxia biomarker: differences in concentrations in serum and plasma using a commercial enzyme-linked immunosorbent assay due to influences of metal ions," Annals of Clinical Biochemistry, vol. 48, No. 2, Mar. 2011 (pp. 112-120).
Wu et al., "Structures of the CXCR4 Chemokine GPCR with Small-Molecule and Cyclic Peptide Antagonists," Science, vol. 330, No. 6007, Nov. 2010 (pp. 1066-1071).
Wykosky et al., "EphA2 as a Novel Molecular Marker and Target in Glioblastoma Multiforme," Molecular Cancer Research, vol. 3, No. 10, Oct. 2005 (pp. 541-551).
Xiong et al., "Crystal Structure of the Extracellular Segment of Integrin ?V?3 in Complex with an Arg-Gly-Asp Ligand," Science, vol. 296, No. 5565, Apr. 2002 (pp. 151-155).
Yang et al., "Overexpression of EphA2, MMP?9, and MVD?CD34 in hepatocellular carcinoma: Implications for tumor progression and prognosis," Hepatology Research, vol. 39, No. 12, Dec. 2009 (pp. 1169-1177).
Yuan et al., "Over-Expression of EphA2 and EphrinA-1 in Human Gastric Adenocarcinoma and its Prognostic Value for Postoperative Patients," Digestive Diseases and Sciences, vol. 54, No. 11, Nov. 2009 (pp. 2410-2417).
Zelinski et al., "EphA2 overexpression causes tumorigenesis of mammary epithelial cells," Cancer Research, vol. 61, No. 5, Mar. 2001 (pp. 2301-2306).
Zhao et al., "Structural basis of specificity of a peptidyl urokinase inhibitor, upain-1," Journal of Structural Biology, vol. 160, No. 1, Oct. 2007 (pp. 1-10).
Zhuang et al., "Elevation of receptor tyrosine kinase EphA2 mediates resistance to trastuzumab therapy," Cancer Research, vol. 70, No. 1, Jan. 2010 (pp. 299-308).
Zilber et al., "CD38 expressed on human monocytes: A coaccessory molecule in the superantigen-induced proliferation," Proceedings of the National Academy of Sciences of the United States of America, vol. 97, No. 6, Mar. 2000 (pp. 2840-2845).
Zubiaur et al., "CD38 ligation results in activation of the Raf-1/mitogen-activated protein kinase and the CD3-zeta/zeta-associated protein-70 signaling pathways in Jurkat T lymphocytes," Journal of Immunology, vol. 159, No. 1, Jul. 1997 (pp. 193-205).
Zupo et al., "CD38 signaling by agonistic monoclonal antibody prevents apoptosis of human germinal center B cells," European Journal of Immunology, vol. 24, No. 5, May 1994 (pp. 1218-1222).

\* cited by examiner

BICYCLIC PEPTIDE LIGANDS SPECIFIC FOR EPHA2

CROSS-REFERENCE TO RELATED APPLICATIONS

This application is a U.S. national stage application under 35 U.S.C. § 371 of International Application No. PCT/GB2018/053676, filed Dec. 19, 2018, which claims priority under 35 U.S.C. § 119 to United Kingdom Application No. GB1721265.5, filed Dec. 19, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 9, 2020, is named 174712.txt and is 98.6 kilobytes in size.

FIELD OF THE INVENTION

The present invention relates to polypeptides which are covalently bound to aromatic molecular scaffolds such that two or more peptide loops are subtended between attachment points to the scaffold. In particular, the invention describes peptides which are high affinity binders of the Eph receptor tyrosine kinase A2 (EphA2). The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder characterised by overexpression of EphA2 in diseased tissue (such as a tumour).

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, (MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a peptide ligand specific for EphA2 comprising a polypeptide comprising at least three cysteine residues, separated by at least two loop sequences, and an aromatic molecular scaffold which forms covalent bonds with the cysteine residues of the polypeptide such that at least two polypeptide loops are formed on the molecular scaffold.

According to a further aspect of the invention, there is provided a drug conjugate comprising a peptide ligand as defined herein conjugated to one or more effector and/or functional groups.

According to a further aspect of the invention, there is provided a pharmaceutical composition comprising a peptide ligand or a drug conjugate as defined herein in combination with one or more pharmaceutically acceptable excipients.

According to a further aspect of the invention, there is provided a peptide ligand or drug conjugate as defined herein for use in preventing, suppressing or treating a disease or disorder characterised by overexpression of EphA2 in diseased tissue (such as a tumour).

DETAILED DESCRIPTION OF THE INVENTION

In one embodiment, said loop sequences comprise 4, 5, 6 or 7 amino acid acids.

In a further embodiment, said loop sequences comprise three cysteine residues separated by two loop sequences both of which consist of 5 amino acids (such as those listed in Tables 3, 4 and 9).

In a further embodiment, said loop sequences comprise three cysteine residues separated by two loop sequences both of which consist of 6 amino acids (such as those listed in Tables 3 to 10).

In a further embodiment, said loop sequences comprise three cysteine residues separated by two loop sequences one of which consists of 6 amino acids and the other of which consists of 5 amino acids (such as those listed in Table 4).

In a further embodiment, said loop sequences comprise three cysteine residues separated by two loop sequences one of which consists of 6 amino acids and the other of which consists of 4 amino acids (such as those listed in Table 4).

In a further embodiment, said loop sequences comprise three cysteine residues separated by two loop sequences one of which consists of 6 amino acids and the other of which consists of 7 amino acids (such as those listed in Table 8).

In one embodiment, the peptide ligand comprises an amino acid sequence selected from:

$C_i$—$X_1$—$C_{ii}$—$X_2$—$C_{iii}$ wherein $X_1$ and $X_2$ represent the amino acid residues between the cysteine residues listed in Tables 3 to 10 and $C_i$, $C_{ii}$ and $C_{iii}$ represent first, second and third cysteine residues, respectively or a pharmaceutically acceptable salt thereof.

In a further embodiment, the peptide ligand comprises an amino acid sequence selected from one or more of the peptide ligands listed in one or more Tables 3 to 10.

In one embodiment, the molecular scaffold is selected from (1,3,5-tris(bromomethyl)benzene) (TBMB) and the peptide ligand is selected from any one of the peptide ligands listed in Tables 3 to 10.

In one embodiment, the peptide ligand is selected from any one of Compounds 1-308 or a pharmaceutically acceptable salt thereof.

In a further embodiment, the peptide ligand is selected from any one of Compounds 1-286, 289, 292-293 and 296-297 or a pharmaceutically acceptable salt thereof.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4th ed., John Wiley & Sons, Inc.), which are incorporated herein by reference.

Nomenclature

Numbering

When referring to amino acid residue positions within the peptides of the invention, cysteine residues ($C_i$, $C_{ii}$ and $C_{iii}$) are omitted from the numbering as they are invariant, therefore, the numbering of amino acid residues within the peptides of the invention is referred to as below:

(SEQ ID NO: 1)

-$C_i$-$M_1$-$N_2$-$D_3$-$W_4$-$L_5$-$C_{ii}$-$S_6$-$L_7$-$G_8$-$W_9$-$T_{10}$-$C_{iii}$-.

For the purpose of this description, all bicyclic peptides are assumed to be cyclised with either TBMB (1,3,5-tris(bromomethyl)benzene) yielding a tri-substituted 1,3,5-trismethylbenzene structure. Cyclisation with TBMB occurs on $C_i$, $C_{ii}$, and $C_{iii}$.

Molecular Format

N- or C-terminal extensions to the bicycle core sequence are added to the left or right side of the sequence, separated by a hyphen. For example, an N-terminal (β-Ala)-$Sar_{10}$-Ala tail would be denoted as:

(SEQ ID NO: X)

(β-Ala)-$Sar_{10}$-A-.

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus become C-terminus and vice versa) and their stereochemistry is likewise also reversed (i.e. D-amino acids become L-amino acids and vice versa).

Peptide Ligands

A peptide ligand, as referred to herein, refers to a peptide, peptidic or peptidomimetic covalently bound to a molecular scaffold. Typically, such peptides, peptidics or peptidomimetics comprise a peptide having natural or non-natural amino acids, two or more reactive groups (i.e. cysteine residues) which are capable of forming covalent bonds to the scaffold, and a sequence subtended between said reactive groups which is referred to as the loop sequence, since it forms a loop when the peptide, peptidic or peptidomimetic is bound to the scaffold. In the present case, the peptides, peptidics or peptidomimetics comprise at least three cysteine residues (referred to herein as $C_i$, $C_{ii}$, and $C_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should in most circumstances demonstrate stability to plasma proteases, epithelial ("membrane-anchored") proteases, gastric and intestinal proteases, lung surface proteases, intracellular proteases and the like. Protease stability should be maintained between different species such that a bicyclic peptide lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes;

An optimal plasma half-life in the circulation. Depending upon the clinical indication and treatment regimen, it may be required to develop a bicyclic peptide with short or prolonged in vivo exposure times for the management of either chronic or acute disease states. The optimal exposure time will be governed by the requirement for sustained exposure (for maximal therapeutic efficiency) versus the requirement for short exposure times to minimise toxicological effects arising from sustained exposure to the agent; and Selectivity. Certain peptide ligands of the invention demonstrate good selectivity over other Eph receptor tyrosine kinases, such as EphA1, EphA3, EphA4, EphA6, EphA7 and EphB1 and factor XIIA, carbonic anhy-

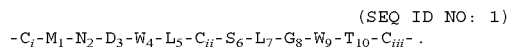

drase 9 and CD38 (selectivity data for selected peptide ligands of the invention may be seen in Table 12). It should also be noted that selected peptide ligands of the invention exhibit cross reactivity with other species (eg mouse) to permit testing in animal models (Tables 3, 5, 7, 8 and 11).

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO$^-$), then a salt may be formed with an organic or inorganic base, generating a suitable cation. Examples of suitable inorganic cations include, but are not limited to, alkali metal ions such as Li$^+$, Na$^+$ and K$^+$, alkaline earth metal cations such as Ca$^{2+}$ and Mg$^{2+}$, and other cations such as Al$^{3+}$ or Zn$^+$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with one or more replacement amino acids, such as an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal residue is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal residue is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises removal of any amino acid residues and substitution with alanines, such as D-alanines. This embodiment provides the advantage of identifying key binding residues and removing potential proteolytic attack site(s). The results of such alanine, such as D-alanine substitutions (also known as alanine scanning) may be seen in Table 9.

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^{2}H$ (D) and $^{3}H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, sulfur, such as $^{35}S$, copper, such as $^{64}Cu$, gallium, such as $^{67}Ga$ or $^{68}Ga$, yttrium, such as $^{90}Y$ and lutetium, such as $^{177}Lu$, and Bismuth, such as $^{213}Bi$.

Certain isotopically-labelled peptide ligands of the invention, for example, those incorporating a radioactive isotope, are useful in drug and/or substrate tissue distribution studies, and to clinically assess the presence and/or absence of the EphA2 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}H$ (T), and carbon-14, i.e. $^{14}C$, are particularly useful for this purpose in view of their ease of incorporation and ready means of detection.

Substitution with heavier isotopes such as deuterium, i.e. $^2H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Aromatic Molecular Scaffold

References herein to the term "aromatic molecular scaffold" refer to any molecular scaffold as defined herein which contains an aromatic (i.e. unsaturated) carbocyclic or heterocyclic ring system.

It will be appreciated that the aromatic molecular scaffold may comprise an aromatic moiety. Examples of suitable aromatic moieties within the aromatic scaffold include biphenylene, terphenylene, naphthalene or anthracene.

It will also be appreciated that the aromatic molecular scaffold may comprise a heteroaromatic moiety. Examples of suitable heteroaromatic moieties within the aromatic scaffold include pyridine, pyrimidine, pyrrole, furan and thiopene.

It will also be appreciated that the aromatic molecular scaffold may comprise a halomethylarene moiety, such as a bis(bromomethyl)benzene, a tris(bromomethyl)benzene, a tetra(bromomethyl)benzene or derivatives thereof.

Non-limiting examples of aromatic molecular scaffolds include: bis-, tris-, or tetra(halomethyl)benzene; bis-, tris-, or tetra(halomethyl)pyridine; bis-, tris-, or tetra(halomethyl)pyridazine; bis-, tris-, or tetra(halomethyl)pyrimidine; bis-, tris-, or tetra(halomethyl)pyrazine; bis-, tris-, or tetra(halomethyl)-1,2,3-triazine; bis-, tris-, or tetra-halomethyl)-1,2,4-triazine; bis-, tris-, or tetra(halomethyl)pyrrole, -furan, -thiophene; bis-, tris-, or tetra(halomethyl)imidazole, -oxazole, -thiazol; bis-, tris-, or tetra(halomethyl)-3H-pyrazole, -isooxazole, -isothiazol; bis-, tris-, or tetra(halomethyl)biphenylene; bis-, tris-, or tetra(halomethyl)terphenylene; 1,8-bis(halomethyl)naphthalene; bis-, tris-, or tetra(halomethyl) anthracene; and bis-, tris-, or tetra(2-halomethylphenyl) methane.

More specific examples of aromatic molecular scaffolds include: 1,2-bis(halomethyl)benzene; 3,4-bis(halomethyl) pyridine; 3,4-bis(halomethyl)pyridazine; 4,5-bis(halomethyl)pyrimidine; 4,5-bis(halomethyl)pyrazine; 4,5-bis(halomethyl)-1,2,3-triazine; 5,6-bis(halomethyl)-1,2,4-triazine; 3,4-bis(halomethyl)pyrrole, -furan, -thiophene and other regioisomers; 4,5-bis(halomethyl)imidazole, -oxazole, -thiazol; 4,5-bis(halomethyl)-3H-pyrazole, -isooxazole, -isothiazol; 2,2'-bis(halomethyl)biphenylene; 2,2"-bis(halomethyl) terphenylene; 1,8-bis(halomethyl)naphthalene; 1,10-bis (halomethyl)anthracene; bis(2-halomethylphenyl)methane; 1,2,3-tris(halomethyl)benzene; 2,3,4-tris(halomethyl)pyridine; 2,3,4-tris(halomethyl)pyridazine; 3,4,5-tris(halomethyl)pyrimidine; 4,5,6-tris(halomethyl)-1,2,3-triazine; 2,3,4-tris(halomethyl)pyrrole, -furan, -thiophene; 2,4,5-bis (halomethyl)imidazole, -oxazole, -thiazol; 3,4,5-bis (halomethyl)-1H-pyrazole, -isooxazole, -isothiazol; 2,4,2'-tris(halomethyl)biphenylene; 2,3', 2"-tris(halomethyl) terphenylene; 1,3,8-tris(halomethyl)naphthalene; 1,3,10-tris (halomethyl)anthracene; bis(2-halomethylphenyl)methane; 1,2,4,5-tetra(halomethyl)benzene; 1,2,4,5-tetra(halomethyl) pyridine; 2,4,5,6-tetra(halomethyl)pyrimidine; 2,3,4,5-tetra (halomethyl)pyrrole, -furan, -thiophene; 2,2',6,6'-tetra(halomethyl)biphenylene; 2,2",6,6"-tetra(halomethyl) terphenylene; 2,3,5,6-tetra(halomethyl)naphthalene and 2,3, 7,8-tetra(halomethyl)anthracene; and bis(2,4-bis(halomethyl)phenyl)methane.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of tris(bromomethyl)benzene, especially 1,3,5-tris(bromomethyl)benzene ('TBMB'), or a derivative thereof.

In one embodiment, the molecular scaffold is 2,4,6-tris (bromomethyl)mesitylene. This molecule is similar to 1,3, 5-tris(bromomethyl)benzene but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene (the scaffold reactive group exemplified by TBMB) or iodoacetamide. Other scaffold reactive groups that are used to selectively couple compounds to cysteines in proteins are maleimides, αβ unsaturated carbonyl containing compounds and α-halomethylcarbonyl containing compounds. Examples of maleimides which may be used as molecular scaffolds in the invention include: tris-(2-maleimidoethyl)amine, tris-(2-maleimidoethyl)benzene, tris-(maleimido)benzene. An example of an α-halomethylcarbonyl containing compound is N,N',N"-(benzene-1,3,5-triyl)tris(2-bromoacetamide). Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p10444), the 18 amino acid 'model amphipathic peptide' (Oehlke et al (1998) Biochim Biophys Acts Volume 1414 p127) and arginine rich regions of the HIV TAT protein. Non peptidic approaches include the use of small molecule mimics or SMOCs that can be easily attached to biomolecules (Okuyama et al (2007) Nature Methods Volume 4 p153). Other chemical strategies to add guanidinium groups to molecules also enhance cell penetration (Elson-Scwab et al (2007) J Biol Chem Volume 282 p13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half life in the range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one particular embodiment of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamycins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

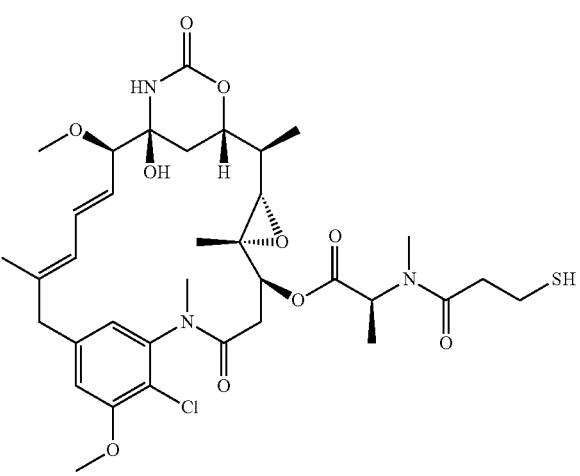

Monomethyl auristatin E (MMAE) is a synthetic antineoplastic agent and has the following structure:

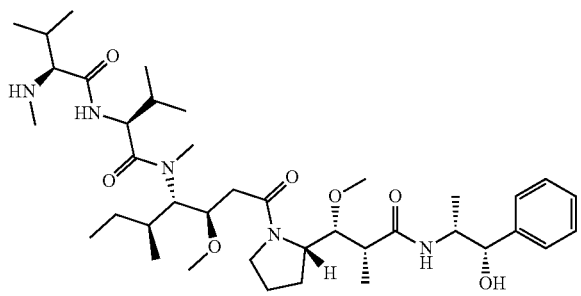 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

In one yet further particular embodiment of the invention, the cytotoxic agent is selected from maytansinoids (such as DM1). Data is presented herein in Table 11 which demonstrates the effects of peptide ligands conjugated to toxins containing DM1.

In one embodiment, the cytotoxic agent is linked to the bicyclic peptide by a cleavable bond, such as a disulphide bond or a protease sensitive bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

In one embodiment, the cytotoxic agent and linker is selected from any combinations of those described in WO 2016/067035 (the cytotoxic agents and linkers thereof are herein incorporated by reference).

In one embodiment, the cytotoxic agent is DM1 and the drug conjugate comprises a compound of formula (A):

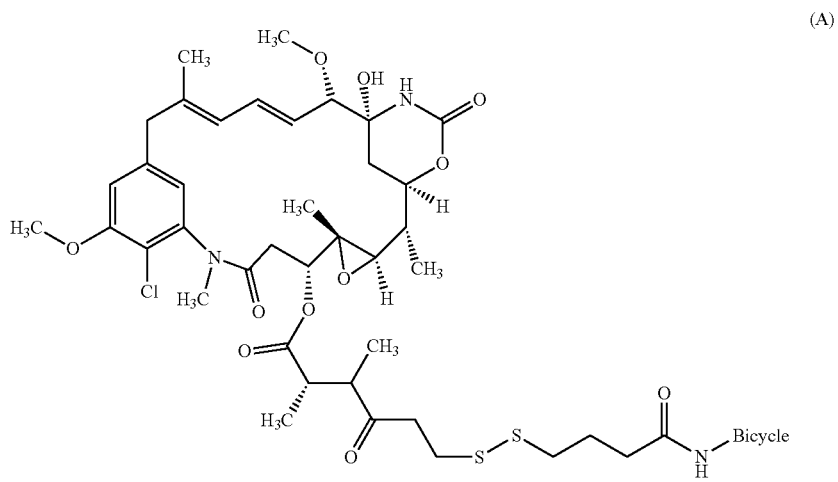

wherein said bicycle is selected from any one of Compound 72 as defined herein.

In an alternative embodiment, the cytotoxic agent is DM1 and the drug conjugate comprises a compound of formula (B):

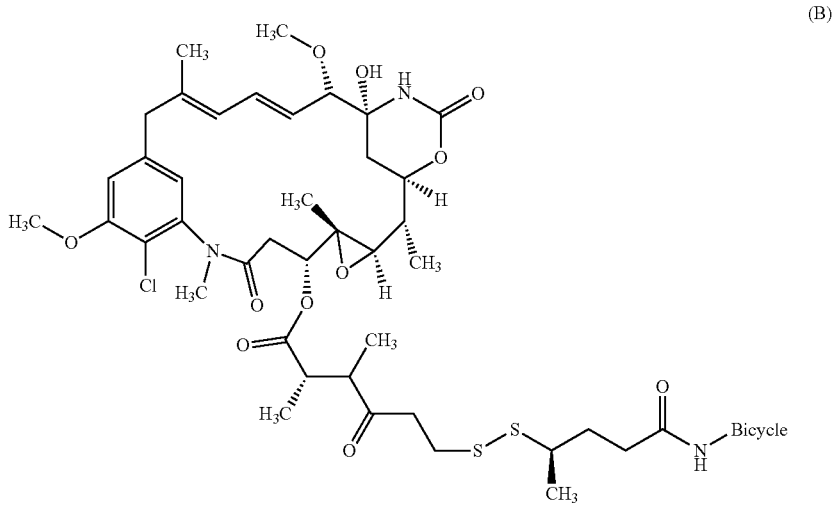

(B)

wherein said bicycle is selected from any one of Compounds 72, 226, 227 and 303 as defined herein.

In one embodiment, the cytotoxic agent is DM1 and the drug conjugate comprises a compound of formula (A), wherein said bicycle is selected from Compound 72 as defined herein. This BDC is known herein as BDC-1. Data is presented herein which demonstrates excellent competition binding for BDC-1 in the EphA2 competition binding assay as shown in Table 11.

In an alternative embodiment, the cytotoxic agent is DM1 and the drug conjugate comprises a compound of formula (B), wherein said bicycle is selected from Compound 72 as defined herein. This BDC is known herein as BDC-2. Data is presented herein which demonstrates excellent competition binding for BDC-2 in the EphA2 competition binding assay as shown in Table 11.

In an alternative embodiment, the cytotoxic agent is DM1 and the drug conjugate comprises a compound of formula (B), wherein said bicycle is selected from Compound 226 as defined herein. This BDC is known herein as BDC-3. Data is presented herein which demonstrates excellent competition binding for BDC-3 in the EphA2 competition binding assay as shown in Table 11.

In an alternative embodiment, the cytotoxic agent is DM1 and the drug conjugate comprises a compound of formula (B), wherein said bicycle is selected from Compound 227 as defined herein. This BDC is known herein as BDC-4. Data is presented herein which demonstrates excellent competition binding for BDC-4 in the EphA2 competition binding assay as shown in Table 11.

In an alternative embodiment, the cytotoxic agent is DM1 and the drug conjugate comprises a compound of formula (B), wherein said bicycle is selected from Compound 303 as defined herein. This BDC is known herein as BDC-5. Data is presented herein which demonstrates excellent competition binding for BDC-5 in the EphA2 competition binding assay as shown in Table 11.

In one embodiment, the drug conjugate is selected from BDC-1 to BDC-5. In a further embodiment, the drug conjugate is selected from BDC-1 to BDC-4.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TBMB) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as EphA2 binding agents.

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov et al. (2004) Dev Cell 7, 465-80). Functional and biochemical Eph responses occur at higher ligand oligomerization states (Stein et al. (1998) Genes Dev 12, 667-678).

Among other patterning functions, various Ephs and ephrins have been shown to play a role in vascular development. Knockout of EphB4 and ephrin-B2 results in a lack of the ability to remodel capillary beds into blood vessels (Poliakov et al., supra) and embryonic lethality. Persistent expression of some Eph receptors and ephrins has also been observed in newly-formed, adult micro-vessels (Brantley-Sieders et al. (2004) Curr Pharm Des 10, 3431-42; Adams (2003) J Anat 202, 105-12).

The de-regulated re-emergence of some ephrins and their receptors in adults also has been observed to contribute to tumor invasion, metastasis and neo-angiogenesis (Nakamoto et al.

(2002) Microsc Res Tech 59, 58-67; Brantley-Sieders et al., supra). Furthermore, some Eph family members have been found to be over-expressed on tumor cells from a variety of human tumors (Brantley-Sieders et al., supra); Marme (2002) Ann Hematol 81 Suppl 2, S66; Booth et al. (2002) Nat Med 8, 1360-1).

EPH receptor A2 (ephrin type-A receptor 2) is a protein that in humans is encoded by the EPHA2 gene.

EphA2 is upregulated in multiple cancers in man, often correlating with disease progression, metastasis and poor prognosis e.g.: breast (Zelinski et al (2001) Cancer Res. 61, 2301-2306; Zhuang et al (2010) Cancer Res. 70, 299-308;

Brantley-Sieders et al (2011) PLoS One 6, e24426), lung (Brannan et al (2009) Cancer Prev Res (Phila) 2, 1039-1049; Kinch et al (2003) Clin Cancer Res. 9, 613-618; Guo et al (2013) J Thorac Oncol. 8, 301-308), gastric (Nakamura et al (2005) Cancer Sci. 96, 42-47; Yuan et al (2009) Dig Dis Sci 54, 2410-2417), pancreatic (Mudali et al (2006) Clin Exp Metastasis 23, 357-365), prostate (Walker-Daniels et al (1999) Prostate 41, 275-280), liver (Yang et al (2009) Hepatol Res. 39, 1169-1177) and glioblastoma (Wykosky et al (2005) Mol Cancer Res. 3, 541-551; Li et al (2010) Tumour Biol. 31, 477-488).

The full role of EphA2 in cancer progression is still not defined although there is evidence for interaction at numerous stages of cancer progression including tumour cell growth, survival, invasion and angiogenesis. Downregulation of EphA2 expression suppresses tumour cancer cell propagation (Binda et al (2012) Cancer Cell 22, 765-780), whilst EphA2 blockade inhibits VEGF induced cell migration (Hess et al (2001) Cancer Res. 61, 3250-3255), sprouting and angiogenesis (Cheng et al (2002) Mol Cancer Res. 1, 2-11; Lin et al (2007) Cancer 109, 332-40) and metastatic progression (Brantley-Sieders et al (2005) FASEB J. 19, 1884-1886).

An antibody drug conjugate to EphA2 has been shown to significantly diminish tumour growth in rat and mouse xenograft models (Jackson et al (2008) Cancer Research 68, 9367-9374) and a similar approach has been tried in man although treatment had to be discontinued for treatment related adverse events (Annunziata et al (2013) Invest New drugs 31, 77-84).

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a peptide ligand or a drug conjugate as defined herein, for use in preventing, suppressing or treating a disease or disorder characterised by overexpression of EphA2 in diseased tissue (such as a tumour).

According to a further aspect of the invention, there is provided a method of preventing, suppressing or treating a disease or disorder characterised by overexpression of EphA2 in diseased tissue (such as a tumour), which comprises administering to a patient in need thereof an effector group and drug conjugate of the peptide ligand as defined herein.

In one embodiment, the EphA2 is mammalian EphA2. In a further embodiment, the mammalian EphA2 is human EphA2.

In one embodiment, the disease or disorder characterised by overexpression of EphA2 in diseased tissue is selected from cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchoalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from: breast cancer, lung cancer, gastric cancer, pancreatic cancer, prostate cancer, liver cancer, glioblastoma and angiogenesis.

In a yet further embodiment, the cancer is selected from lung cancer, such as non-small cell lung carcinomas. Data is presented herein which demonstrates that a BDC of the invention (BDC-8) completely eradicated non-small cell lung carcinomas from day 32 and no tumour regrowth occurred following dosing suspension on day 28. This data clearly demonstrates the clinical utility of the BDCs of the present invention in cancers such as lung cancers, in particular non-small cell lung carcinomas.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLE

| Abbreviations | Name | Precursor Name | Precursor CAS | Supplier |
|---|---|---|---|---|
| 1Nal | 1-Naphthylalanine | Fmoc-3-(1-naphthyl)-L-alanine | 96402-49-2 | Fluorochem |
| 2FuAla | 2-Furylalanine | Fmoc-L-2-furylalanine | 159611-02-6 | Combi Blocks |
| 2Nal | 2-Naphthylalanine | Fmoc-3-(2-naphthyl)-L-alanine | 112883-43-9 | Alfa Aesar |
| 3,3-DPA | 3,3-Diphenylalanine | fmoc-3,3-diphenylalanine | 189937-46-0 | Alfa Aesar |
| 3,4-DCPhe | 3,4-Dichlorophenylalanine | Fmoc-3,4-dichloro-L-phenylalanine | 17766-59-5 | PolyPeptide |
| 3Pal | 3-(3-Pyridyl)-Alanine | N-Fmoc-3-(3-pyridyl)-Lβnine | 175453-07-3 | Fluorochem |
| 4,4-BPA | 4,4'-Biphenylalanine | Fmoc-L-4,4'-Biphenylalanine | 199110-64-0 | Alfa Aesar |
| 4BenzylPro | 4-Benzyl-pyrrolidine-2-carboxylic acid | Fmoc-4-Benzyl-pyrrolidine-2-carboxylic acid | | PolyPeptide |
| 4BrPhe | 4-Bromophenylalanine | Fmoc-4-Bromo-L-phenylalanine | 198561-04-5 | PolyPeptide |
| 4FlPro | 4-Fluoro-pyrrolidine-2-carboxylic acid | Fmoc-4-fluoro-pyrrolidine-2-carboxylic acid | 203866-19-7 | PolyPeptide |
| 4MeoPhe | 4-Methoxyphenylalanine | Fmoc-4-Methoxyphenylalanine | 77128-72-4 | Iris Biotech |
| 4Pal | 3-(4-Pyridyl)-Alanine | N-Fmoc-3-(4-pyridyl)-L-alanine | 169555-95-7 | Fluorochem |
| 4PhenylPro | 4-Phenyl-pyrrolidine-2-carboxylic acid | Fmoc-4-phenyl-pyrrolidine-2-carboxylic acid | 269078-71-9 | Cambridge Bioscience |
| Ac | Acetyl | | | |
| AC3C | 1-Aminocyclopropane-1-carboxylic acid | 1-(Fmoc-amino)cyclopropanecarboxylic acid | 126705-22-4 | Iris Biotech |
| AC4C | 1-Amino-1-cyclobutanecarboxylic acid | 1-(Fmoc-amino)-cyclobutylcarboxylic acid | 885951-77-9 | Fluorochem |
| AC5C | 1-Amino-1-cyclopentanecarboxylic acid | 1-(Fmoc-amino)cyclopentanecarboxylic acid | 117322-30-2 | Iris Biotech |
| AF488 | AlexaFluor488 | AlexaFluor488-NHS Ester | | Fisher Scientific |
| Aib | 2-Aminoisobutyric acid | Fmoc-α-aminoisobutyric acid | 94744-50-0 | Fluorochem |
| Aza-Gly | Azaglycine | | | |
| Aze | Azetidine | Fmoc-L-azetidine-2-carboxylic acid | 136552-06-2 | Combi Blocks |
| β-Ala | β-Alanine | Fmoc-β-alanine | 35737-10-1 | Fluorochem |
| C5g | Cyclopentylglycine | Fmoc-L-cyclopentylglycine | 220497-61-0 | Fluorochem |
| Cba | β-Cyclobutylalanine | Fmoc-β-cyclobutyl-L-alanine | 478183-62-9 | IRIS Biotech GmbH |
| Cpa | β-Cyclopropylalanine | Fmoc-β-cyclopropyl-L-alanine | 214750-76-2 | Fluorochem |
| Cpg | Cyclopropylglycine | Fmoc-L-cyclopropylglycine | 1212257-18-5 | Apollo Scientific |
| DOTA | 1,4,7,10-tetraazacyclododecane-1,4,7,10-tetraacetic acid | | | |
| Fl | 5(6)-carboxyfluorescein | | | Sigma |
| HArg | HomoArginine | Fmoc-L-HomoArg(Pbf)-OH | 401915-53-5 | Fluorochem |

-continued

| Abbreviations | Name | Precursor Name | Precursor CAS | Supplier |
|---|---|---|---|---|
| HPhe | HomoPhenylalanine | Fmoc-L-Homophenylalanine | 132684-59-4 | Iris Biotech |
| HyP | Hydroxyproline | Fmoc-Hydroxyproline(tBu)-OH | 122996-47-8 | Sigma |
| NO2Phe | 4-Nitrophenylalanine | Fmoc-4-nitro-L-phenylalanine | 95753-55-2 | PolyPeptide |
| Phg | Phenylglycine | Fmoc-L-phenylglycine | 102410-65-1 | Combi Blocks |
| Pip | Pipecolic acid | Fmoc-L-Pipecolic acid | 86069-86-5 | Peptech |
| Sar | Sarcosine, such that $Sar_x$ represents x Sar residues | Fmoc-Sarcosine-OH | 77128-70-2 | Sigma |
| tBuGly | Tert-leucine | Fmoc-L-tert-leucine | 132684-60-7 | Fluorochem |
| Thi | 2-Thienylalanine | Fmoc-2-Thienylalanine | 130309-35-2 | Novabiochem |
| ThiAz | 3-(1,2,4-triazol-1-yl)-Alanine | Fmoc-3-(1,2,4-triazol-1-yl)-Ala-OH | 1217449-37-0 | Sigma |
| ΨAla | Reduced amide on backbone | | | |

Materials and Methods

Peptide Synthesis

Peptide synthesis was based on Fmoc chemistry, using a Symphony and SymphonyX peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology. Peptides were purified by HPLC and following isolation they were modified with 1,3,5-tris(bromomethyl)benzene (TBMB, Sigma). For this, linear peptide was diluted with $H_2O$ up to ~35 mL, ~500 μL of 100 mM TBMB in acetonitrile was added, and the reaction was initiated with ~5 mL of 1 M $NH_4HCO_3$ in $H_2O$. The reaction was allowed to proceed for ~30-60 min at RT, and quenched with ~500 ul of the 1M Cysteine hydrochloride (Sigma) once the reaction had completed (judged by MALDI). Following lyophilisation, the modified peptide was purified in a Gemini C18 column (Phenomenex) using water/acetonitrile with 0.1% trifluoroacetic acid as mobile phase. Pure fractions containing the correct cyclised material were pooled, lyophilised and kept at −20° C. for storage.

All amino acids, unless noted otherwise, were used in the L-configurations.

Preparation of Bicyclic Peptide Drug Conjugates BDC-1 to BDC-5

The synthesis of Bicyclic Peptide Drug Conjugates BDC-1 to BDC-5 listed in Tables 11 were performed using the protocol disclosed in WO 2016/067035.

Activated bicycle peptides with formula (C) and (D):

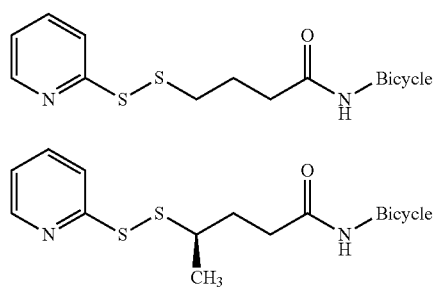

were synthesised by reacting the free amino group of the bicycle precursors with, respectively, SPP (N-succinimidyl 4-(2-pyridyldithio)pentanoate, Annova Chem) and SPDB (N-succinimidyl 3-(2-pyridyldithio)propionate, Annova Chem) in DMSO. Concentrations of bicycle precursors were 10 mM or higher, with a 1.3-fold excess of SPP or SPDB, and a 20-fold excess of diisopropylethylamine, at room temperature. The reaction was judged complete after 1 hour, as judged by LCMS. Purification was performed by reverse phase as described above. Appropriate fractions were lyophilised.

Activated bicycle peptides with formula (C) and (D) were disulphide exchanged with 1.15 equivalents of DM1 (as the free thiol), in semi aqueous conditions (50% dimethylacetamide and 50% 100 mM sodium acetate pH 5.0 supplemented with 2 mM EDTA) for 21 hours at room temperature under a nitrogen gas blanket. Concentrations of activated bicycle peptides with structure C and D in the reaction were at 10 mM or higher.

This was followed by standard reverse phase purification using a C18 column. Fractions at purity greater than 95% were isolated and lyophilised. The materials did not contain measurable quantities of free toxin.

BIOLOGICAL DATA

1. Fluorescence Polarisation Measurements (a) Direct Binding Assay

Peptides with a fluorescent tag (either fluorescein, SIGMA or Alexa Fluor488™, Fisher Scientific) were diluted to 2.5 nM in PBS with 0.01% tween 20 or 50 mM HEPES with 100 mM NaCl and 0.01% tween pH 7.4 (both referred to as assay buffer). This was combined with a titration of protein in the same assay buffer as the peptide to give 1 nM peptide in a total volume of 25 μL in a black walled and bottomed low bind low volume 384 well plates, typically 5 μL assay buffer, 10 μL protein (Table 1) then 10 μL fluorescent peptide. One in two serial dilutions were used to give 12 different concentrations with top concentrations ranging from 500 nM for known high affinity binders to 10 μM for low affinity binders and selectivity assays. Measurements were conducted on a BMG PHERAstar FS equipped with an "FP 485 520 520" optic module which excites at 485 nm and detects parallel and perpendicular emission at 520 nm. The PHERAstar FS was set at 25° C. with 200 flashes per well and a positioning delay of 0.1 second, with each well measured at 5 to 10 minute intervals for 60 minutes. The gain used for analysis was determined for each tracer at the end of the 60 minutes where there was no protein in the well. Data was analysed using Systat Sigmaplot version 12.0. mP values were fit to a user defined quadratic equation to generate a Kd value: f=ymin+(ymax−ymin)/Lig*((x+Lig+Kd)/2-sqrt((((x+Lig+Kd)/2)^2)-(Lig*x))). "Lig" was a defined value of the concentration of tracer used.

(b) Competition Binding Assay

Peptides without a fluorescent tag were tested in competition with a peptide with a fluorescent tag and a known Kd (Table 2). Peptides were diluted to an appropriate concentration in assay buffer as described in the direct binding assay with a maximum of 5% DMSO, then serially diluted 1 in 2. Five μL of diluted peptide was added to the plate followed by 10 μL of human or mouse EphA2 (Table 1) at a fixed concentration which was dependent on the fluorescent peptide used (Table 2), then 10 μL fluorescent peptide added. Measurements were conducted as for the direct binding assay, however the gain was determined prior to the first measurement. Data analysis was in Systat Sigmaplot version 12.0 where the mP values were fit to a user defined cubic equation to generate a Ki value:

f=ymin+(ymax−ymin)/Lig((Lig*((2*((Klig+Kcomp+Lig+Comp−Prot*c)^2−3*(Kcomp*(Lig−Prot*c)+Klig*(Comp−Prot*c)+Klig*Kcomp))^0.5*COS(ARCCOS((−2*(Klig+Kcomp+Lig+Comp−Prot*c)^3+9*(Klig+Kcomp+Lig+Comp−Prot*c)*(Kcomp*(Lig−Prot*c)+Klig*(Comp−Prot*c)+Klig*Kcomp)−27*(−1*Klig*Kcomp*Prot*c))/(2*((((Klig+Kcomp+Lig+Comp−Prot*c)^2−3*(Kcomp*(Lig−Prot*c)+Klig*(Comp−Prot*c)+Klig*Kcomp))^3)^0.5)))/3))−(Klig+Kcomp+Lig+Comp−Prot*c)))/((3*Klig)+((2*((Klig+Kcomp+Lig+Comp−Prot*c)^2−3*(Kcomp*(Lig−Prot*c)+Klig*(Comp−Prot*c)+Klig*Kcomp))^0.5*COS(ARCCOS((−2*(Klig+Kcomp+Lig+Comp−Prot*c)^3+9*(Klig+Kcomp+Lig+Comp−Prot*c)*(Kcomp*(Lig−Prot*c)+Klig*(Comp−Prot*c)+Klig*Kcomp)−27*(−1*Klig*Kcomp*Prot*c))/(2*(MKlig+Kcomp+Lig+Comp−Prot*c)^2−3*(Kcomp*(Lig−Prot*c)+Klig*(Comp−Prot*c)+Klig*Kcomp))^3)^0.5)))/3))−(Klig+Kcomp+Lig+Comp−Prot*c)))).

"Lig", "KLig" and "Prot" were all defined values relating to: fluorescent peptide concentration, the Kd of the fluorescent peptide and EphA2 concentration respectively.

TABLE 1

Ephrin receptors and source

| Receptor (domain) | Species | Format/tag | Supplier | Catalogue number |
|---|---|---|---|---|
| EphA1 (Ecto) | Human | Fc fusion | R&D systems | 7146-A1 |
| EphA2 (Ecto) | Human | C-terminal polyHis | R&D systems | 3035-A2 |
| EphA2 (Ecto) | Human | C-terminal polyHis | In-house | N/A |
| EphA2 (Ecto) | Mouse | Fc fusion | R&D Systems | 639-A2 |
| EphA2 (Ecto) | Mouse | C-terminal polyHis | Sino Biological | 50586-M08H |
| EphA2 (ligand binding) | Rat | C-terminal polyHis | In-house | N/A |
| EphA2 (ligand binding) | Dog | C-terminal polyHis | In-house | N/A |
| EphA3 (Ecto) | Human | Fc fusion | R&D systems | 6444-A3 |
| EphA3 (Ecto) | Human | N-terminal polyHis | In-house | N/A |
| EphA3 (Ecto) | Rat | C-terminal polyHis | Sino Biological | 80465-R08H |
| EphA4 (Ecto) | Human | Fc fusion | R&D systems | 6827-A4 |
| EphA4 (Ecto) | Human | C-terminal polyHis | Sino Biological | 11314-H08H |
| EphA4 (Ecto) | Rat | C-terminal polyHis | Sino Biological | 80123-R08H |
| EphA6 (Ecto) | Human | Fc fusion | R&D systems | 5606-A6 |
| EphA7 (Ecto) | Human | Fc fusion | R&D systems | 6756-A7 |
| EphB1 (Ecto) | Rat | Fc fusion | R&D systems | 1596-B1 |
| EphB4 (Ecto) | human | C-terminal polyHis | R&D systems | 3038-B4 |

TABLE 2

Final concentrations of fluorescent peptide and EphA2 as used with Competition Binding Assays

| Fluorescent peptide | Concentration of fluorescent peptide (nM) | Concentration of Human EphA2 (nM) | Concentration of Mouse EphA2 (nM) |
|---|---|---|---|
| Compound 1 | 1 | 300 | |
| Compound 12 | 10 | 75 | |
| Compound 66 | 1 | 30 | |
| Compound 18 | 0.8 (human) 1 (mouse) | 2.4 | 50 |

The peptide ligands of the invention were tested in the above mentioned assays and the results are shown in Tables 3-12:

TABLE 3

Biological Assay Data for TBMB Peptide Ligands of the Invention (Direct Binding Assay)

| Bicycle Compound Number | Sequence | $K_D$, nm ± 95% CI Human EphA2 | Mouse EphA2 |
|---|---|---|---|
| 1 | ACMNDWLCSLGVVTCA-Sar$_6$-K(FI) ((SEQ ID NO: 1-Sar$_6$-K(FI)) | 107.58 ± 40.83 | 301 n = 1 |
| 2 | (AF488-G-Sar$_{10}$-ACMNDWLCSLGWTC (AF488-G-Sar$_{10}$-SEQ ID NO: 2) | 326 n = 1 | |
| 3 | ACMNDWLCELGWTCA-Sar$_6$-K(FI) ((SEQ ID NO: 3-Sar$_6$-K(FI)) | 121.48 ± 50.27 | |
| 4 | ACTRQGIWCALGFEPCA-Sar$_6$-K(FI) ((SEQ ID NO: 4)-Sar$_6$-K(FI)) | 163.5 ± 22.54 | |
| 5 | ACMNDWLCTLGWSCA-Sar$_6$-K(FI) ((SEQ ID NO: 5)-Sar$_6$-K(FI)) | 142.5 ± 83.3 | |
| 6 | ACMNDWLCQLGWTCA-Sar$_6$-K(FI) ((SEQ ID NO: 6)-Sar$_6$-K(FI)) | 4.25 ± 4.8 | |
| 7 | ACMNDWLCTLGWTCA-Sar$_6$-K(FI) ((SEQ ID NO: 7)-Sar$_6$-K(FI)) | 74.35 ± 15.97 | |

TABLE 3-continued

Biological Assay Data for TBMB Peptide Ligands of the Invention (Direct Binding Assay)

| Bicycle Compound Number | Sequence | $K_D$, nm ± 95% CI Human EphA2 | Mouse EphA2 |
|---|---|---|---|
| 8 | ACMNDWLCDLGWRCA-Sar$_6$-K(FI) ((SEQ ID NO: 8)-Sar$_6$-K(FI)) | 118.5 ± 22.54 | |
| 9 | ACMNDWLCELGWSCA-Sar$_6$-K(FI) ((SEQ ID NO: 9)-Sar$_6$-K(FI)) | 137.5 ± 49.98 | |
| 10 | ACRVSPEYCPFGPVWCAGAAA-Sar$_6$-K(FI) ((SEQ ID NO: 10)-Sar6-K(FI)) | 135.13 ± 59.02 | |
| 11 | FI-G-Sar$_5$-ACPWGPAWCPVHGKTCA (FI-G-Sar$_5$-(SEQ ID NO: 11)) | 263 ± 213.64 | |
| 12 | FI-G-Sar$_5$-ACPWGPAWCPVNRPGCA (FI-G-Sar$_5$-(SEQ ID NO: 12)) | 27.78 ± 8.35 | |
| 13 | Ac-ACPWGPAWCPVNRPGCAGAAA-K(FI) (Ac-(SEQ ID NO: 13)-K(FI)) | 29 ± 2.55 | |
| 14 | AF488-G-Sar$_{10}$-ACPWGPAWCPVNRPGCA (AF488-G-Sar$_{10}$-(SEQ ID NO: 12)) | 38 n = 1 | |
| 15 | FI-G-Sar$_5$-ACPWGPMWCPVNRPGCA (FI-G-Sar$_5$-(SEQ ID NO: 14)) | 12.6 ± 2.55 | |
| 16 | FI-G-Sar$_5$-ACPWGPNWCPVNRPGCA (FI-G-Sar$_5$-(SEQ ID NO: 15)) | 11.5 ± 1.76 | |
| 17 | FI-G-Sar$_5$-AGEMACPWGPFWCPVNRPGCA (FI-G-Sar$_5$-(SEQ ID NO: 16)) | 3.85 ± 0.1 | |
| 18 | FI-G-Sar$_5$-ADVTCPWGPFWCPVNRPGCA (FI-G-Sar$_5$-(SEQ ID NO: 17)) | 0.93 ± 0.23 | 4.02 ± 2 |
| 19 | FI-G-Sar$_5$-ADVRTCPWGPFWCPVNRPGCA (FI-G-Sar$_5$-(SEQ ID NO: 18)) | 4.74 ± 0.51 | |
| 20 | FI-G-Sar$_5$-ANDVTCPWGPFWCPVNRPGCA (FI-G-Sar$_5$-(SEQ ID NO: 19)) | 2.35 ± 0.49 | |
| 21 | ACVPQGIWCALQFEPCA-Sar$_6$-K(FI) ((SEQ ID NO: 20)-Sar$_6$-K(FI)) | 59.5 ± 12.78 | |
| 22 | ACQKQGLWCALGFEPCA-Sar$_6$-K(FI) ((SEQ ID NO: 21)-Sar$_6$-K(FI)) | 289 ± 74.51 | |
| 23 | ACLVNDDCFYMGLCA-Sar$_6$-K(FI) ((SEQ ID NO: 22)-Sar$_6$-K(FI)) | 109.38 ± 20.75 | |

TABLE 5

Biological Assay Data for TBMB Peptide Ligands of the Invention (Competition Binding Assay)

| Bicycle Compound Number | Sequence | Human EphA2 ($K_i$, nM ± 95% CI) Fluorescent Peptide | | | |
|---|---|---|---|---|---|
| | | Compound 66 | Compound 1 | Compound 12 | Compound 18 |
| 24 | ACMNDWLCSLGWTCA (SEQ ID NO: 1) | 82.34 ± 12.8 | | | |
| 25 | Ac-CANDWLCSLGWTC (Ac-(SEQ ID NO: 23)) | 328 n = 1 | | | |
| 26 | Ac-CMNDWLCALGWTC (Ac-(SEQ ID NO: 24)) | 71.6 ± 3.33 | | | |
| 27 | Ac-CMNDWLCSAGWTC (Ac-(SEQ ID NO: 25)) | 356 n = 1 | | | |
| 28 | ACMNDWLCQLGWKCA (SEQ ID NO: 26) | 113 n = 1 | | | |
| 29 | ACMNDWLCELGWTCA (SEQ ID NO: 3) | 134.5 ± 32.34 | | | |
| 30 | ACMNDWLCQLGWTCA (SEQ ID NO: 6) | 56.05 ± 3.23 | | | |
| 31 | ACTQNDWLCSLGWTCA (SEQ ID NO: 27) | 151.65 ± 161.4 | | | |
| 32 | ACRNIPTMCPFGPVWCA (SEQ ID NO: 28) | | 83.4 n = 1 | | |

TABLE 5-continued

Biological Assay Data for TBMB Peptide Ligands
of the Invention (Competition Binding Assay)

| Bicycle Compound Number | Sequence | Human EphA2 ($K_i$, nM ± 95% CI) Fluorescent Peptide | | | |
|---|---|---|---|---|---|
| | | Compound 66 | Compound 1 | Compound 12 | Compound 18 |
| 33 | ACRVSPEYCPFGPVWCA (SEQ ID NO: 29) | 78.53 ± 35.61 | | | |
| 34 | ACRVSPEYCPFGPVWCAGAAA (SEQ ID NO: 10) | 77.4 ± 8.95 | | | |
| 35 | ACRVSPEYCPFGPTWCA (SEQ ID NO: 30) | 43.2 ± 13.33 | | | |
| 36 | ACRVSPEYCPFGPSWCA (SEQ ID NO: 31) | 40.5 ± 5.88 | | | |
| 37 | ACRVSPEYCPFGPEWCA (SEQ ID NO: 32) | 61.25 ± 41.85 | | | |
| 38 | ACRVSPEYCPFGPYWCA (SEQ ID NO: 33) | 26.53 ± 16.92 | | | |
| 39 | ACRVSPEYCPFGPLWCA (SEQ ID NO: 34) | 32.11 ± 10.28 | | | |
| 40 | ACRVSPEYCPFGPDWCA (SEQ ID NO: 35) | 55.4 ± 9.41 | | | |
| 41 | ACPWGPAWCPVHGKTCA (SEQ ID NO: 11) | | 263 n = 1 | | |
| 42 | ACPWGPAWCPVRDTNCA (SEQ ID NO: 36) | 316 n = 1 | | | |
| 43 | ACPWGPAWCPVNGARCA (SEQ ID NO: 37) | 430 n = 1 | | | |
| 44 | ACPWGPAWCPVNRPGCA (SEQ ID NO: 12) | 191.22 ± 29.47 | 164 n = 1 | 128.45 ± 28.21 | |
| 45 | ACPWGPAWCPVNRPGCAGAAA (SEQ ID NO: 13) | 117.13 ± 17.96 | | 99.15 ± 48.71 | |
| 46 | ACPWGPMWCPVNRPGCA (SEQ ID NO: 14) | 95.75 ± 29.89 | | | |
| 47 | ACPWGPNWCPVNRPGCA (SEQ ID NO: 15) | 78.35 ± 12.64 | | | |
| 48 | ACPWGPAWCPVRNPCA (SEQ ID NO: 38) | 284 ± 47.04 | | | |
| 49 | ACPWGPAWCPVSRVCA (SEQ ID NO: 39) | 428 ± 99.96 | | | |
| 50 | ACPWGPAWCPVRSCA (SEQ ID NO: 40) | 314 ± 248.92 | | | |
| 51 | ACPWGPAWCPVKPTCA (SEQ ID NO: 41) | 318.5 ± 255.78 | | | |
| 52 | ACPWGPAWCPVNRNGCA (SEQ ID NO: 42) | 168 ± 72.52 | | | |
| 53 | AGEMACPWGPFWCPVNRPGCA (SEQ ID NO: 16) | 6 ± 5.54 | | | 12.33 ± 2 |
| 54 | AVHIPCPWGPSWCPVNRPGCA (SEQ ID NO: 43) | 5.17 ± 2.76 | | | 5.13 ± 1.52 |
| 55 | AEGLPCPWGPFWCPVNRPGCA (SEQ ID NO: 44) | 6.15 ± 3.43 | | | 11.3 ± 2.04 |
| 56 | ADHACPWGPFWCPVNRPGCA (SEQ ID NO: 45) | 5.87 ± 5.09 | | | 14.43 ± 6.28 |

TABLE 5-continued

Biological Assay Data for TBMB Peptide Ligands of the Invention (Competition Binding Assay)

| Bicycle Compound Number | Sequence | Human EphA2 ($K_i$, nM ± 95% CI) Fluroescent Peptide | | | |
|---|---|---|---|---|---|
| | | Compound 66 | Compound 1 | Compound 12 | Compound 18 |
| 57 | ADVHCPWGPFWCPVNRPGCA (SEQ ID NO: 46) | 1.2 n = 1 | | | 0.48 ± 0.15 |
| 58 | ADVTCPWGPFWCPVNRPGCA (SEQ ID NO: 17) | 2.65 ± 1.08 | | | 1.35 ± 0.23 |
| 59 | AHDVPCPWGPFWCPVNRPGCA (SEQ ID NO: 47) | | | | 0.54 ± 0.14 |
| 60 | ADVRTCPWGPFWCPVNRPGCA (SEQ ID NO: 18) | 2.5 n = 1 | | | 12.63 ± 1.29 |
| 61 | ANDVTCPWGPFWCPVNRPGCA (SEQ ID NO: 19) | 7.3 n = 1 | | | 2.93 ± 0.07 |
| 62 | ARDDPCPWGPFWCPVNRPGCA (SEQ ID NO: 48) | 27.96 ± 16.74 | | | 16.13 ± 0.8 |
| 63 | ACVPQGIWCALQFEPCA (SEQ ID NO: 20) | 82.45 ± 27.07 | 144 n = 1 | 92.2 ± 21.17 | |
| 64 | ACTTGSIWCALQFEPCA (SEQ ID NO: 49) | 63.4 n = 1 | | 410 n = 1 | |
| 65 | ACVPQGIWCALRYEPCA (SEQ ID NO: 50) | 293 n = 1 | | 229 n = 1 | |

TABLE 5

Biological Assay Data for TBMB Peptide Ligands of the Invention (Direct Binding Assay)

| Bicycle Compound Number | Sequence | $K_D$, nM ± 95% CI | |
|---|---|---|---|
| | | Human EphA2 | Mouse EphA2 |
| 66 | Fl-G-Sar$_5$-ACPWGPFWCPVNRPGCA (Fl-G-Sar$_5$-(SEQ ID NO: 51)) | 8.45 ± 0.4 | 22 n = 1 |
| 67 | AlexaFluor488-G-Sar$_5$-ACPWGPFWCPVNRPGC (AlexaFluor488-G-Sar$_5$-(SEQ ID NO: 52)) | 15.03 ± 1.72 | 51.8 ± 6.27 |
| 68 | AlexaFluor488-(β-Ala)-Sar$_{10}$-ACPWGPFWCPVNRPGC (AlexaFluor488-((β-Ala)-Sar$_{10}$-(SEQ ID NO: 52)) | 15.37 ± 2.87 | 23.4 n = 1 |

TABLE 6

Biological Assay Data for TBMB Peptide Ligands of the Invention (Competition Binding Assay)

| Bicycle Compound Number | Sequence | Ki, nM ± 95% CI Human EphA2 Fluorescent Peptide | |
|---|---|---|---|
| | | Compound 18 | Compound 66 |
| 69 | ACPWGPFWCPVNRPGCA (SEQ ID NO: 51) | 106.75 ± 44.25 | 70.08 ± 8.01 |
| 70 | Sar$_2$-ACPWGPFWCPVNRPGC (Sar$_2$-(SEQ ID NO: 52)) | 51.81 ± 21.75 | 20.45 ± 12.84 |
| 71 | Ac-Sar$_2$-ACPWGPFWCPVNRPGC (Ac-Sar$_2$-(SEQ ID NO: 52)) | 11.87 ± 7.51 | |
| 72 | (β-Ala)-Sar$_{10}$-ACPWGPFWCPVNRPGC ((β-Ala)-Sar$_{10}$-(SEQ ID NO: 52)) | 29.1 ± 5.08 | 20.98 ± 2.18 |
| 73 | Sar$_2$-AC(HyP)WGPFWCPVNRPGC (Sar$_2$-(SEQ ID NO: 53)) | 47.6 ± 18.42 | 247.5 ± 18.62 |
| 74 | Sar$_2$-AC(Aib)WGPFWCPVNRPGC (Sar$_2$-(SEQ ID NO: 54)) | | 138.9 ± 88.79 |

TABLE 6-continued

Biological Assay Data for TBMB Peptide Ligands of the Invention (Competition Binding Assay)

| Bicycle Compound Number | Sequence | Ki, nM ± 95% CI Human EphA2 Fluorescent Peptide | |
|---|---|---|---|
| | | Compound 18 | Compound 66 |
| 75 | Sar$_2$-AC(4FlPro)WGPFWCPVNRPGC (Sar$_2$-(SEQ ID NO: 55)) | | 399.67 ± 90.63 |
| 76 | Sar$_2$-ACP(1Nal)GPFWCPVNRPGC (Sar$_2$-(SEQ ID NO: 56)) | 3.5 ± 1.96 | 16.7 ± 9.68 |
| 77 | Sar$_2$-ACP(2Nal)GPFWCPVNRPGC (Sar$_2$-(SEQ ID NO: 57)) | | 458.33 ± 222.44 |
| 78 | Sar$_2$-ACPWG(Aze)FWCPVNRPGC (Sar$_2$-(SEQ ID NO: 58)) | | 403.5 ± 12.74 |
| 79 | Sar$_2$-ACPWG(HyP)FWCPVNRPGC (Sar$_2$-(SEQ ID NO: 59)) | | 131 ± 22.97 |
| 80 | Sar$_2$-ACPWG(Aib)FWCPVNRPGC (Sar$_2$-(SEQ ID NO: 60)) | 120.5 ± 81.34 | 186.73 ± 94.37 |
| 81 | Sar$_2$-ACPWG(4FlPro)FWCPVNRPGC (Sar$_2$-(SEQ ID NO: 61)) | | 294 ± 99.6 |
| 82 | Sar$_2$-ACPWG(Pip)FWCPVNRPGC (Sar$_2$-(SEQ ID NO: 62)) | | 497.33 ± 223.62 |
| 83 | Sar$_2$-ACPWGPAWCPVNRPGC (Sar$_2$-(SEQ ID NO: 63)) | 199 n = 1 | 287.5 ± 197.95 |
| 84 | Sar$_2$-ACPWGP(4Pal)WCPVNRPGC (Sar$_2$-(SEQ ID NO: 64)) | 33.5 ± 0.98 | 81.47 ± 68.95 |
| 85 | Sar$_2$-ACPWGP(4BrPhe)WCPVNRPGC (Sar$_2$-(SEQ ID NO: 65)) | | 174.5 ± 20.58 |
| 86 | Sar$_2$-ACPWGP(4MeOPhe)WCPVNRPGC (Sar$_2$-(SEQ ID NO: 66)) | | 274.5 ± 36.26 |
| 87 | Sar$_2$-ACPWGP(HPhe)WCPVNRPGC (Sar$_2$-(SEQ ID NO: 67)) | 162 n = 1 | 281.2 ± 154.82 |
| 88 | Sar$_2$-ACPWGP(4,4-BPA)WCPVNRPGC (Sar$_2$-(SEQ ID NO: 68)) | | 182.67 ± 99.5 |
| 89 | Sar$_2$-ACPWGP(NO2Phe5)WCPVNRPGC (Sar$_2$-(SEQ ID NO: 69)) | | 289.5 ± 93.1 |
| 90 | Sar$_2$-ACPWGP(3,4-DCPhe)WCPVNRPGC (Sar$_2$-(SEQ ID NO: 70)) | | 361 ± 25.48 |
| 91 | Sar$_2$-ACPWGPYWCPVNRPGC (Sar$_2$-(SEQ ID NO: 71)) | | 137.63 ± 104.2 |
| 92 | Sar$_2$-ACPWGP(3Pal)WCPVNRPGC (Sar$_2$-(SEQ ID NO: 72)) | | 165 ± 27.44 |
| 93 | Sar$_2$-ACPWGP(Phg)WCPVNRPGC (Sar$_2$-(SEQ ID NO: 73)) | | 411.5 ± 128.38 |
| 94 | Sar$_2$-ACPWGP(1Nal)WCPVNRPGC (Sar$_2$-(SEQ ID NO: 74)) | | 196.5 ± 6.86 |
| 95 | Sar$_2$-ACPWGP(2Nal)WCPVNRPGC (Sar$_2$-(SEQ ID NO: 75)) | | 362.5 ± 110.74 |
| 96 | Sar$_2$-ACPWGPF(1Nal)CPVNRPGC (Sar$_2$-(SEQ ID NO: 76)) | 31.3 ± 24.11 | 68.13 ± 35.66 |
| 97 | Sar$_2$-ACPWGPFWC(Aze)VNRPGC (Sar$_2$-(SEQ ID NO: 77)) | | 286 ± 109.76 |
| 98 | Sar$_2$-ACPWGPFWC(HyP)VNRPGC (Sar$_2$-(SEQ ID NO: 78)) | | 163.33 ± 38.41 |
| 99 | Sar$_2$-ACPWGPFWC(4FlPro)VNRPGC (Sar$_2$-(SEQ ID NO: 79)) | | 269.5 ± 6.86 |
| 100 | Sar$_2$-ACPWGPFWCP(tBuGly)NRPGC (Sar$_2$-(SEQ ID NO: 80)) | 58.3 ± 50.37 | 112.45 ± 73.38 |
| 101 | Sar$_2$-ACPWGPFWCPVARPGC (Sar$_2$-(SEQ ID NO: 81)) | 293 n = 1 | 265 ± 235.04 |
| 102 | Sar$_2$-ACPWGPFWCPV(D-Ala)RPGC (Sar$_2$-(SEQ ID NO: 82)) | 317 ± 168.56 | 311.67 ± 195.55 |
| 103 | Sar$_2$-ACPWGPFWCPVN(HArg)PGC (Sar$_2$-(SEQ ID NO: 83)) | 126 ± 9.8 | 169.43 ± 94.28 |
| 104 | Sar$_2$-ACPWGPFWCPVNRAGC (Sar$_2$-(SEQ ID NO: 84)) | 124 n = 1 | 193.67 ± 112.76 |
| 105 | Sar$_2$-ACPWGPFWCPVNR(D-Ala)GC (Sar$_2$-(SEQ ID NO: 85)) | | 470.67 ± 221.53 |
| 106 | Sar$_2$-ACPWGPFWCPVNR(Aze)GC (Sar$_2$-(SEQ ID NO: 86)) | | 155 ± 47.04 |
| 107 | Sar$_2$-ACPWGPFWCPVNR(HyP)GC (Sar$_2$-(SEQ ID NO: 87)) | 48.7 n = 1 | 85.83 ± 57.98 |
| 108 | Sar$_2$-ACPWGPFWCPVNR(Pip)GC (Sar$_2$-(SEQ ID NO: 88)) | | 374.5 ± 12.74 |
| 109 | Sar$_2$-ACPWGPFWCPVNR(4FlPro)GC (Sar$_2$-(SEQ ID NO: 89)) | | 184.5 ± 20.58 |
| 110 | Sar$_2$-ACPWGPFWCPVNR(Aib)GC (Sar$_2$-(SEQ ID NO: 90)) | 75 ± 13.72 | 139.53 ± 103.98 |

TABLE 6-continued

Biological Assay Data for TBMB Peptide Ligands of the Invention (Competition Binding Assay)

| Bicycle Compound Number | Sequence | Ki, nM ± 95% CI Human EphA2 Fluorescent Peptide | |
|---|---|---|---|
| | | Compound 18 | Compound 66 |
| 111 | Sar$_2$-ACPWGPFWCPVNRPAC (Sar$_2$-(SEQ ID NO: 91)) | 108 n = 1 | 237.5 ± 164.92 |
| 112 | Sar$_2$-ACPWGPFWCPVNRP(D-Ala)C (Sar$_2$-(SEQ ID NO: 92)) | 89 ± 15.68 | |
| 113 | Sar$_2$-AC(Aib)(1Nal2)GPFWCPVNRPGC (Sar$_2$-(SEQ ID NO: 93)) | 10 n = 1 | 6.6 n = 1 |
| 114 | Sar$_2$-AC(Aib)WGPF(1Nal)CPVNRPGC (Sar$_2$-(SEQ ID NO: 94)) | 21 n = 1 | 43 n = 1 |
| 115 | Sar$_2$-ACP(1Nal)GPFWCPV(D-Ala)RPGC (Sar$_2$-(SEQ ID NO: 95)) | 12.5 ± 0.98 | 1.64 ± 2.48 |
| 116 | Sar$_2$-ACP(1Nal)GPFWCPVNRP(D-Ala)C (Sar$_2$-(SEQ ID NO: 96)) | 2.95 ± 1.67 | 3.2 n = 1 |
| 117 | Sar$_2$-ACPWGPF(1Nal)CPV(D-Ala)RPGC (Sar$_2$-(SEQ ID NO: 97)) | 53 n = 1 | 75 n = 1 |
| 118 | Sar$_2$-ACPWGPF(1Nal)CPVNRP(D-Ala)C (Sar$_2$-(SEQ ID NO: 98)) | 37 n = 1 | 18 ± 13.72 |
| 119 | Sar$_2$-ACP(1Nal)G(Aib)FWCPVNRPGC (Sar$_2$-(SEQ ID NO: 99)) | 21 n = 1 | 8.4 n = 1 |
| 120 | Sar$_2$-ACP(1Nal)GPF(1Nal)CPVNRPGC (Sar$_2$-(SEQ ID NO: 100)) | 1.4 ± 0.39 | 0.98 n = 1 |
| 121 | Sar$_2$-ACP(1Nal)GPFWCP(tBuGly)NRPGC (Sar$_2$-(SEQ ID NO: 101)) | 3.65 ± 0.29 | 2 n = 1 |
| 122 | Sar$_2$-ACP(1Nal)GPFWCPVN(HArg)PGC (Sar$_2$-(SEQ ID NO: 102)) | 9.55 ± 0.69 | 8 n = 1 |
| 123 | Sar$_2$-ACPWG(Aib)F(1Nal)CPVNRPGC (Sar$_2$-(SEQ ID NO: 103)) | 63 n = 1 | 46 n = 1 |
| 124 | Sar$_2$-AC(Aib)(1Nal)GPFWCPV(D-Ala)RPGC (Sar$_2$-(SEQ ID NO: 104)) | 26 n = 1 | 2.5 n = 1 |
| 125 | Sar$_2$-AC(Aib)(1Nal)GPFWCPVNRP(D-Ala)C (Sar$_2$-(SEQ ID NO: 105)) | 6.4 ± 0.78 | 0.61 ± 0.96 |
| 126 | Sar$_2$-ACP(1Nal)G(Aib)FWCP(tBuGly)NRPGC (Sar$_2$-(SEQ ID NO: 106)) | 15 n = 1 | 19 n = 1 |
| 127 | Sar$_2$-ACP(1Nal)G(Aib)FWCPV(D-Ala)RPGC (Sar$_2$-(SEQ ID NO: 107)) | 40 n = 1 | 33 n = 1 |
| 128 | Sar$_2$-ACP(1Nal)G(Aib)FWCPVNRP(D-Ala)C (Sar$_2$-(SEQ ID NO: 108)) | 15 n = 1 | 16 n = 1 |
| 129 | Sar$_2$-ACP(1Nal)GPFWCP(tBuGly)(D-Ala)RPGC (Sar$_2$-(SEQ ID NO: 109)) | 23 n = 1 | 15 n = 1 |
| 130 | Sar$_2$-ACP(1Nal)GPFWCP(tBuGly)N(HArg)PGC (Sar$_2$-(SEQ ID NO: 110)) | 0.29 ± 0.34 | |
| 131 | Sar$_2$-ACP(1Nal)GPFWCP(tBuGly)NR(Aib)GC (Sar$_2$-(SEQ ID NO: 111)) | 11 n = 1 | 6.8 n = 1 |
| 132 | Sar$_2$-ACP(1Nal)GPFWCP(tBuGly)NRP(D-Ala)C (Sar$_2$-(SEQ ID NO: 112)) | 7.7 ± 1.96 | 8.7 n = 1 |
| 133 | Sar$_2$-ACP(1Nal)GPFWCPV(D-Ala)(HArg)PGC (Sar$_2$-(SEQ ID NO: 113)) | 14 n = 1 | 3.7 n = 1 |
| 134 | Sar$_2$-ACP(1Nal)GPFWCPVN(HArg)P(D-Ala)C (Sar$_2$-(SEQ ID NO: 114)) | 1.2 n = 1 | 6.15 ± 0.29 |
| 135 | Sar$_2$-AC(Aib)(1Nal)G(Aib)FWCPVNR(Aib)GC (Sar$_2$-(SEQ ID NO: 115)) | 43 n = 1 | 30 n = 1 |
| 136 | Sar$_2$-ACP(1Nal)G(Aib)FWCP(tBuGly)N(HArg)PGC (Sar$_2$-(SEQ ID NO: 116)) | 23 n = 1 | 15 n = 1 |
| 137 | Sar$_2$-ACP(1Nal)G(Aib)FWCP(tBuGly)NR(Aib)GC (Sar$_2$-(SEQ ID NO: 117)) | 20 n = 1 | 18 n = 1 |
| 138 | Sar$_2$-ACP(1Nal)GPFWCP(tBuGly)N(HArg)(Aib)GC (Sar$_2$-(SEQ ID NO: 118)) | 5.1 n = 1 | |

TABLE 7

Biological Assay Data for TBMB Peptide Ligands of the Invention (Direct Binding Assay)

| Bicycle Compound Number | Sequence | $K_D$, nM ± 95% CI Human EphA2 | Mouse EphA2 |
|---|---|---|---|
| 139 | AF488-(β-Ala)-Sar$_{10}$-H(D-Asp)VPCPWGPFWCPVNRPGCA (AF488-(β-Ala)-Sar$_{10}$-(SEQ ID NO: 119)) | 0.31 ± 0.18 | 0.8 ± 0.54 |
| 140 | AF488-(β-Ala)-Sar$_{10}$-H(D-Asp)VP-C(Aib)(1Nal)G(Aib)F(1Nal)CP(tBuGly)N(HArg)P(D-Asp)C (AF488-(β-Ala)-Sar$_{10}$-(SEQ ID NO: 120)) | 2.05 ± 0.62 | 4.55 ± 1.04 |
| 141 | AF488-(β-Ala)-Sar$_{10}$-H(D-Asp)VP-C(Aib)(1Nal)G(Aib)F(1Nal)CP(tBuGly)NR(Aib)(D-Asp)C (AF488-(β-Ala)-Sar$_{10}$-(SEQ ID NO: 121)) | 2.65 ± 0.64 | 6.5 ± 0.63 |
| 142 | Fl-(β-Ala)-Sar$_{10}$-H(D-Asp)VP-CP(1Nal)G(Aib)F(1Nal)CP(tBuGly)N(HArg)P(D-Asp)C (Fl-(β-Ala)-Sar$_{10}$-(SEQ ID NO: 122)) | 1.7 n = 1 | |
| 143 | AF488-(β-Ala)-Sar$_{10}$-H(D-Asp)VP-CP(1Nal)G(Aib)F(1Nal)CP(tBuGly)N(HArg)P(D-Asp)C(AF488-(β-Ala)-Sar$_{10}$-(SEQ ID NO: 122)) | 1.4 ± 1.46 | 4.69 ± 4.15 |
| 144 | AF488-(β-Ala)-Sar$_{10}$-H(D-Asp)VP-CP(1Nal)G(Aib)F(1Nal)CP(tBuGly)NR(Aib)GC (AF488-(β-Ala)-Sar$_{10}$-(SEQ ID NO: 123)) | 1.04 n = 1 | 2.56 n = 1 |
| 145 | AF488-(β-Ala)-Sar$_{10}$-H(D-Asp)VP-CP(1Nal)G(Aib)F(1Nal)CP(tBuGly)NR(Aib)(D-Asp)C(AF488-(β-Ala)-Sar$_{10}$-(SEQ ID NO: 124)) | 2.17 ± 2.08 | 3.8 ± 0.55 |
| 146 | AF488-(β-Ala)-Sar$_{10}$-H(D-Asp)(C5g)P-C(Aib)(1Nal)G(Aib)F(1Nal)CP(tBuGly)NR(Aib)(D-Asp)C (AF488-(β-Ala)-Sar$_{10}$-(SEQ ID NO: 125)) | 2.19 n = 1 | |
| 147 | AF488-(β-Ala)-Sar$_{10}$-H(D-Asp)(C5g)P-CP(1Nal)G(Aib)F(1Nal)CP(tBuGly)N(HArg)P(D-Asp)C (AF488-(β-Ala)-Sar$_{10}$-(SEQ ID NO: 126)) | 1.07 ± 0.9 | 3.44 ± 1.31 |

TABLE 8

Biological Assay Data for TBMB Peptide Ligands of the Invention (Competition Binding Assay)

| Bicycle Compound Number | Sequence | Ki, nM ± 95% CI Fluorescent peptide Human EphA2 Compound 18 | Mouse EphA2 Compound 18 |
|---|---|---|---|
| 148 | Ac-Sar$_2$-ADVH-CPWGPFWCPVNRPGC (Ac-Sar$_2$-(SEQ ID NO: 127)) | 1.2 ± 0.2 | |
| 149 | ADVH-CP(3,3-DPA)GPFWCPVNRPGCA (SEQ ID NO: 128) | 52.8 ± 11.6 | |
| 150 | ADVH-CP(1Nal)GPFWCPVNRPGCA (SEQ ID NO: 129) | 0.12 ± 0.07 | |
| 151 | ADVH-CPWAPFWCPVNRPGCA (SEQ ID NO: 130) | 393.5 ± 206.78 | |
| 152 | ADVH-CPWGAFWCPVNRPGCA (SEQ ID NO: 131) | 1.8 ± 0.74 | |
| 153 | ADVH-CPWG(Aib)FWCPVNRPGCA (SEQ ID NO: 132) | 0.51 ± 0.29 | |
| 154 | ADVH-CPWGPFWCAPVNRPGCA (SEQ ID NO: 133) | 101.03 ± 33.68 | |
| 155 | ADVH-CPWGPFWCPV(D-Ala)RPGCA (SEQ ID NO: 134) | 2 ± 0.74 | |
| 156 | ADVH-CPWGPFWCPVN(D-Ala)PGCA (SEQ ID NO: 135) | 14.93 ± 2.3 | |
| 157 | Ac-Sar$_2$-ADVT-CPWGPFWCPVNRPGC (Ac-Sar$_2$-(SEQ ID NO: 136)) | 0.91 ± 0.19 | |
| 158 | Ac-Sar$_2$-A(D-Asp)-CPWGPFWCPVNRPGC (Ac-Sar$_2$-(SEQ ID NO: 137)) | 2.05 ± 0.42 | 2.2 ± 0.4 |
| 159 | Ac-Sar$_2$-A(D-Asp)(D-Asp)T-CPWGPFWCPVNRPGC (Ac-Sar$_2$-(SEQ ID NO: 138)) | 2.85 ± 0.49 | |
| 160 | Ac-Sar$_2$-A(D-Asp)(Cba)T-CPWGPFWCPVNRPGC (Ac-Sar$_2$-(SEQ ID NO: 139)) | 2.6 ± 0.11 | |
| 161 | Ac-Sar$_2$-A(D-Asp)(Cpa)T-CPWGPFWCPVNRPGC (Ac-Sar$_2$-(SEQ ID NO: 140)) | 4.44 ± 1.08 | |
| 162 | Ac-Sar$_2$-A(D-Asp)(Cpg)T-CPWGPFWCPVNRPGC (Ac-Sar$_2$-(SEQ ID NO: 141)) | 2.55 ± 0.55 | |
| 163 | Ac-Sar$_2$-A(D-Asp)(C5g)VT-CPWGPFWCPVNRPGC (Ac-Sar$_2$-(SEQ ID NO: 142)) | 1.33 ± 0.27 | 1.74 ± 1.23 |
| 164 | Ac-Sar$_2$-AD(tBuGly)T-CPWGPFWCPVNRPGC (Ac-Sar$_2$-(SEQ ID NO: 143)) | 2.25 ± 0.69 | |
| 165 | Ac-Sar$_2$-A(D-Asp)VT-C(AC3C)WGPFWCPVNRPGC (Ac-Sar$_2$-(SEQ ID NO: 144)) | 185 ± 147 | |
| 166 | Ac-Sar$_2$-A(D-Asp)VT-C(AC4C)WGPFWCPVNRPGC (Ac-Sar$_2$-(SEQ ID NO: 145)) | 76.7 ± 73.11 | |
| 167 | Ac-Sar$_2$-A(D-Asp)VT-C(AC5C)WGPFWCPVNRPGC (Ac-Sar$_2$-(SEQ ID NO: 146)) | 138 n = 1 | |
| 168 | Ac-Sar$_2$-A(D-Asp)VT-C(4BenzyPro)WGPFWCPVNRPGC (Ac-Sar$_2$-(SEQ ID NO: 147)) | 5.03 ± 2.24 | |
| 169 | Ac-Sar$_2$-A(D-Asp)VT-C(4PhenyPro)WGPFWCPVNRPGC (Ac-Sar$_2$-(SEQ ID NO: 148)) | 14.4 ± 7.64 | |

TABLE 8-continued

Biological Assay Data for TBMB Peptide Ligands of the Invention (Competition Binding Assay)

| Bicycle Compound Number | Sequence | Ki, nM ± 95% CI Fluorescent peptide Human EphA2 Compound 18 | Mouse EphA2 Compound 18 |
|---|---|---|---|
| 170 | Ac-Sar$_2$-A(D-Asp)VT-CP(1Nal)GPFWCPVNRPGC (Ac-Sar$_2$-(SEQ ID NO: 149)) | 0.6 ± 0.19 | |
| 171 | Ac-Sar$_2$-A(D-Asp)VT-CPwGP(HArg)WCPVNRPGC (Ac-Sar$_2$-(SEQ ID NO: 150)) | 4.88 ± 2.19 | |
| 172 | Ac-Sar$_2$-A(D-Asp)VT-CPWGPNWCPVNRPGC (Ac-Sar$_2$-(SEQ ID NO: 151)) | 3.96 ± 0.72 | |
| 173 | Ac-Sar$_2$-A(D-Asp)VT-CPWGPAWCPVNRPGC (Ac-Sar$_2$-(SEQ ID NO: 152)) | 6.69 ± 3.49 | |
| 174 | Ac-Sar$_2$-A(D-Asp)VT-CPWGPFWCPLNRPGC (Ac-Sar$_2$-(SEQ ID NO: 153)) | 9.1 ± 1.73 | |
| 175 | Ac-Sar$_2$-A(D-Asp)VT-CPWGPFWCPVNRP(D-Asp)C (Ac-Sar$_2$-(SEQ ID NO: 154)) | 1.78 ± 0.54 | |
| 176 | Ac-Sar$_2$-A(D-Asp)VT-CPWGPFWCPVN(HArg)P(D-Asp)C (Ac-Sar$_2$-(SEQ ID NO: 155)) | 4.89 ± 0.97 | |
| 177 | Ac-Sar$_2$-A(D-Asp)VT-CPWGPFWCPVNR(Aib)(D-Asp)C (Ac-Sar$_2$-(SEQ ID NO: 156)) | 4.43 ± 2.37 | |
| 178 | Ac-Sar$_2$-A(D-Asp)VT-CP(1Nal)G(Aib)FWCPVNR(Aib)GC (Ac-Sar$_2$-(SEQ ID NO: 157)) | 2.4 ± 0.23 | |
| 179 | Ac-Sar$_2$-A(D-Asp)VT-CPWG(Aib)F(1Nal)CPVNR(Aib)GC (Ac-Sar$_2$-(SEQ ID NO: 158)) | 2.94 ± 0.09 | |
| 180 | Ac-Sar$_2$-A(D-Asp)VT-CPWG(Aib)FWCP(tBuGly)NR(Aib)GC (Ac-Sar$_2$-(SEQ ID NO: 159)) | 3.83 ± 0.43 | |
| 181 | Ac-Sar$_2$-A(D-Asp)VT-CP(1Nal)G(Aib)F(1Nal)CPVNR(Aib)GC (Ac-Sar$_2$-(SEQ ID NO: 160)) | 1.37 ± 0.41 | |
| 182 | Ac-Sar$_2$-A(D-Asp)VT-CP(1Nal)G(Aib)F(1Nal)CP(tBuGly)N(HArg)PGC (Ac-Sar$_2$-(SEQ ID NO: 161)) | 1.16 ± 0.39 | |
| 183 | Ac-Sar$_2$-A(D-Asp)VT-CP(1Nal)G(Aib)F(1Nal)CP(tBuGly)N(HArg)(Aib)GC (Ac-Sar$_2$-(SEQ ID NO: 162)) | 1.02 ± 0.41 | |
| 184 | Ac-Sar$_2$-A(D-Asp)VT-CP(1Nal)G(Aib)F(1Nal)CP(tBuGly)NR(Aib)GC (Ac-Sar$_2$-P(D-Asp)C (SEQ ID NO: 163)) | 1.19 ± 0.29 | |
| 185 | (D-Asp)VT-CPWGPFWCPVNRPGC (SEQ ID NO: 164) | 2.17 ± 0.73 | |
| 186 | (D-Asp)VT-CP(1Nal)G(Aib)F(1Nal)CP(tBuGly)NR(Aib)GC (SEQ ID NO: 165) | 1.34 ± 0.18 | |
| 187 | AHDVP-CP(1Nal)GPFWCPVNRPGCA (SEQ ID NO: 166) | 0.32 ± 0.03 | |
| 188 | AHDVP-CP(1Nal)GPFWCPVNRPGC (SEQ ID NO: 167) | 1.45 ± 0.1 | |
| 189 | AHDVP-CPWGPF(1Nal)CPVNRPGC (SEQ ID NO: 168) | 1.3 ± 0.2 | |

TABLE 8-continued

Biological Assay Data for TBMB Peptide Ligands of the Invention (Competition Binding Assay)

| Bicycle Compound Number | Sequence | Ki, nM ± 95% CI Fluorescent peptide | |
|---|---|---|---|
| | | Human EphA2 Compound 18 | Mouse EphA2 Compound 18 |
| 190 | AHDVP-CP(1Nal)GPFWCP(tBuGly)NRPGC (SEQ ID NO: 169) | 0.7 ± 0.4 | |
| 191 | AHDVP-CP(1Nal)G(Aib)FWCP(tBuGly)N(HArg)PGC (SEQ ID NO: 170) | 3.1 ± 0.68 | |
| 192 | AHDVP-CP(1Nal)G(Aib)FWCP(tBuGly)NR(Aib)GC (SEQ ID NO: 171) | 1.75 ± 0.1 | |
| 193 | Ac-Sar$_2$-AHDVP-CPWGPFWCPVNRPGC (Ac-Sar$_2$- (SEQ ID NO: 172) | 0.59 ± 0.2 | |
| 194 | Ac-Sar$_2$-(D-Ala)HDVP-CPWGPFWCPVNRPGC (Ac-Sar$_2$- (SEQ ID NO: 173) | 1.2 ± 0.39 | |
| 195 | Ac-Sar$_2$-AADVP-CPWGPFWCPVNRPGC (Ac-Sar$_2$- (SEQ ID NO: 174) | 1.01 ± 0.19 | |
| 196 | Ac-Sar$_2$-A(D-His)DVP-CPWGPFWCPVNRPGC (Ac-Sar$_2$- (SEQ ID NO: 175) | 0.95 ± 0.24 | |
| 197 | Sar$_2$-A(D-His)DVP-CPWGPFWCPVNRPGC (Sar$_2$- (SEQ ID NO: 175) | 1.2 | |
| 198 | Ac-Sar$_2$-A(D-His)DVCPWGPFWCPVNRPGC (Ac-Sar$_2$- (SEQ ID NO: 176) | 20 ± 1.96 | |
| 199 | Sar$_2$-A(D-Ala)DVP-CPWGPFWCPVNRPGC (Sar$_2$- (SEQ ID NO: 177) | 3.35 ± 1.47 | |
| 200 | Ac-Sar$_2$-A(D-Asp)DVP-CPWGPFWCPVNRPGC (Ac-Sar$_2$- (SEQ ID NO: 178) | 4.1 ± 0.2 | |
| 201 | Sar$_2$-A(ThODVP-CPWGPFWCPVNRPGC (Sar$_2$- (SEQ ID NO: 179) | 0.6 ± 0.04 | |
| 202 | Sar$_2$-A(ThiAz)DVP-CPWGPFWCPVNRPGC (Sar$_2$- (SEQ ID NO: 180) | 0.7 ± 0.08 | |
| 203 | Sar$_2$-A(2FuAla)DVP-CPWGPFWCPVNRPGC (Sar$_2$- (SEQ ID NO: 181) | 0.49 ± 0.24 | |
| 204 | Ac-Sar$_2$-A(D-His)D(tBuGly)P-CPWGPFWCPVNRPGC (Ac-Sar$_2$- (SEQ ID NO: 182) | 2.15 ± 0.1 | |
| 205 | Sar$_2$-AHAVP-CPWGPFWCPVNRPGC (Sar$_2$- (SEQ ID NO: 183) | 1.8 ± 0.2 | |
| 206 | Sar$_2$-AH(D-Ala)VP-CPWGPFWCPVNRPGC (Sar$_2$- (SEQ ID NO: 184) | 8.3 ± 0.78 | |
| 207 | Sar$_2$-AHEVP-CPWGPFWCPVNRPGC (Sar$_2$- (SEQ ID NO: 185) | 1.3 ± 0.39 | |
| 208 | Sar$_2$-AH(D-Glu)VP-CPWGPFWCPVNRPGC (Sar$_2$- (SEQ ID NO: 186) | 2 ± 0.39 | |
| 209 | Sar$_2$-AH(D-Asp)VP-CPWGPFWCPVNRPGC (Sar$_2$- (SEQ ID NO: 187) | 1.25 ± 0.29 | |
| 210 | Ac-Sar$_2$-AH(D-Asp)VP-CPWGPFWCPVNRPGC (Ac-Sar$_2$- (SEQ ID NO: 187) | 1.1 ± 0.2 | |
| 211 | Ac-Sar$_2$-AH(D-Asp)(tBuGly)P-CPWGPFWCPVNRPGC (Ac-Sar$_2$- (SEQ ID NO: 188) | 3.1 ± 0.2 | |

TABLE 8-continued

Biological Assay Data for TBMB Peptide Ligands of the Invention (Competition Binding Assay)

| Bicycle Compound Number | Sequence | Ki, nM ± 95% CI Fluorescent peptide Human EphA2 Compound 18 | Ki, nM ± 95% CI Fluorescent peptide Mouse EphA2 Compound 18 |
|---|---|---|---|
| 212 | Ac-Sar₂-AH(D-Asp)V(Sar)-CPWGPFWCPVNRPGC (Ac-Sar₂-(SEQ ID NO: 189) | 4.95 ± 1.86 | |
| 213 | Ac-Sar₂-AH(D-Asp)V(Aib)-CPWGPFWCPVNRPGC (Ac-Sar₂-(SEQ ID NO: 190) | 1.9 ± 0.2 | |
| 214 | Sar₂-AHDAP-CPWGPFWCPVNRPGC (Sar₂-(SEQ ID NO: 191) | 22.5 ± 2.94 | |
| 215 | Sar₂-AHD(D-Ala)P-CPWGPFWCPVNRPGC (Sar₂-(SEQ ID NO: 192) | 26 ± 7.84 | |
| 216 | Sar₂-AHD(Aib)P-CPWGPFWCPVNRPGC (Sar₂-(SEQ ID NO: 193) | 2.77 ± 0.24 | |
| 217 | Sar₂-AHD(tBuGly)P-CPWGPFWCPVNRPGC (Sar₂-(SEQ ID NO: 194) | 0.49 n = 1 | |
| 218 | Sar₂-AHDVA-CPWGPFWCPVNRPGC (Sar₂-(SEQ ID NO: 195) | 1.27 ± 0.07 | |
| 219 | Sar₂-AHDV(D-Ala)-CPWGPFWCPVNRPGC (Sar₂-(SEQ ID NO: 196) | 15 ± 3.92 | |
| 220 | Sar₂-AHDV(Aib)-CPWGPFWCPVNRPGC (Sar₂-(SEQ ID NO: 197) | 0.83 ± 0.15 | |
| 221 | Sar₂-AHDV(Aze)-CPWGPFWCPVNRPGC (Sar₂-(SEQ ID NO: 198) | 3.1 ± 0.39 | |
| 222 | Sar₂-AHDV(Pip)-CPWGPFWCPVNRPGC (Sar₂-(SEQ ID NO: 199) | 3.4 ± 0.2 | |
| 223 | (β-Ala)-Sar₁₀-CPWGPFWCPVNRPGC ((β-Ala)-Sar₁₀-(SEQ ID NO: 200)) | 1.29 ± 0.42 | |
| 224 | Ac-Sar₂-(D-His)DVP-CPWGPFWCPVNRPGC (Ac-Sar₂-(SEQ ID NO: 201)) | 1.09 ± 0.13 | |
| 225 | Ac-Sar₂-AHDV(Aib)VP-CPWGPFWCPVNRPGC (Ac-Sar₂-(SEQ ID NO: 202)) | 1 ± 0.18 | 2.08 ± 1.27 |
| 226 | (β-Ala)-Sar₁₀-H(D-Asp)VP-CPWGPFWCPVNRPGC ((β-Ala)-Sar₁₀-(SEQ ID NO: 202)) | 0.84 ± 0.24 | |
| 227 | Ac-Sar₂-AH(D-Asp)VP-CP(1Nal)GPFWCP(tBuGly)N(HArg)PGC (Ac-Sar₂-(SEQ ID NO: 203)) | 0.75 ± 0.36 | |
| 228 | Ac-Sar₂-A(D-His)DVP-CPWGP(4)Ala)WCPVNRPGC (Ac-Sar₂-(SEQ ID NO: 204)) | 210.5 ± 48.02 | |
| 229 | Ac-Sar₂-A(D-His)DVP-CPWGPFWCP(HArg)NRPGC (Ac-Sar₂-(SEQ ID NO: 205)) | 5.1 ± 1.18 | |
| 230 | Ac-Sar₂-A(D-His)DVP-CP(1Nal)GPFWCP(tBuGly)N(HArg)PGC (Ac-Sar₂-(SEQ ID NO: 206)) | 1.8 ± 0.78 | |
| 231 | Ac-Sar₂-A(D-His)DVP-CP(1Nal)F(1Nal)CP(tBuGly)N(HArg)PGC (Ac-Sar₂-(SEQ ID NO: 207)) | 1.93 ± 0.23 | |
| 232 | Ac-Sar₂-A(D-His)DVP-CP(1Nal)F(1Nal)CP(tBuGly)NR(Aib)GC (Ac-Sar₂-(SEQ ID NO: 208)) | 0.9 ± 0.68 | |

TABLE 8-continued

Biological Assay Data for TBMB Peptide Ligands of the Invention (Competition Binding Assay)

| Bicycle Compound Number | Sequence | Ki, nM ± 95% CI Fluorescent peptide | |
|---|---|---|---|
| | | Human EphA2 Compound 18 | Mouse EphA2 Compound 18 |
| 233 | Ac-Sar₂-A(D-His)DVP-CPWG(Aib)FWCP(tBuGly)NR(Aib)GC (Ac-Sar₂-(SEQ ID NO: 209)) | 4.8 ± 0.84 | |
| 234 | (β-Ala)-Sar₁₀-H(D-Asp)VP-C(Aib)(1Nal)G(Aib)F(1Nal)CP(tBuGly)NRPGC ((β-Ala)-Sar₁₀-(SEQ ID NO: 210)) | 3.94 ± 1.72 | |
| 235 | (β-Ala)-Sar₁₀-H(D-Asp)VP-C(Aib)(1Nal)G(Aib)F(1Nal)CP(tBuGly)N(HArg)PGC ((β-Ala)-Sar₁₀-(SEQ ID NO: 211)) | 2.58 ± 0.96 | |
| 236 | (β-Ala)-Sar₁₀-H(D-Asp)VP-C(Aib)(1Nal)G(Aib)F(1Nal)CP(tBuGly)P(D-Asp)C ((β-Ala)-Sar₁₀-(SEQ ID NO: 120)) | 3 ± 0.71 | |
| 237 | Ac-(β-Ala)-Sar₁₀-H(D-Asp)VP-C(Aib)(1Nal)G(Aib)F(1Nal)CP(tBuGly)N(HArg)P(D-Asp)C (Ac-(β-Ala)-Sar₁₀-(SEQ ID NO: 120)) | 2.4 n = 1 | |
| 238 | (β-Ala)-Sar₁₀-H(D-Asp)VP-C(Aib)(1Nal)G(Aib)F(1Nal)CP(tBuGly)N(HArg)(Aib)(D-Asp)C ((β-Ala)-Sar₁₀-(SEQ ID NO: 212)) | 2.83 ± 0.19 | |
| 239 | (β-Ala)-Sar₁₀-H(D-Asp)VP-C(Aib)(1Nal)G(Aib)F(1Nal)CP(tBuGly)NR(Aib)GC ((β-Ala)-Sar₁₀-(SEQ ID NO: 213)) | 4.91 ± 2.45 | |
| 240 | (β-Ala)-Sar₁₀-H(D-Asp)VP-C(Aib)(1Nal)G(Aib)F(1Nal)CP(tBuGly)NR(Aib)(D-Asp)C ((β-Ala)-Sar₁₀-(SEQ ID NO: 121)) | 2.41 n = 1 | |
| 241 | Ac-(β-Ala)-Sar₁₀-H(D-Asp)VP-C(Aib)(1Nal)G(Aib)F(1Nal)CP(tBuGly)NR(Aib)(D-Asp)C (Ac-(β-Ala)-Sar₁₀-(SEQ ID NO: 121)) | 2.98 ± 0.96 | |
| 242 | (β-Ala)-Sar₁₀-H(D-Asp)VP-C(Aib)(1Nal)FWCP(tBuGly)N(HArg)P(D-Asp)C ((β-Ala)-Sar₁₀-(SEQ ID NO: 214)) | 7.77 ± 3.02 | |
| 243 | (β-Ala)-Sar₁₀-H(D-Asp)VP-C(Aib)(1Nal)GP(HArg)(1Nal)CP(tBuGly)NR(Aib)GC ((β-Ala)-Sar₁₀-(SEQ ID NO: 215)) | 2.83 ± 0.72 | |
| 244 | (β-Ala)-Sar₁₀-H(D-Asp)VP-C(Aib)(1Nal)GP(HArg)(1Nal)CP(tBuGly)N(HArg)P(D-Asp)C ((β-Ala)-Sar₁₀-(SEQ ID NO: 216)) | 2.8 ± 0.26 | |
| 245 | (β-Ala)-Sar₁₀-H(D-Asp)VP-C(Aib)WGP(HArg)(1Nal)CP(tBuGly)N(HArg)P(D-Asp)C ((β-Ala)-Sar₁₀-(SEQ ID NO: 217)) | 11.91 ± 4.3 | |
| 246 | (β-Ala)-Sar₁₀-H(D-Asp)VP-C(Aib)WGP(HArg)WCP(tBuGly)N(HArg)P(D-Asp)C ((β-Ala)-Sar₁₀-(SEQ ID NO: 218)) | 31.4 ± 24.3 | |
| 247 | (β-Ala)-Sar₁₀-H(D-Asp)VP-C(Aib)WGP(HArg)WCP(tBuGly)N(HArg)P(D-Asp)C ((β-Ala)-Sar₁₀-(SEQ ID NO: 218)) | 29.7 ± 11.76 | |

TABLE 8-continued

Biological Assay Data for TBMB Peptide Ligands of the Invention (Competition Binding Assay)

| Bicycle Compound Number | Sequence | Ki, nM ± 95% CI Fluorescent peptide | |
|---|---|---|---|
| | | Human EphA2 Compound 18 | Mouse EphA2 Compound 18 |
| 248 | (β-Ala)-Sar₁₀-H(D-Asp)VP-C(D-Ala)(1Nal)G(Aib)F(1Nal)CP(tBuGly)N(HArg)P(D-Asp)C ((β-Ala)-Sar₁₀-(SEQ ID NO: 219)) | 28.4 ± 0.78 | |
| 249 | (β-Ala)-Sar₁₀-H(D-Asp)VP-CP(1Nal)G(Aib)(HArg)(1Nal)CP(tBuGly)NR(Aib)GC ((β-Ala)-Sar₁₀-(SEQ ID NO: 220)) | 1.38 ± 0.46 | |
| 250 | (β-Ala)-Sar₁₀-H(D-Asp)VP-CP(1Nal)G(Aib)(HArg)(1Nal)CP(tBuGly)NR(Aib)(D-Asp)C ((β-Ala)-Sar₁₀-(SEQ ID NO: 221)) | 1.48 ± 0.7 | |
| 251 | (β-Ala)-Sar₁₀-H(D-Asp)VP-CP(1Nal)G(Aib)(HArg)(1Nal)CP(tBuGly)N(HArg)P(D-Asp)C ((β-Ala)-Sar₁₀-(SEQ ID NO: 222)) | 1.93 ± 0.62 | |
| 252 | (β-Ala)-Sar₁₀-H(D-Asp)VP-CP(1Nal)G(Aib)F(1Nal)CP(tBuGly)NRPGC ((β-Ala)-Sar₁₀-(SEQ ID NO: 223)) | 0.37 ± 0.18 | |
| 253 | Ac-Sar₂-H(D-Asp)VP-CP(1Nal)G(Aib)F(1Nal)CP(tBuGly)N(HArg)P(D-Asp)C (Ac-Sar₂-(SEQ ID NO: 224)) | 0.85 ± 0.82 | |
| 254 | Ac-Sar₂-H(D-Asp)VP-CP(1Nal)G(Aib)F(1Nal)CP(tBuGly)N(HArg)P(D-Asp)C (Ac-Sar₂-(SEQ ID NO: 122)) | 0.74 ± 0.2 | 0.64 ± 0.28 |
| 255 | (β-Ala)-Sar₂-H(D-Asp)VP-CP(1Nal)G(Aib)F(1Nal)CP(tBuGly)N(HArg)P(D-Asp)C ((β-Ala)-Sar₁₀-(SEQ ID NO: 122)) | 1.53 ± 0.58 | |
| 256 | Ac-(β-Ala)-Sar₁₀-H(D-Asp)VP-CP(1Nal)G(Aib)F(1Nal)CP(tBuGly)N(HArg)P(D-Asp)C (Ac-(β-Ala)-Sar₁₀-(SEQ ID NO: 122)) | 0.41 n = 1 | |
| 257 | (β-Ala)-Sar₂-H(D-Asp)VP-CP(1Nal)G(Aib)F(1Nal)CP(tBuGly)N(HArg)PGC ((β-Ala)-Sar₁₀-(SEQ ID NO: 224)) | 1.07 ± 0.2 | |
| 258 | Ac-(β-Ala)-Sar₁₀-H(D-Asp)VP-CP(1Nal)G(Aib)F(1Nal)CP(tBuGly)NR(Aib)GC (Ac-(β-Ala)-Sar₁₀-(SEQ ID NO: 123)) | 0.54 n = 1 | |
| 259 | (β-Ala)-Sar₂-H(D-Asp)VP-CP(1Nal)G(Aib)F(1Nal)CP(tBuGly)NR(Aib)(D-Asp)C ((β-Ala)-Sar₁₀-(SEQ ID NO: 225)) | 0.91 ± 0.14 | |
| 260 | Ac-(β-Ala)-Sar₁₀-H(D-Asp)VP-CP(1Nal)G(Aib)F(1Nal)CP(tBuGly)NR(Aib)(D-Asp)C (Ac-(β-Ala)-Sar₁₀-(SEQ ID NO: 124)) | 0.75 ± 0.07 | |
| 261 | Ac-Sar₂-H(D-Asp)VP-CP(1Nal)F(Aib)F(1Nal)CPVNR(Aib)GC(Ac-Sar₂-(SEQ ID NO: 226)) | 0.63 ± 0.43 | |
| 262 | Ac-Sar₂-H(D-Asp)VP-CP(1Nal)G(Aib)F(1Nal)CP(tBuGly)NR(Aib)GC (Ac-Sar₂-(SEQ ID NO: 123)) | 0.71 ± 0.17 | 0.72 ± 0.31 |

TABLE 8-continued

Biological Assay Data for TBMB Peptide Ligands of the Invention (Competition Binding Assay)

| Bicycle Compound Number | Sequence | Ki, nM ± 95% CI Fluorescent peptide | |
|---|---|---|---|
| | | Human EphA2 Compound 18 | Mouse EphA2 Compound 18 |
| 263 | (β-Ala)-Sar₁₀-H(D-Asp)VP-CP(1Nal)G(Aib)F(1Nal)CP(tBuGly)NR(Aib)GC ((β-Ala)-Sar₁₀-(SEQ ID NO: 123)) | 0.73 ± 0.26 | |
| 264 | (β-Ala)-Sar₁₀-H(D-Asp)VP-CP(1Nal)G(Aib)F(1Nal)CP(tBuGly)NR(Aib)(D-Asp)C ((β-Ala)-Sar₁₀-(SEQ ID NO: 124)) | 0.61 ± 0.31 | |
| 265 | (β-Ala)-Sar₁₀-H(D-Asp)VP-CP(1Nal)G(Aib)FWCP(tBuGly)N(HArg)P(D-Asp)C ((β-Ala)-Sar₁₀-(SEQ ID NO: 227)) | 1.55 ± 0.34 | |
| 266 | Ac-Sar₂-H(D-Asp)VP-CP(1Nal)G(Aib)FWCPVNR (Ac-Sar₂-(SEQ ID NO: 228)) | 1.6 ± 0.63 | |
| 267 | Ac-Sar₂-H(D-Asp)VP-CPW(Aza-Gly)PFWCPVNRPGC (Ac-Sar₂-(SEQ ID NO: 229)) | 0.66 ± 0.2 | |
| 268 | Ac-Sar₂-H(D-Asp)VP-CPWG(Aib)F(1Nal)CPVNR(Aib)GC (Ac-Sar₂-(SEQ ID NO: 230)) | 1.24 ± 0.46 | |
| 269 | (β-Ala)-Sar₂-H(D-Asp)VP-CPWG(Aib)F(1Nal)CP(tBuGly)N(HArg)P(D-Asp)C ((β-Ala)-Sar₁₀-(SEQ ID NO: 231)) | 1.11 ± 0.08 | |
| 270 | Ac-Sar₂-H(D-Asp)VP-CPWG(Aib)FWCP(tBuGly)NR(Aib)GC (Ac-Sar₂-(SEQ ID NO: 232)) | 1.52 ± 1.27 | |
| 271 | (β-Ala)-Sar₁₀-H(D-Asp)VP-CPWG(Aib)FWCP(tBuGly)N(HArg)P(D-Asp)C ((β-Ala)-Sar₁₀-(SEQ ID NO: 233)) | 3.66 ± 1.7 | |
| 272 | (β-Ala)-Sar₁₀-H(D-Asp)VP-CPWGP(HArg)WCP(tBuGly)N(HArg)P(D-Asp)C ((β-Ala)-Sar₁₀-(SEQ ID NO: 234)) | 3.99 ± 0.13 | |
| 273 | (β-Ala)-Sar₁₀-H(D-Asp)(C5g)P-C(Aib)(1Nal)G(Aib)F(1Nal)CP(tBuGly)NR(Aib)(D-Asp)C ((β-Ala)-Sar₁₀-(SEQ ID NO: 125)) | 1.5 n = 1 | |
| 274 | Ac-(β-Ala)-Sar₁₀-H(D-Asp)(C5g)P-C(Aib)(1Nal)G(Aib)F(1Nal)CP(tBuGly)NR(Aib)(D-Asp)C (Ac-(β-Ala)-Sar₁₀-(SEQ ID NO: 125)) | 2.28 ± 0.69 | |
| 275 | (β-Ala)-Sar₁₀-H(D-Asp)(C5g)P-C(Aib)WG(Aib)FWCP(tBuGly)NR(Aib)(D-Asp)C ((β-Ala)-Sar₁₀-(SEQ ID NO: 235)) | 15.9 ± 0.2 | |
| 276 | (β-Ala)-Sar₁₀-H(D-Asp)(C5g)P-CP(1Nal)G(Aib)F(1Nal)CP(tBuGly)N(HArg)P(D-Asp)C ((β-Ala)-Sar₁₀-(SEQ ID NO: 126)) | 0.62 ± 0.27 | |
| 277 | Ac-(β-Ala)-Sar₁₀-H(D-Asp)(C5g)P-CP(1Nal)G(Aib)F(1Nal)CP(tBuGly)N(HArg)P(D-Asp)C (Ac-(β-Ala)-Sar₁₀-(SEQ ID NO: 126)) | 0.53 ± 0.15 | |
| 278 | (β-Ala)-Sar₁₀-H(D-Asp)VP-CP(1Nal)G(Aib)F(1Nal)CP(tBuGly)NR(Aib)GC ((β-Ala)-Sar₁₀-(SEQ ID NO: 236)) | 0.46 ± 0.22 | |

TABLE 8-continued

Biological Assay Data for TBMB Peptide Ligands of the Invention (Competition Binding Assay)

| Bicycle Compound Number | Sequence | Ki, nM ± 95% CI Fluorescent peptide | |
|---|---|---|---|
| | | Human EphA2 Compound 18 | Mouse EphA2 Compound 18 |
| 279 | (β-Ala)-Sar$_{10}$-H(D-Asp)(C5g)T-CP(1Nal)G(Aib)F(1Nal)CP(tBuGly)NR(Aib)GC ((β-Ala)-Sar$_{10}$-(SEQ ID NO: 237)) | 0.59 ± 0.28 | |
| 280 | (β-Ala)-Sar$_{10}$-H(D-Asp)(C5g)T-CP(1Nal)G(Aib)F(1Nal)CP(tBuGly)N(HArg)P(D-Asp)C ((β-Ala)-Sar$_{10}$-(SEQ ID NO: 238)) | 0.64 ± 0.48 | |
| 281 | Ac-Sar$_2$-A(D-Asp)DVT-CPWGPFWCPVNRPGC (Ac-Sar$_2$-(SEQ ID NO: 239)) | 5.78 ± 1.1 | |
| 282 | Ac-Sar$_2$-A(D-Asp)DVT-CP(1Nal)GPFWCPVNRPGC (Ac-Sar$_2$-(SEQ ID NO: 240)) | 0.87 ± 0.14 | |
| 283 | Ac-Sar$_2$-A(D-Asp)DVT-CP(1Nal)GPF(1Nal)CPVNRPGC (Ac-Sar$_2$-(SEQ ID NO: 241)) | 0.28 ± 0.08 | |
| 284 | Ac-Sar$_2$-A(D-Asp)DVT-CP(1Nal)G(Aib)FWCP(tBuGly)N(HArg)PGC (Ac-Sar$_2$-(SEQ ID NO: 242)) | 3.8 ± 0.77 | |
| 285 | Ac-Sar$_2$-H(D-Asp)VT-CP(1Nal)G(Aib)F(1Nal)CP(tBuGly)NR(Aib)GC (Ac-Sar$_2$-(SEQ ID NO: 243)) | 1.21 ± 0.29 | |

TABLE 9

Biological Assay Data for TBMB Peptide Ligands of the Invention (Ala scan peptides, Competition Binding Assay)

| Bicycle Compound Number | Sequence | Ki, nM ± 95% CI Human EphA2 Fluorescent Peptide Compound 66 | Compound 18 |
|---|---|---|---|
| 25 | Ac-CANDWLCSLGWTC (Ac-(SEQ ID NO: 23)) | 328 n = 1 | |
| 26 | Ac-CMNDWLCALGWTC (Ac-(SEQ ID NO: 24)) | 71.6 ± 3.33 | |
| 27 | Ac-CMNDWLCSAGWTC (Ac-(SEQ ID NO: 25)) | 356 n = 1 | |
| 286 | Sar$_2$-ACAWGPFWCPVNRPGC (Sar$_2$-(SEQ ID NO: 244)) | 886 ± 474.47 | |
| 287 | Sar$_2$-ACPAGPFWCPVNRPGC (Sar$_2$-(SEQ ID NO: 245)) | >11000 | |
| 288 | Sar$_2$-ACPWAPFWCPVNRPGC (Sar$_2$-(SEQ ID NO: 246)) | >28000 | >1000 |
| 289 | Sar$_2$-ACPWGAFWCPVNRPGC (Sar$_2$-(SEQ ID NO: 247)) | 1102 ± 186.2 | >1000 |
| 83 | Sar$_2$-ACPWGPAWCPVNRPGC (Sar$_2$-(SEQ ID NO: 63)) | 287.5 ± 197.95 | 199 n = 1 |
| 290 | Sar$_2$-ACPWGPFACPVNRPGC (Sar$_2$-(SEQ ID NO: 248)) | >7000 | |
| 291 | Sar$_2$-ACPWGPFWCAVNRPGC (Sar$_2$-(SEQ ID NO: 249)) | >6000 | >1000 |
| 292 | Sar$_2$-ACPWGPFWCPANRPGC (Sar$_2$-(SEQ ID NO: 250)) | 953.5 ± 59.78 | |
| 101 | Sar$_2$-ACPWGPFWCPVARPGC (Sar$_2$-(SEQ ID NO: 81)) | 265 ± 235.04 | 293 n = 1 |
| 293 | Sar$_2$-ACPWGPFWCPVNAPGC (Sar$_2$-(SEQ ID NO: 251)) | 711 ± 581.64 | |
| 104 | Sar$_2$-ACPWGPFWCPVNRAGC (Sar$_2$-(SEQ ID NO: 84)) | 193.67 ± 112.76 | 124 n = 1 |
| 111 | Sar$_2$-ACPWGPFWCPVNRPAC (Sar$_2$-(SEQ ID NO: 91)) | 237.5 ± 164.92 | 108 n = 1 |
| 294 | Sar$_2$-AC(D-Ala)WGPFWCPVNRPGC (Sar$_2$-(SEQ ID NO: 252)) | >4000 | |
| 295 | Sar$_2$-ACP(D-Ala)GPFWCPVNRPGC (Sar$_2$-(SEQ ID NO: 253)) | >7000 | |
| 296 | Sar$_2$-ACPW(D-Ala)PFWCPVNRPGC (Sar$_2$-(SEQ ID NO: 254)) | 1003 n = 1 | |
| 297 | Sar$_2$-ACPWG(D-Ala)FWCPVNRPGC (Sar$_2$-(SEQ ID NO: 255)) | 1497 n = 1 | |
| 298 | Sar$_2$-ACPWGP(D-Ala)WCPVNRPGC (Sar$_2$-(SEQ ID NO: 256)) | >6500 | |
| 299 | Sar$_2$-ACPWGPF(D-Ala)CPVNRPGC (Sar$_2$-(SEQ ID NO: 257)) | >4000 | |
| 300 | Sar$_2$-ACPWGPFWC(D-Ala)VNRPGC (Sar$_2$-(SEQ ID NO: 258)) | >1200 | |
| 301 | Sar$_2$-ACPWGPFWCP(D-Ala)NRPGC (Sar$_2$-(SEQ ID NO: 259)) | >4000 | |
| 102 | Sar$_2$-ACPWGPFWCPV(D-Ala)RPGC (Sar$_2$-(SEQ ID NO: 82)) | 311.67 ± 195.55 | 317 ± 168.56 |
| 302 | Sar$_2$-ACPWGPFWCPVN(D-Ala)PGC (Sar$_2$-(SEQ ID NO: 260)) | 1410 ± 680.11 | >1000 |
| 105 | Sar$_2$-ACPWGPFWCPVNR(D-Ala)GC (Sar$_2$-(SEQ ID NO: 85)) | 470.67 ± 221.53 | 677 n = 1 |
| 112 | Sar$_2$-ACPWGPFWCPVNRP(D-Ala)C (Sar$_2$-(SEQ ID NO: 92)) | 109.83 ± 66.19 | 89 ± 15.68 |
| 303 | (β-Ala)-Sar$_{10}$-ACPWAPFWCAVNRPGC ((β-Ala)-Sar$_{10}$-(SEQ ID NO: 261)) | | >1000 |
| 304 | 4-(Pyridyl-2-disulfanyl)-4-RS-methylbutanoyl-(β-Ala)-Sar$_{10}$-ACPWAPFWCAVNRPGC (4-(Pyridyl-2-disulfanyl)-4-RS-methylbutanoyl-(β-Ala)-Sar$_{10}$-(SEQ ID NO: 261)) | | >10000 |
| 173 | Ac-Sar$_2$-A(D-Asp)VTCPWGPAWCPVNRPGC (Ac-Sar$_2$-(SEQ ID NO: 152)) | | 6.69 ± 3.49 |
| 305 | (β-Ala)-Sar$_{10}$-H(D-Asp)VPCP(1Nal)A(Aib)F(1Nal)CA(tBuGly)NR(Aib)(D-Asp)C ((β-Ala)-Sar$_{10}$-(SEQ ID NO: 262)) | | >5000 |
| 151 | ADVHCPW(Ala)PFWCPVNRPGCA (SEQ ID NO: 130) | | 393.5 ± 206.78 |
| 152 | ADVHCPWG(Ala)FWCPVNRPGCA (SEQ ID NO: 131) | | 1.8 ± 0.74 |
| 154 | ADVHCPWGPFWC(D-Ala)VNRPGCA (SEQ ID NO: 133) | | 101.03 ± 33.68 |

TABLE 9-continued

Biological Assay Data for TBMB Peptide Ligands of the Invention (Ala scan peptides, Competition Binding Assay)

| Bicycle Compound Number | Sequence | Ki, nM ± 95% CI Human EphA2 Fluorescent Peptide Compound 66 | Compound 18 |
|---|---|---|---|
| 155 | ADVHCPWGPFWCPV(D-Ala)RPGCA (SEQ ID NO: 134) | | 2 ± 0.74 |
| 156 | ADVHCPWGPFWCPVN(D-Ala)PGCA (SEQ ID NO: 135) | | 14.93 ± 2.3 |
| 306 | DOTA-(β-Ala)-Sar$_{10}$-H(D-Asp)VPCP(1Nal)A(Aib)F(1Nal)CA(tBuGly)NR(Aib)(D-Asp)C(DOTA-(β-Ala)-Sar$_{10}$-(SEQ ID NO: 262)) | >250 | |

TABLE 10

Biological Assay Data for TBMB Peptide Ligands of the Invention (Ala scan peptides, Direct Binding Assay)

| Bicycle Compound Number | Sequence | $K_D$, nM ± 95% CI Human EphA2 |
|---|---|---|
| 307 | AF488-(β-Ala)-Sar$_{10}$-ACPWAPFWCAVNRPGC (AF488-(β-Ala)-Sar$_{10}$-(SEQ ID NO: 261)) | >1000 |
| 308 | AF488-(β-Ala)-Sar$_{10}$-H(D-Asp)VPCP(1Nal)A(Aib)F(1Nal)CA(tBuGly)NR(Aib)(D-Asp)C (AF488-(β-Ala)-Sar$_{10}$-(SEQ ID NO: 262)) | >2000 |

TABLE 11

Biological Assay Data for TBMB Peptide Ligands of the Invention (BDC comp data with TBMB Scaffolds)

| BDC Compound Number | Bicycle precursor | General Formula | Ki, nM ± 95% CI Human EphA2 Fluorescent Peptide | | |
|---|---|---|---|---|---|
| | | | Compound 66 | Compound 18 | Compound 12 |
| BDC-1 | Compound 72 | Formula (A) | 41.3 n = 1 | 10.5 ± 0.98 | 78.1 n = 1 |
| BDC-2 | Compound 72 | Formula (B) | | 22.23 ± 10.77 | |
| BDC-3 | Compound 226 | Formula (B) | | 0.38 ± 0.1 | |
| BDC-4 | Compound 227 | Formula (B) | | 1.72 ± 0.99 | |
| BDC-5 | Compound 303 | Formula (B) | | >1000 | >1000 |

TABLE 12

Selectivity Data for Peptide Ligands of the Invention (Selectivity Direct Binding Assay)

| Bicycle Compound Number | mouse EphA2 | rat EphA2 | dog EphA2 | Human & mouse EphA3 | rat EphA3 | human EphA4 | rat & mouse EphA4 | rat EphB1 |
|---|---|---|---|---|---|---|---|---|
| 1 | 301 n = 1 | | | >2000 | | >5000 | | |
| 12 | 55.5 n = 1 | | | | | | | |
| 66 | 22 n = 1 | | | >2000 | | >5000 | | 2268 n = 1 |
| 67 | 51.8 ± 6.27 | 26.5 ± 10.69 | 61.43 ± 27.05 | >10000 | >4000 | >5000 | >1000 | |
| 144 | 2.56 n = 1 | 1.25 n = 1 | 4.39 n = 1 | 166 n = 1 | | >2500 | | 1444 n = 1 |
| 145 | 3.8 ± 0.55 | 1 ± 0.4 | 4.99 ± 1.02 | 129.25 ± 13.3 | 297 ± 71.24 | 1497.2 ± 1151.8 | 2535.33 ± 2325.76 | 5421 n = 1 |

TABLE 12-continued

Selectivity Data for Peptide Ligands of the Invention (Selectivity Direct Binding Assay)

| | | | | | | | | |
|---|---|---|---|---|---|---|---|---|
| 143 | 4.69 ± 4.15 | 1.38 ± 1.36 | 4.47 ± 3.09 | 259.5 ± 8.82 | 474 n = 1 | 5990000 n = 1 | 1000000 n = 1 | 1090 n = 1 |
| 140 | 4.55 ± 1.04 | 1.57 ± 0.46 | 8.7 ± 3.23 | 3691 n = 1 | >4000 | >2500 | >2000 | >2000 |
| 147 | 3.44 ± 1.31 | 1.15 ± 0.33 | 3.58 ± 0.89 | 82.5 ± 20.12 | 221 ± 61.76 | 7441983.67 ± 8013305.7 | 1002814.33 ± 1957206.91 | |
| 141 | 6.5 ± 0.63 | 2.33 ± 0.49 | 13.33 ± 1.77 | >4000 | 137 n = 1 | 237610 ± 384917.33 | 1889 n = 1 | |
| 308 | >2000 | >2000 | >2000 | >4000 | >4000 | >5000 | >1000 | |
| 139 | 0.8 ± 0.54 | 0.36 ± 0.08 | 2.17 ± 0.76 | >10000 | >4000 | >4000 | >4000 | >2000 |
| 68 | 23.4 n = 1 | 15.9 n = 1 | 31.9 n = 1 | >10000 | >4000 | >4000 | >4000 | >2000 |
| 18 | 4.02 ± 2 | 1.72 n = 1 | 3.57 n = 1 | >2000 | | >1000 | | 1418 n = 1 |
| 23 | | | | | | | | |
| 146 | 386 | | | 7186 n = 1 | | | | |

| Bicycle Compound Number | Human EphB4 | Human EphA7 | Human EphA6 | Human EphA1 | human Factor XIIa | human Carbonic anhydrase 9 | human CD38 |
|---|---|---|---|---|---|---|---|
| 1 | | >1000 | | 1640 n = 1 | | | |
| 12 | | | | | | | |
| 66 | >4000 | >1000 | >3000 | 1178 n = 1 | | | |
| 67 | | | | | | | |
| 144 | >4000 | >1000 | >3000 | 1712 n = 1 | | | |
| 145 | >4000 | >1000 | >3000 | 7260 n = 1 | | | |
| 143 | >4000 | >1000 | >3000 | 1283 n = 1 | | | |
| 140 | >4000 | >1000 | >3000 | >1000 | >8000 | >10000 | >10000 |
| 147 | >4000 | >1000 | >3000 | 1218 n = 1 | | | |
| 141 | | | | | | | |
| 308 | | | | | | | |
| 139 | >4000 | >1000 | >2000 | >2000 | >8000 | >10000 | >10000 |
| 68 | >4000 | >1000 | >3000 | >2000 | >8000 | >10000 | >10000 |
| 18 | >4000 | >1000 | >3000 | >2000 | | | |
| 23 | | | | | | | |
| 146 | | | | | | | |

The invention claimed is:
1. A peptide ligand specific for EphA2 comprising a polypeptide comprising at least three cysteine residues, separated by at least two loop sequences, and an aromatic molecular scaffold which forms covalent bonds with the cysteine residues of the polypeptide such that at least two polypeptide loops are formed on the molecular scaffold, wherein the molecular scaffold is 1,3,5-tris(bromomethyl)benzene (TBMB), and wherein the polypeptide comprises an amino acid sequence selected from:

ACMNDWLCSLGWTCA (SEQ ID NO: 1);
ACMNDWLCSLGWTC (SEQ ID NO: 2);
ACMNDWLCELGWTCA (SEQ ID NO: 3);
ACTRQGIWCALGFEPCA (SEQ ID NO: 4);
ACMNDWLCTLGWSCA (SEQ ID NO: 5);
ACMNDWLCQLGWTCA (SEQ ID NO: 6);
ACMNDWLCTLGWTCA (SEQ ID NO: 7);
ACMNDWLCDLGWRCA (SEQ ID NO: 8);
ACMNDWLCELGWSCA (SEQ ID NO: 9);
ACRVSPEYCPFGPVWCAGAAA (SEQ ID NO: 10);
ACPWGPAWCPVHGKTCA (SEQ ID NO: 11);
ACPWGPAWCPVNRPGCA (SEQ ID NO: 12);
ACPWGPAWCPVNRPGCAGAAA (SEQ ID NO: 13);
ACPWGPMWCPVNRPGCA (SEQ ID NO: 14);
ACPWGPNWCPVNRPGCA (SEQ ID NO: 15);
AGEMACPWGPFWCPVNRPGCA (SEQ ID NO: 16);
ADVTCPWGPFWCPVNRPGCA (SEQ ID NO: 17);
ADVRTCPWGPFWCPVNRPGCA (SEQ ID NO: 18);
ANDVTCPWGPFWCPVNRPGCA (SEQ ID NO: 19);
ACVPQGIWCALQFEPCA (SEQ ID NO: 20);
ACQKQGLWCALGFEPCA (SEQ ID NO: 21);
ACLVNDDCFYMGLCA (SEQ ID NO: 22);
CANDWLCSLGWTC (SEQ ID NO: 23);
CMNDWLCALGWTC (SEQ ID NO: 24);
CMNDWLCSAGWTC (SEQ ID NO: 25);
ACMNDWLCQLGWKCA (SEQ ID NO: 26);
ACTQNDWLCSLGWTCA (SEQ ID NO: 27);
ACRNIPTMCPFGPVWCA (SEQ ID NO: 28);
ACRVSPEYCPFGPVWCA (SEQ ID NO: 29);
ACRVSPEYCPFGPTWCA (SEQ ID NO: 30);
ACRVSPEYCPFGPSWCA (SEQ ID NO: 31);
ACRVSPEYCPFGPEWCA (SEQ ID NO: 32);
ACRVSPEYCPFGPYWCA (SEQ ID NO: 33);
ACRVSPEYCPFGPLWCA (SEQ ID NO: 34);
ACRVSPEYCPFGPDWCA (SEQ ID NO: 35);
ACPWGPAWCPVRDTNCA (SEQ ID NO: 36);
ACPWGPAWCPVNGARCA (SEQ ID NO: 37);
ACPWGPAWCPVRNPCA (SEQ ID NO: 38);
ACPWGPAWCPVSRVCA (SEQ ID NO: 39);
ACPWGPAWCPVRSCA (SEQ ID NO: 40);
ACPWGPAWCPVKPTCA (SEQ ID NO: 41);
ACPWGPAWCPVNRNGCA (SEQ ID NO: 42);
AVHIPCPWGPSWCPVNRPGCA (SEQ ID NO: 43);
AEGLPCPWGPFWCPVNRPGCA (SEQ ID NO: 44);
ADHACPWGPFWCPVNRPGCA (SEQ ID NO: 45);
ADVHCPWGPFWCPVNRPGCA (SEQ ID NO: 46);
AHDVPCPWGPFWCPVNRPGCA (SEQ ID NO: 47);
ARDDPCPWGPFWCPVNRPGCA (SEQ ID NO: 48);
ACTTGSIWCALQFEPCA (SEQ ID NO: 49);
ACVPQGIWCALRYEPCA (SEQ ID NO: 50);
ACPWGPFWCPVNRPGCA (SEQ ID NO: 51);
ACPWGPFWCPVNRPGC (SEQ ID NO: 52);
AC(HyP)WGPFWCPVNRPGC (SEQ ID NO: 53);
AC(Aib)WGPFWCPVNRPGC (SEQ ID NO: 54);
AC(4FlPro)WGPFWCPVNRPGC (SEQ ID NO: 55);
ACP(1Nal)GPFWCPVNRPGC (SEQ ID NO: 56);
ACP(2Nal)GPFWCPVNRPGC (SEQ ID NO: 57);
ACPWG(Aze)FWCPVNRPGC (SEQ ID NO: 58);
ACPWG(HyP)FWCPVNRPGC (SEQ ID NO: 59);
ACPWG(Aib)FWCPVNRPGC (SEQ ID NO: 60);
ACPWG(4FlPro)FWCPVNRPGC (SEQ ID NO: 61);
ACPWG(Pip)FWCPVNRPGC (SEQ ID NO: 62);
ACPWGPAWCPVNRPGC (SEQ ID NO: 63);
ACPWGP(4Pal)WCPVNRPGC (SEQ ID NO: 64);
ACPWGP(4BrPhe)WCPVNRPGC (SEQ ID NO: 65);
ACPWGP(4MeOPhe)WCPVNRPGC (SEQ ID NO: 66);
ACPWGP(HPhe)WCPVNRPGC (SEQ ID NO: 67);
ACPWGP(4,4-BPA)WCPVNRPGC (SEQ ID NO: 68);
ACPWGP(NO2Phe5)WCPVNRPGC (SEQ ID NO: 69);
ACPWGP(3,4-DCPhe)WCPVNRPGC (SEQ ID NO: 70);
ACPWGPYWCPVNRPGC (SEQ ID NO: 71);
ACPWGP(3Pal)WCPVNRPGC (SEQ ID NO: 72);
ACPWGP(Phg)WCPVNRPGC (SEQ ID NO: 73);
ACPWGP(1Nal)WCPVNRPGC (SEQ ID NO: 74);
ACPWGP(2Nal)WCPVNRPGC (SEQ ID NO: 75);
ACPWGPF(1Nal)CPVNRPGC (SEQ ID NO: 76);
ACPWGPFWC(Aze)VNRPGC (SEQ ID NO: 77);
ACPWGPFWC(HyP)VNRPGC (SEQ ID NO: 78);
ACPWGPFWC(4F1Pro)VNRPGC (SEQ ID NO: 79);
ACPWGPFWCP(tBuGly)NRPGC (SEQ ID NO: 80);
ACPWGPFWCPVARPGC (SEQ ID NO: 81);
ACPWGPFWCPV(D-Ala)RPGC (SEQ ID NO: 82);
ACPWGPFWCPVN(HArg)PGC (SEQ ID NO: 83);
ACPWGPFWCPVNRAGC (SEQ ID NO: 84);
ACPWGPFWCPVNR(D-Ala)GC (SEQ ID NO: 85);
ACPWGPFWCPVNR(Aze)GC (SEQ ID NO: 86);
ACPWGPFWCPVNR(HyP)GC (SEQ ID NO: 87);
ACPWGPFWCPVNR(Pip)GC (SEQ ID NO: 88);
ACPWGPFWCPVNR(4FlPro)GC (SEQ ID NO: 89);
ACPWGPFWCPVNR(Aib)GC (SEQ ID NO: 90);
ACPWGPFWCPVNRPAC (SEQ ID NO: 91);
ACPWGPFWCPVNRP(D-Ala)C (SEQ ID NO: 92);
AC(Aib)(1Nal2)GPFWCPVNRPGC (SEQ ID NO: 93);
AC(Aib)WGPF(1Nal)CPVNRPGC (SEQ ID NO: 94);
ACP(1Nal)GPFWCPV(D-Ala)RPGC (SEQ ID NO: 95);
ACP(1Nal)GPFWCPVNRP(D-Ala)C (SEQ ID NO: 96);
ACPWGPF(1Nal)CPV(D-Ala)RPGC (SEQ ID NO: 97);
ACPWGPF(1Nal)CPVNRP(D-Ala)C (SEQ ID NO: 98);
ACP(1Nal)G(Aib)FWCPVNRPGC (SEQ ID NO: 99);
ACP(1Nal)GPF(1Nal)CPVNRPGC (SEQ ID NO: 100);
ACP(1Nal)GPFWCP(tBuGly)NRPGC (SEQ ID NO: 101);
ACP(1Nal)GPFWCPVN(HArg)PGC (SEQ ID NO: 102);
ACPWG(Aib)F(1Nal)CPVNRPGC (SEQ ID NO: 103);
AC(Aib)(1Nal)GPFWCPV(D-Ala)RPGC (SEQ ID NO: 104);
AC(Aib)(1Nal)GPFWCPVNRP(D-Ala)C (SEQ ID NO: 105);
ACP(1Nal)G(Aib)FWCP(tBuGly)NRPGC (SEQ ID NO: 106);
ACP(1Nal)G(Aib)FWCPV(D-Ala)RPGC (SEQ ID NO: 107);
ACP(1Nal)G(Aib)FWCPVNRP(D-Ala)C (SEQ ID NO: 108);
ACP(1Nal)GPFWCP(tBuGly)(D-Ala)RPGC (SEQ ID NO: 109);
ACP(1Nal)GPFWCP(tBuGly)N(HArg)PGC (SEQ ID NO: 110);
ACP(1Nal)GPFWCP(tBuGly)NR(Aib)GC (SEQ ID NO: 111);
ACP(1Nal)GPFWCP(tBuGly)NRP(D-Ala)C (SEQ ID NO: 112);
ACP(1Nal)GPFWCPV(D-Ala)(HArg)PGC (SEQ ID NO: 113);

ACP(1Nal)GPFWCPVN(HArg)P(D-Ala)C (SEQ ID NO: 114);
AC(Aib)(1Nal)G(Aib)FWCPVNR(Aib)GC (SEQ ID NO: 115);
ACP(1Nal)G(Aib)FWCP(tBuGly)N(HArg)PGC (SEQ ID NO: 116);
ACP(1Nal)G(Aib)FWCP(tBuGly)NR(Aib)GC (SEQ ID NO: 117);
ACP(1Nal)GPFWCP(tBuGly)N(HArg)(Aib)GC (SEQ ID NO: 118);
H(D-Asp)VPCPWGPFWCPVNRPGCA (SEQ ID NO: 119);
H(D-Asp)VP-C(Aib)(1Nal)G(Aib)F(1Nal)CP(tBuGly)N(HArg)P(D-Asp)C (SEQ ID NO: 120);
H(D-Asp)VP-C(Aib)(1Nal)G(Aib)F(1Nal)CP(tBuGly)NR(Aib)(D-Asp)C (SEQ ID NO: 121);
H(D-Asp)VP-CP(1Nal)G(Aib)F(1Nal)CP(tBuGly)N(HArg)P(D-Asp)C (SEQ ID NO: 122);
H(D-Asp)VP-CP(1Nal)G(Aib)F(1Nal)CP(tBuGly)N(HArg)P(D-Asp)C (SEQ ID NO: 122);
H(D-Asp)VP-CP(1Nal)G(Aib)F(1Nal)CP(tBuGly)NR(Aib)GC (SEQ ID NO: 123);
H(D-Asp)VP-CP(1Nal)G(Aib)F(1Nal)CP(tBuGly)NR(Aib)(D-Asp)C (SEQ ID NO: 124);
H(D-Asp)(C5g)P-C(Aib)(1Nal)G(Aib)F(1Nal)CP(tBuGly)NR(Aib)(D-Asp)C (SEQ ID NO: 125);
H(D-Asp)(C5g)P-CP(1Nal)G(Aib)F(1Nal)CP(tBuGly)N(HArg)P(D-Asp)C (SEQ ID NO: 126);
ADVH-CPWGPFWCPVNRPGC (SEQ ID NO: 127);
ADVH-CP(3,3-DPA)GPFWCPVNRPGCA (SEQ ID NO: 128);
ADVH-CP(1Nal)GPFWCPVNRPGCA (SEQ ID NO: 129);
ADVH-CPWAPFWCPVNRPGCA (SEQ ID NO: 130);
ADVH-CPWGAFWCPVNRPGCA (SEQ ID NO: 131);
ADVH-CPWG(Aib)FWCPVNRPGCA (SEQ ID NO: 132);
ADVH-CPWGPFWCAPVNRPGCA (SEQ ID NO: 133);
ADVH-CPWGPFWCPV(D-Ala)RPGCA (SEQ ID NO: 134);
ADVH-CPWGPFWCPVN(D-Ala)PGCA (SEQ ID NO: 135);
ADVT-CPWGPFWCPVNRPGC (SEQ ID NO: 136);
A(D-Asp)VT-CPWGPFWCPVNRPGC (SEQ ID NO: 137);
A(D-Asp)(D-Asp)T-CPWGPFWCPVNRPGC (SEQ ID NO: 138);
A(D-Asp)(Cba)T-CPWGPFWCPVNRPGC (SEQ ID NO: 139);
A(D-Asp)(Cpa)T-CPWGPFWCPVNRPGC (SEQ ID NO: 140);
A(D-Asp)(Cpg)T-CPWGPFWCPVNRPGC (SEQ ID NO: 141);
A(D-Asp)(C5g)VT-CPWGPFWCPVNRPGC (SEQ ID NO: 142);
AD(tBuGly)T-CPWGPFWCPVNRPGC (SEQ ID NO: 143);
A(D-Asp)VT-C(AC3C)WGPFWCPVNRPGC (SEQ ID NO: 144);
A(D-Asp)VT-C(AC4C)WGPFWCPVNRPGC (SEQ ID NO: 145);
A(D-Asp)VT-C(AC5C)WGPFWCPVNRPGC (SEQ ID NO: 146);
A(D-Asp)VT-C(4BenzyPro)WGPFWCPVNRPGC (SEQ ID NO: 147);
A(D-Asp)VT-C(4PhenyPro)WGPFWCPVNRPGC (SEQ ID NO: 148);
A(D-Asp)VT-CP(1Nal)GPFWCPVNRPGC (SEQ ID NO: 149);
A(D-Asp)VT-CPWGP(HArg)WCPVNRPGC (SEQ ID NO: 150);
A(D-Asp)VT-CPWGPNWCPVNRPGC (SEQ ID NO: 151);
A(D-Asp)VT-CPWGPAWCPVNRPGC (SEQ ID NO: 152);
A(D-Asp)VT-CPWGPFWCPLNRPGC (SEQ ID NO: 153);
A(D-Asp)VT-CPWGPFWCPVNRP(D-Asp)C (SEQ ID NO: 154);
A(D-Asp)VT-CPWGPFWCPVN(HArg)P(D-Asp)C (SEQ ID NO: 155);
A(D-Asp)VT-CPWGPFWCPVNR(Aib)(D-Asp)C (SEQ ID NO: 156);
A(D-Asp)VT-CP(1Nal)G(Aib)FWCPVNR(Aib)GC (SEQ ID NO: 157);
A(D-Asp)VT-CPWG(Aib)F(1Nal)CPVNR(Aib)GC (SEQ ID NO: 158);
A(D-Asp)VT-CPWG(Aib)FWCP(tBuGly)NR(Aib)GC (SEQ ID NO: 159);
A(D-Asp)VT-CP(1Nal)G(Aib)F(1Nal)CPVNR(Aib)GC (SEQ ID NO: 160);
A(D-Asp)VT-CP(1Nal)G(Aib)F(1Nal)CP(tBuGly)N(HArg)PGC (SEQ ID NO: 161);
A(D-Asp)VT-CP(1Nal)G(Aib)F(1Nal)CP(tBuGly)NR(Aib)GC (SEQ ID NO: 162);
A(D-Asp)VT-CP(1Nal)G(Aib)F(1Nal)CP(tBuGly)N(HArg)P(D-Asp)C (SEQ ID NO: 163);
(D-Asp)VT-CPWGPFWCPVNRPGC (SEQ ID NO: 164);
(D-Asp)VT-CP(1Nal)G(Aib)F(1Nal)CP(tBuGly)NR(Aib)GC (SEQ ID NO: 165);
AHDVP-CP(1Nal)GPFWCPVNRPGCA (SEQ ID NO: 166);
AHDVP-CP(1Nal)GPFWCPVNRPGC (SEQ ID NO: 167);
AHDVP-CPWGPF(1Nal)CPVNRPGC (SEQ ID NO: 168);
AHDVP-CP(1Nal)GPFWCP(tBuGly)NRPGC (SEQ ID NO: 169);
AHDVP-CP(1Nal)G(Aib)FWCP(tBuGly)N(HArg)PGC (SEQ ID NO: 170);
AHDVP-CP(1Nal)G(Aib)FWCP(tBuGly)NR(Aib)GC (SEQ ID NO: 171);
AHDVP-CPWGPFWCPVNRPGC (SEQ ID NO: 172);
(D-Ala)HDVP-CPWGPFWCPVNRPGC (SEQ ID NO: 173);
AADVP-CPWGPFWCPVNRPGC (SEQ ID NO: 174);
A(D-His)DVP-CPWGPFWCPVNRPGC (SEQ ID NO: 175);
A(D-His)DVCPWGPFWCPVNRPGC (SEQ ID NO: 176);
A(D-Ala)DVP-CPWGPFWCPVNRPGC (SEQ ID NO: 177);
A(D-Asp)DVP-CPWGPFWCPVNRPGC (SEQ ID NO: 178);
A(Thi)DVP-CPWGPFWCPVNRPGC (SEQ ID NO: 179);
A(ThiAz)DVP-CPWGPFWCPVNRPGC (SEQ ID NO: 180);
A(2FuAla)DVP-CPWGPFWCPVNRPGC (SEQ ID NO: 181);
A(D-His)D(tBuGly)P-CPWGPFWCPVNRPGC (SEQ ID NO: 182);
AHAVP-CPWGPFWCPVNRPGC (SEQ ID NO: 183);

AH(D-Ala)VP-CPWGPFWCPVNRPGC (SEQ ID NO: 184);
AHEVP-CPWGPFWCPVNRPGC (SEQ ID NO: 185);
AH(D-Glu)VP-CPWGPFWCPVNRPGC (SEQ ID NO: 186);
AH(D-Asp)VP-CPWGPFWCPVNRPGC (SEQ ID NO: 187);
AH(D-Asp)(tBuGly)P-CPWGPFWCPVNRPGC (SEQ ID NO: 188);
AH(D-Asp)V(Sar)-CPWGPFWCPVNRPGC (SEQ ID NO: 189);
AH(D-Asp)V(Aib)-CPWGPFWCPVNRPGC (SEQ ID NO: 190);
AHDAP-CPWGPFWCPVNRPGC (SEQ ID NO: 191);
AHD(D-Ala)P-CPWGPFWCPVNRPGC (SEQ ID NO: 192);
AHD(Aib)P-CPWGPFWCPVNRPGC (SEQ ID NO: 193);
AHD(tBuGly)P-CPWGPFWCPVNRPGC (SEQ ID NO: 194);
AHDVA-CPWGPFWCPVNRPGC (SEQ ID NO: 195);
AHDV(D-Ala)-CPWGPFWCPVNRPGC (SEQ ID NO: 196);
AHDV(Aib)-CPWGPFWCPVNRPGC (SEQ ID NO: 197);
AHDV(Aze)-CPWGPFWCPVNRPGC (SEQ ID NO: 198);
AHDV(Pip)-CPWGPFWCPVNRPGC [(SEQ ID NO: 199);
HDVP-CPWGPFWCPVNRPGC (SEQ ID NO: 200);
(D-His)DVP-CPWGPFWCPVNRPGC (SEQ ID NO: 201);
H(D-Asp)VP-CPWGPFWCPVNRPGC (SEQ ID NO: 202);
AH(D-Asp)VP-CP(1Nal)GPFWCP(tBuGly)N(HArg)PGC (SEQ ID NO: 203);
A(D-His)DVP-CPWGP(ΨAla)WCPVNRPGC (SEQ ID NO: 204);
A(D-His)DVP-CPWGPFWCP(HArg)NRPGC (SEQ ID NO: 205);
A(D-His)DVP-CP(1Nal)GPFWCP(tBuGly)N(HArg)PGC (SEQ ID NO: 206);
A(D-His)DVP-CP(1Nal)G(Aib)F(1Nal)CP(tBuGly)N(HArg)PGC (SEQ ID NO: 207);
A(D-His)DVP-CP(1Nal)G(Aib)F(1Nal)CP(tBuGly)NR(Aib)GC (SEQ ID NO: 208);
A(D-His)DVP-CPWG(Aib)FWCP(tBuGly)NR(Aib)GC (SEQ ID NO: 209);
H(D-Asp)VP-C(Aib)(1Nal)G(Aib)F(1Nal)CP(tBuGly)NRPGC (SEQ ID NO: 210);
H(D-Asp)VP-C(Aib)(1Nal)G(Aib)F(1Nal)CP(tBuGly)N(HArg)PGC (SEQ ID NO: 211);
H(D-Asp)VP-C(Aib)(1Nal)G(Aib)F(1Nal)CP(tBuGly)N(HArg)(Aib)(D-Asp)C (SEQ ID NO: 212);
H(D-Asp)VP-C(Aib)(1Nal)G(Aib)F(1Nal)CP(tBuGly)NR(Aib)GC (SEQ ID NO: 213);
(β-Ala)-Sar₁₀-H(D-Asp)VP-C(Aib)(1Nal)G(Aib)FWCP(tBuGly)N(HArg)P(D-Asp)C ((β-Ala)-Sar₁₀-(SEQ ID NO: 214))
H(D-Asp)VP-C(Aib)(1Nal)GP(HArg)(1Nal)CP(tBuGly)NR(Aib)GC (SEQ ID NO: 215);
H(D-Asp)VP-C(Aib)(1Nal)GP(HArg)(1Nal)CP(tBuGly)N(HArg)P(D-Asp)C (SEQ ID NO: 216);
H(D-Asp)VP-C(Aib)WGP(HArg)(1Nal)CP(tBuGly)N(HArg)P(D-Asp)C (SEQ ID NO: 217);
H(D-Asp)VP-C(Aib)WGP(HArg)WCP(tBuGly)N(HArg)P(D-Asp)C (SEQ ID NO: 218);
H(D-Asp)VP-C(D-Ala)(1Nal)G(Aib)F(1Nal)CP(tBuGly)N(HArg)P(D-Asp)C (SEQ ID NO: 219);
H(D-Asp)VP-CP(1Nal)G(Aib)(HArg)(1Nal)CP(tBuGly)NR(Aib)GC (SEQ ID NO: 220);
H(D-Asp)VP-CP(1Nal)G(Aib)(HArg)(1Nal)CP(tBuGly)NR(Aib)(D-Asp)C (SEQ ID NO: 221);
H(D-Asp)VP-CP(1Nal)G(Aib)(HArg)(1Nal)CP(tBuGly)N(HArg)P(D-Asp)C (SEQ ID NO: 222);
H(D-Asp)VP-CP(1Nal)G(Aib)F(1Nal)CP(tBuGly)NRPGC (SEQ ID NO: 223);
H(D-Asp)VP-CP(1Nal)G(Aib)F(1Nal)CP(tBuGly)N(HArg)PGC (SEQ ID NO: 224);
H(D-Asp)VP-CP(1Nal)G(Aib)F(1Nal)CP(tBuGly)N(HArg)(Aib)(D-Asp)C (SEQ ID NO: 225);
H(D-Asp)VP-CP(1Nal)G(Aib)F(1Nal)CPVNR(Aib)GC (SEQ ID NO: 226);
H(D-Asp)VP-CP(1Nal)G(Aib)FWCP(tBuGly)N(HArg)P(D-Asp)C (SEQ ID NO: 227);
H(D-Asp)VP-CP(1Nal)G(Aib)FWCPVNR(Aib)GC (SEQ ID NO: 228);
H(D-Asp)VP-CPW(Aza-Gly)PFWCPVNRPGC (SEQ ID NO: 229);
H(D-Asp)VP-CPWG(Aib)F(1Nal)CPVNR(Aib)GC (SEQ ID NO: 230);
H(D-Asp)VP-CPWG(Aib)F(1Nal)CP(tBuGly)N(HArg)P(D-Asp)C (SEQ ID NO: 231);
H(D-Asp)VP-CPWG(Aib)FWCP(tBuGly)NR(Aib)GC (SEQ ID NO: 232);
H(D-Asp)VP-CPWG(Aib)FWCP(tBuGly)N(HArg)P(D-Asp)C (SEQ ID NO: 233);
H(D-Asp)VP-CPWGP(HArg)WCP(tBuGly)N(HArg)P(D-Asp)C (SEQ ID NO: 234);
H(D-Asp)(C5g)P-C(Aib)WG(Aib)FWCP(tBuGly)NR(Aib)(D-Asp)C (SEQ ID NO: 235);
H(D-Asp)(C5g)P-CP(1Nal)G(Aib)F(1Nal)CP(tBuGly)NR(Aib)GC (SEQ ID NO: 236);
H(D-Asp)(C5g)T-CP(1Nal)G(Aib)F(1Nal)CP(tBuGly)NR(Aib)GC (SEQ ID NO: 237);
H(D-Asp)(C5g)T-CP(1Nal)G(Aib)F(1Nal)CP(tBuGly)N(HArg)P(D-Asp)C (SEQ ID NO: 238);
A(D-Asp)DVT-CPWGPFWCPVNRPGC (SEQ ID NO: 239);
A(D-Asp)DVT-CP(1Nal)GPFWCPVNRPGC (SEQ ID NO: 240);
A(D-Asp)DVT-CP(1Nal)GPF(1Nal)CPVNRPGC (SEQ ID NO: 241);
A(D-Asp)DVT-CP(1Nal)G(Aib)FWCP(tBuGly)N(HArg)PGC (SEQ ID NO: 242);
H(D-Asp)VT-CP(1Nal)G(Aib)F(1Nal)CP(tBuGly)NR(Aib)GC (SEQ ID NO: 243);
ACAWGPFWCPVNRPGC (SEQ ID NO: 244);
ACPAGPFWCPVNRPGC (SEQ ID NO: 245);
ACPWAPFWCPVNRPGC (SEQ ID NO: 246);
ACPWGAFWCPVNRPGC (SEQ ID NO: 247);
ACPWGPFACPVNRPGC (SEQ ID NO: 248);
ACPWGPFWCAVNRPGC (SEQ ID NO: 249);
ACPWGPFWCPANRPGC (SEQ ID NO: 250);
ACPWGPFWCPVNAPGC (SEQ ID NO: 251);
AC(D-Ala)WGPFWCPVNRPGC (SEQ ID NO: 252);
ACP(D-Ala)GPFWCPVNRPGC (SEQ ID NO: 253);
ACPW(D-Ala)PFWCPVNRPGC (SEQ ID NO: 254);
ACPWG(D-Ala)FWCPVNRPGC (SEQ ID NO: 255);
ACPWGP(D-Ala)WCPVNRPGC (SEQ ID NO: 256);
ACPWGPF(D-Ala)CPVNRPGC (SEQ ID NO: 257);
ACPWGPFWC(D-Ala)VNRPGC (SEQ ID NO: 258);
ACPWGPFWCP(D-Ala)NRPGC (SEQ ID NO: 259);
ACPWGPFWCPVN(D-Ala)PGC (SEQ ID NO: 260);

ACPWAPFWCAVNRPGC (SEQ ID NO: 261); and
H(D-Asp)VPCP(1Nal)A(Aib)F(1Nal)CA(tBuGly)NR(Aib)(D-Asp)C (SEQ ID NO: 262);
or a pharmaceutically acceptable salt thereof.

2. The peptide ligand as defined in claim 1, wherein the peptide ligand is the free acid or a pharmaceutically acceptable salt selected from a sodium salt, a potassium salt, a calcium salt, and an ammonium salt.

3. The peptide ligand as defined in claim 1, wherein the EphA2 is human EphA2.

4. A pharmaceutical composition which comprises the peptide ligand as defined in claim 1, or a pharmaceutically acceptable salt thereof, in combination with one or more pharmaceutically acceptable excipients.

5. A peptide ligand specific for EphA2 comprising a polypeptide comprising at least three cysteine residues, separated by at least two loop sequences, and an aromatic molecular scaffold which forms covalent bonds with the cysteine residues of the polypeptide such that at least two polypeptide loops are formed on the molecular scaffold, wherein the molecular scaffold is 1,3,5-tris(bromomethyl)benzene (TBMB), and wherein the polypeptide comprises an amino acid sequence selected from:

Ac-CANDWLCSLGWTC (Ac-(SEQ ID NO: 23));
Ac-CMNDWLCALGWTC (Ac-(SEQ ID NO: 24));
Ac-CMNDWLCSAGWTC (Ac-(SEQ ID NO: 25));
Sar$_2$-ACPWGPFWCPVNRPGC (Sar$_2$-(SEQ ID NO: 52));
Ac-Sar$_2$-ACPWGPFWCPVNRPGC (Ac-Sar$_2$-(SEQ ID NO: 52));
(β-Ala)-Sar$_{10}$-ACPWGPFWCPVNRPGC ((β-Ala)-Sar$_{10}$-(SEQ ID NO: 52));
Sar$_2$-AC(HyP)WGPFWCPVNRPGC (Sar$_2$-(SEQ ID NO: 53));
Sar$_2$-AC(Aib)WGPFWCPVNRPGC (Sar$_2$-(SEQ ID NO: 54));
Sar$_2$-AC(4FlPro)WGPFWCPVNRPGC (Sar$_2$-(SEQ ID NO: 55));
Sar$_2$-ACP(1Nal)GPFWCPVNRPGC (Sar$_2$-(SEQ ID NO: 56));
Sar$_2$-ACP(2Nal)GPFWCPVNRPGC (Sar$_2$-(SEQ ID NO: 57));
Sar$_2$-ACPWG(Aze)FWCPVNRPGC (Sar$_2$-(SEQ ID NO: 58));
Sar$_2$-ACPWG(HyP)FWCPVNRPGC (Sar$_2$-(SEQ ID NO: 59));
Sar$_2$-ACPWG(Aib)FWCPVNRPGC (Sar$_2$-(SEQ ID NO: 60));
Sar$_2$-ACPWG(4FlPro)FWCPVNRPGC (Sar$_2$-(SEQ ID NO: 61));
Sar$_2$-ACPWG(Pip)FWCPVNRPGC (Sar$_2$-(SEQ ID NO: 62));
Sar$_2$-ACPWGPAWCPVNRPGC (Sar$_2$-(SEQ ID NO: 63));
Sar$_2$-ACPWGP(4Pal)WCPVNRPGC (Sar$_2$-(SEQ ID NO: 64));
Sar$_2$-ACPWGP(4BrPhe)WCPVNRPGC (Sar$_2$-(SEQ ID NO: 65));
Sar$_2$-ACPWGP(4MeOPhe)WCPVNRPGC (Sar$_2$-(SEQ ID NO: 66));
Sar$_2$-ACPWGP(HPhe)WCPVNRPGC (Sar$_2$-(SEQ ID NO: 67));
Sar$_2$-ACPWGP(4,4-BPA)WCPVNRPGC (Sar$_2$-(SEQ ID NO: 68));
Sar$_2$-ACPWGP(NO2Phe5)WCPVNRPGC (Sar$_2$-(SEQ ID NO: 69));
Sar$_2$-ACPWGP(3,4-DCPhe)WCPVNRPGC (Sar$_2$-(SEQ ID NO: 70));
Sar$_2$-ACPWGPYWCPVNRPGC (Sar$_2$-(SEQ ID NO: 71));
Sar$_2$-ACPWGP(3Pal)WCPVNRPGC (Sar$_2$-(SEQ ID NO: 72));
Sar$_2$-ACPWGP(Phg)WCPVNRPGC (Sar$_2$-(SEQ ID NO: 73));
Sar$_2$-ACPWGP(1Nal)WCPVNRPGC (Sar$_2$-(SEQ ID NO: 74));
Sar$_2$-ACPWGP(2Nal)WCPVNRPGC (Sar$_2$-(SEQ ID NO: 75));
Sar$_2$-ACPWGPF(1Nal)CPVNRPGC (Sar$_2$-(SEQ ID NO: 76));
Sar$_2$-ACPWGPFWC(Aze)VNRPGC (Sar$_2$-(SEQ ID NO: 77));
Sar$_2$-ACPWGPFWC(HyP)VNRPGC (Sar$_2$-(SEQ ID NO: 78));
Sar$_2$-ACPWGPFWC(4FlPro)VNRPGC (Sar$_2$-(SEQ ID NO: 79));
Sar$_2$-ACPWGPFWCP(tBuGly)NRPGC (Sar$_2$-(SEQ ID NO: 80));
Sar$_2$-ACPWGPFWCPVARPGC (Sar$_2$-(SEQ ID NO: 81));
Sar$_2$-ACPWGPFWCPV(D-Ala)RPGC (Sar$_2$-(SEQ ID NO: 82));
Sar$_2$-ACPWGPFWCPVN(HArg)PGC (Sar$_2$-(SEQ ID NO: 83));
Sar$_2$-ACPWGPFWCPVNRAGC (Sar$_2$-(SEQ ID NO: 84));
Sar$_2$-ACPWGPFWCPVNR(D-Ala)GC (Sar$_2$-(SEQ ID NO: 85));
Sar$_2$-ACPWGPFWCPVNR(Aze)GC (Sar$_2$-(SEQ ID NO: 86));
Sar$_2$-ACPWGPFWCPVNR(HyP)GC (Sar$_2$-(SEQ ID NO: 87));
Sar$_2$-ACPWGPFWCPVNR(Pip)GC (Sar$_2$-(SEQ ID NO: 88));
Sar$_2$-ACPWGPFWCPVNR(4FlPro)GC (Sar$_2$-(SEQ ID NO: 89));
Sar$_2$-ACPWGPFWCPVNR(Aib)GC (Sar$_2$-(SEQ ID NO: 90));
Sar$_2$-ACPWGPFWCPVNRPAC (Sar$_2$-(SEQ ID NO: 91));
Sar$_2$-ACPWGPFWCPVNRP(D-Ala)C (Sar$_2$-(SEQ ID NO: 92));
Sar$_2$-AC(Aib)(1Nal2)GPFWCPVNRPGC (Sar$_2$-(SEQ ID NO: 93));
Sar$_2$-AC(Aib)WGPF(1Nal)CPVNRPGC (Sar$_2$-(SEQ ID NO: 94));
Sar$_2$-ACP(1Nal)GPFWCPV(D-Ala)RPGC (Sar$_2$-(SEQ ID NO: 95));
Sar$_2$-ACP(1Nal)GPFWCPVNRP(D-Ala)C (Sar$_2$-(SEQ ID NO: 96));
Sar$_2$-ACPWGPF(1Nal)CPV(D-Ala)RPGC (Sar$_2$-(SEQ ID NO: 97));
Sar$_2$-ACPWGPF(1Nal)CPVNRP(D-Ala)C (Sar$_2$-(SEQ ID NO: 98));
Sar$_2$-ACP(1Nal)G(Aib)FWCPVNRPGC (Sar$_2$-(SEQ ID NO: 99));
Sar$_2$-ACP(1Nal)GPF(1Nal)CPVNRPGC (Sar$_2$-(SEQ ID NO: 100));
Sar$_2$-ACP(1Nal)GPFWCP(tBuGly)NRPGC (Sar$_2$-(SEQ ID NO: 101));
Sar$_2$-ACP(1Nal)GPFWCPVN(HArg)PGC (Sar$_2$-(SEQ ID NO: 102));
Sar$_2$-ACPWG(Aib)F(1Nal)CPVNRPGC (Sar$_2$-(SEQ ID NO: 103));

$Sar_2$-AC(Aib)(1Nal)GPFWCPV(D-Ala)RPGC ($Sar_2$-(SEQ ID NO: 104));
$Sar_2$-AC(Aib)(1Nal)GPFWCPVNRP(D-Ala)C ($Sar_2$-(SEQ ID NO: 105));
$Sar_2$-ACP(1Nal)G(Aib)FWCP(tBuGly)NRPGC ($Sar_2$-(SEQ ID NO: 106));
$Sar_2$-ACP(1Nal)G(Aib)FWCPV(D-Ala)RPGC ($Sar_2$-(SEQ ID NO: 107));
$Sar_2$-ACP(1Nal)G(Aib)FWCPVNRP(D-Ala)C ($Sar_2$-(SEQ ID NO: 108));
$Sar_2$-ACP(1Nal)GPFWCP(tBuGly)(D-Ala)RPGC ($Sar_2$-(SEQ ID NO: 109));
$Sar_2$-ACP(1Nal)GPFWCP(tBuGly)N(HArg)PGC ($Sar_2$-(SEQ ID NO: 110));
$Sar_2$-ACP(1Nal)GPFWCP(tBuGly)NR(Aib)GC ($Sar_2$-(SEQ ID NO: 111));
$Sar_2$-ACP(1Nal)GPFWCP(tBuGly)NRP(D-Ala)C ($Sar_2$-(SEQ ID NO: 112));
$Sar_2$-ACP(1Nal)GPFWCPV(D-Ala)(HArg)PGC ($Sar_2$-(SEQ ID NO: 113));
$Sar_2$-ACP(1Nal)GPFWCPVN(HArg)P(D-Ala)C ($Sar_2$-(SEQ ID NO: 114));
$Sar_2$-AC(Aib)(1Nal)G(Aib)FWCPVNR(Aib)GC ($Sar_2$-(SEQ ID NO: 115));
$Sar_2$-ACP(1Nal)G(Aib)FWCP(tBuGly)N(HArg)PGC ($Sar_2$-(SEQ ID NO: 116));
$Sar_2$-ACP(1Nal)G(Aib)FWCP(tBuGly)NR(Aib)GC ($Sar_2$-(SEQ ID NO: 117));
$Sar_2$-ACP(1Nal)GPFWCP(tBuGly)N(HArg)(Aib)GC ($Sar_2$-(SEQ ID NO: 118));
Ac-$Sar_2$-ADVH-CPWGPFWCPVNRPGC (Ac-$Sar_2$-(SEQ ID NO: 127));
Ac-$Sar_2$-ADVT-CPWGPFWCPVNRPGC (Ac-$Sar_2$-(SEQ ID NO: 136));
Ac-$Sar_2$-A(D-Asp)VT-CPWGPFWCPVNRPGC (Ac-$Sar_2$-(SEQ ID NO: 137));
Ac-$Sar_2$-A(D-Asp)(D-Asp)T-CPWGPFWCPVNRPGC (Ac-$Sar_2$-(SEQ ID NO: 138));
Ac-$Sar_2$-A(D-Asp)(Cba)T-CPWGPFWCPVNRPGC (Ac-$Sar_2$-(SEQ ID NO: 139));
Ac-$Sar_2$-A(D-Asp)(Cpa)T-CPWGPFWCPVNRPGC (Ac-$Sar_2$-(SEQ ID NO: 140));
Ac-$Sar_2$-A(D-Asp)(Cpg)T-CPWGPFWCPVNRPGC (Ac-$Sar_2$-(SEQ ID NO: 141));
Ac-$Sar_2$-A(D-Asp)(C5g)VT-CPWGPFWCPVNRPGC (Ac-$Sar_2$-(SEQ ID NO: 142));
Ac-$Sar_2$-AD(tBuGly)T-CPWGPFWCPVNRPGC (Ac-$Sar_2$-(SEQ ID NO: 143));
Ac-$Sar_2$-A(D-Asp)VT-C(AC3C)WGPFWCPVNRPGC (Ac-$Sar_2$-(SEQ ID NO: 144));
Ac-$Sar_2$-A(D-Asp)VT-C(AC4C)WGPFWCPVNRPGC (Ac-$Sar_2$-(SEQ ID NO: 145));
Ac-$Sar_2$-A(D-Asp)VT-C(AC5C)WGPFWCPVNRPGC (Ac-$Sar_2$-(SEQ ID NO: 146));
Ac-$Sar_2$-A(D-Asp)VT-C(4BenzyPro) WGPFWCPVNRPGC (Ac-$Sar_2$-(SEQ ID NO: 147));
Ac-$Sar_2$-A(D-Asp)VT-C(4PhenyPro) WGPFWCPVNRPGC (Ac-$Sar_2$-(SEQ ID NO: 148));
Ac-$Sar_2$-A(D-Asp)VT-CP(1Nal)GPFWCPVNRPGC (Ac-$Sar_2$-(SEQ ID NO: 149));
Ac-$Sar_2$-A(D-Asp)VT-CPWGP(HArg)WCPVNRPGC (Ac-$Sar_2$-(SEQ ID NO: 150));
Ac-$Sar_2$-A(D-Asp)VT-CPWGPNWCPVNRPGC (Ac-$Sar_2$-(SEQ ID NO: 151));
Ac-$Sar_2$-A(D-Asp)VT-CPWGPAWCPVNRPGC (Ac-$Sar_2$-(SEQ ID NO: 152));
Ac-$Sar_2$-A(D-Asp)VT-CPWGPFWCPLNRPGC (Ac-$Sar_2$-(SEQ ID NO: 153));
Ac-$Sar_2$-A(D-Asp)VT-CPWGPFWCPVNRP(D-Asp)C (Ac-$Sar_2$-(SEQ ID NO: 154));
Ac-$Sar_2$-A(D-Asp)VT-CPWGPFWCPVN(HArg)P(D-Asp)C (Ac-$Sar_2$-(SEQ ID NO: 155));
Ac-$Sar_2$-A(D-Asp)VT-CPWGPFWCPVNR(Aib)(D-Asp)C (Ac-$Sar_2$-(SEQ ID NO: 156));
Ac-$Sar_2$-A(D-Asp)VT-CP(1Nal)G(Aib)FWCPVNR(Aib)GC (Ac-$Sar_2$-(SEQ ID NO: 157));
Ac-$Sar_2$-A(D-Asp)VT-CPWG(Aib)F(1Nal)CPVNR(Aib)GC (Ac-$Sar_2$-(SEQ ID NO: 158));
Ac-$Sar_2$-A(D-Asp)VT-CPWG(Aib)FWCP(tBuGly)NR(Aib)GC (Ac-$Sar_2$-(SEQ ID NO: 159));
Ac-$Sar_2$-A(D-Asp)VT-CP(1Nal)G(Aib)F(1Nal)CPVNR(Aib)GC (Ac-$Sar_2$-(SEQ ID NO: 160));
Ac-$Sar_2$-A(D-Asp)VT-CP(1Nal)G(Aib)F(1Nal)CP(tBuGly)N(HArg)PGC (Ac-$Sar_2$-(SEQ ID NO: 161));
Ac-$Sar_2$-A(D-Asp)VT-CP(1Nal)G(Aib)F(1Nal)CP(tBuGly)NR(Aib)GC (Ac-$Sar_2$-(SEQ ID NO: 162));
Ac-$Sar_2$-A(D-Asp)VT-CP(1Nal)G(Aib)F(1Nal)CP(tBuGly)N(HArg)P(D-Asp)C (Ac-$Sar_2$-(SEQ ID NO: 163));
Ac-$Sar_2$-AHDVP-CPWGPFWCPVNRPGC (Ac-$Sar_2$-(SEQ ID NO: 172);
Ac-$Sar_2$-(D-Ala)HDVP-CPWGPFWCPVNRPGC (Ac-$Sar_2$-(SEQ ID NO: 173);
Ac-$Sar_2$-AADVP-CPWGPFWCPVNRPGC (Ac-$Sar_2$-(SEQ ID NO: 174);
Ac-$Sar_2$-A(D-His)DVP-CPWGPFWCPVNRPGC (Ac-$Sar_2$-(SEQ ID NO: 175);
$Sar_2$-A(D-His)DVP-CPWGPFWCPVNRPGC ($Sar_2$-(SEQ ID NO: 175);
Ac-$Sar_2$-A(D-His)DVCPWGPFWCPVNRPGC (Ac-$Sar_2$-(SEQ ID NO: 176);
$Sar_2$-A(D-Ala)DVP-CPWGPFWCPVNRPGC ($Sar_2$-(SEQ ID NO: 177);
Ac-$Sar_2$-A(D-Asp)DVP-CPWGPFWCPVNRPGC (Ac-$Sar_2$-(SEQ ID NO: 178);
$Sar_2$-A(Thi)DVP-CPWGPFWCPVNRPGC ($Sar_2$-(SEQ ID NO: 179);
$Sar_2$-A(ThiAz)DVP-CPWGPFWCPVNRPGC ($Sar_2$-(SEQ ID NO: 180);
$Sar_2$-A(2FuAla)DVP-CPWGPFWCPVNRPGC ($Sar_2$-(SEQ ID NO: 181);
Ac-$Sar_2$-A(D-His)D(tBuGly)P-CPWGPFWCPVNRPGC (Ac-$Sar_2$-(SEQ ID NO: 182);
$Sar_2$-AHAVP-CPWGPFWCPVNRPGC ($Sar_2$-(SEQ ID NO: 183);
$Sar_2$-AH(D-Ala)VP-CPWGPFWCPVNRPGC ($Sar_2$-(SEQ ID NO: 184);
$Sar_2$-AHEVP-CPWGPFWCPVNRPGC ($Sar_2$-(SEQ ID NO: 185);
$Sar_2$-AH(D-Glu)VP-CPWGPFWCPVNRPGC ($Sar_2$-(SEQ ID NO: 186);
$Sar_2$-AH(D-Asp)VP-CPWGPFWCPVNRPGC ($Sar_2$-(SEQ ID NO: 187);
Ac-$Sar_2$-AH(D-Asp)VP-CPWGPFWCPVNRPGC (Ac-$Sar_2$-(SEQ ID NO: 187);
Ac-$Sar_2$-AH(D-Asp)(tBuGly)P-CPWGPFWCPVNRPGC (Ac-$Sar_2$-(SEQ ID NO: 188);
Ac-$Sar_2$-AH(D-Asp)V(Sar)-CPWGPFWCPVNRPGC (Ac-$Sar_2$-(SEQ ID NO: 189);
Ac-$Sar_2$-AH(D-Asp)V(Aib)-CPWGPFWCPVNRPGC (Ac-$Sar_2$-(SEQ ID NO: 190);

Sar₂-AHDAP-CPWGPFWCPVNRPGC (Sar₂-(SEQ ID NO: 191));
Sar₂-AHD(D-Ala)P-CPWGPFWCPVNRPGC (Sar₂-(SEQ ID NO: 192);
Sar₂-AHD(Aib)P-CPWGPFWCPVNRPGC (Sar₂-(SEQ ID NO: 193);
Sar₂-AHD(tBuGly)P-CPWGPFWCPVNRPGC (Sar₂-(SEQ ID NO: 194);
Sar₂-AHDVA-CPWGPFWCPVNRPGC (Sar₂-(SEQ ID NO: 195);
Sar₂-AHDV(D-Ala)-CPWGPFWCPVNRPGC (Sar₂-(SEQ ID NO: 196);
Sar₂-AHDV(Aib)-CPWGPFWCPVNRPGC (Sar₂-(SEQ ID NO: 197);
Sar₂-AHDV(Aze)-CPWGPFWCPVNRPGC (Sar₂-(SEQ ID NO: 198);
Sar₂-AHDV(Pip)-CPWGPFWCPVNRPGC (Sar₂-(SEQ ID NO: 199);
(β-Ala)-Sar₁₀-HDVP-CPWGPFWCPVNRPGC ((β-Ala)-Sar₁₀-(SEQ ID NO: 200));
Ac-Sar₂-(D-His)DVP-CPWGPFWCPVNRPGC (Ac-Sar₂-(SEQ ID NO: 201));
Ac-Sar₂-H(D-Asp)VP-CPWGPFWCPVNRPGC (Ac-Sar₂-(SEQ ID NO: 202));
(β-Ala)-Sar₁₀-H(D-Asp)VP-CPWGPFWCPVNRPGC (β-Ala)-Sar₁₀-(SEQ ID NO: 202));
Ac-Sar₂-AH(D-Asp)VP-CP(1Nal)GPFWCP(tBuGly)N(HArg)PGC (Ac-Sar₂-(SEQ ID NO: 203));
Ac-Sar₂-A(D-His)DVP-CPWGP(ΨAla)WCPVNRPGC (Ac-Sar₂-(SEQ ID NO: 204));
Ac-Sar₂-A(D-His)DVP-CPWGPFWCP(HArg)NRPGC (Ac-Sar₂-(SEQ ID NO: 205));
Ac-Sar₂-A(D-His)DVP-CP(1Nal)GPFWCP(tBuGly)N(HArg)PGC (Ac-Sar₂-(SEQ ID NO: 206));
Ac-Sar₂-A(D-His)DVP-CP(1Nal)G(Aib)F(1Nal)CP(tBuGly)N(HArg)PGC (Ac-Sar₂-(SEQ ID NO: 207));
Ac-Sar₂-A(D-His)DVP-CP(1Nal)G(Aib)F(1Nal)CP(tBuGly)NR(Aib)GC (Ac-Sar₂-(SEQ ID NO: 208));
Ac-Sar₂-A(D-His)DVP-CPWG(Aib)FWCP(tBuGly)NR(Aib)GC (Ac-Sar₂-(SEQ ID NO: 209));
(β-Ala)-Sar₁₀-H(D-Asp)VP-C(Aib)(1Nal)G(Aib)F(1Nal)CP(tBuGly)NRPGC ((β-Ala)-Sar₁₀-(SEQ ID NO: 210));
(β-Ala)-Sar₁₀-H(D-Asp)VP-C(Aib)(1Nal)G(Aib)F(1Nal)CP(tBuGly)N(HArg)PGC ((β-Ala)-Sar₁₀-(SEQ ID NO: 211));
(β-Ala)-Sar₁₀-H(D-Asp)VP-C(Aib)(1Nal)G(Aib)F(1Nal)CP(tBuGly)N(HArg)P(D-Asp)C ((β-Ala)-Sar₁₀-(SEQ ID NO: 120));
Ac-(β-Ala)-Sar₁₀-H(D-Asp)VP-C(Aib)(1Nal)G(Aib)F(1Nal)CP(tBuGly)N(HArg)P(D-Asp)C (Ac-(β-Ala)-Sar₁₀-(SEQ ID NO: 120));
(β-Ala)-Sar₁₀-H(D-Asp)VP-C(Aib)(1Nal)G(Aib)F(1Nal)CP(tBuGly)N(HArg)(Aib)(D-Asp)C ((β-Ala)-Sar₁₀-(SEQ ID NO: 212));
(β-Ala)-Sar₁₀-H(D-Asp)VP-C(Aib)(1Nal)G(Aib)F(1Nal)CP(tBuGly)NR(Aib)GC ((β-Ala)-Sar₁₀-(SEQ ID NO: 213));
(β-Ala)-Sar₁₀-H(D-Asp)VP-C(Aib)(1Nal)G(Aib)F(1Nal)CP(tBuGly)NR(Aib)(D-Asp)C ((β-Ala)-Sar₁₀-(SEQ ID NO: 121));
Ac-(β-Ala)-Sar₁₀-H(D-Asp)VP-C(Aib)(1Nal)G(Aib)F(1Nal)CP(tBuGly)NR(Aib)(D-Asp)C (Ac-(β-Ala)-Sar₁₀-(SEQ ID NO: 121));
(β-Ala)-Sar₁₀-H(D-Asp)VP-C(Aib)(1Nal)G(Aib)FWCP(tBuGly)N(HArg)P(D-Asp)C ((β-Ala)-Sar₁₀-(SEQ ID NO: 214));
(β-Ala)-Sar₁₀-H(D-Asp)VP-C(Aib)(1Nal)GP(HArg)(1Nal)CP(tBuGly)NR(Aib)GC ((β-Ala)-Sar₁₀-(SEQ ID NO: 215));
(β-Ala)-Sar₁₀-H(D-Asp)VP-C(Aib)(1Nal)GP(HArg)(1Nal)CP(tBuGly)N(HArg)P(D-Asp)C ((β-Ala)-Sar₁₀-(SEQ ID NO: 216));
(β-Ala)-Sar₁₀-H(D-Asp)VP-C(Aib)WGP(HArg)(1Nal)CP(tBuGly)N(HArg)P(D-Asp)C ((β-Ala)-Sar₁₀-(SEQ ID NO: 217));
(β-Ala)-Sar₁₀-H(D-Asp)VP-C(Aib)WGP(HArg)WCP(tBuGly)N(HArg)P(D-Asp)C ((β-Ala)-Sar₁₀-(SEQ ID NO: 218));
(β-Ala)-Sar₁₀-H(D-Asp)VP-C(Aib)WGP(HArg)WCP(tBuGly)N(HArg)P(D-Asp)C ((β-Ala)-Sar₁₀-(SEQ ID NO: 218));
(β-Ala)-Sar₁₀-H(D-Asp)VP-C(D-Ala)(1Nal)G(Aib)F(1Nal)CP(tBuGly)N(HArg)P(D-Asp)C ((β-Ala)-Sar₁₀-(SEQ ID NO: 219));
(β-Ala)-Sar₁₀-H(D-Asp)VP-CP(1Nal)G(Aib)(HArg)(1Nal)CP(tBuGly)NR(Aib)GC ((β-Ala)-Sar₁₀-(SEQ ID NO: 220));
(β-Ala)-Sar₁₀-H(D-Asp)VP-CP(1Nal)G(Aib)(HArg)(1Nal)CP(tBuGly)NR(Aib)(D-Asp)C ((β-Ala)-Sar₁₀-(SEQ ID NO: 221));
(β-Ala)-Sar₁₀-H(D-Asp)VP-CP(1Nal)G(Aib)(HArg)(1Nal)CP(tBuGly)N(HArg)P(D-Asp)C ((β-Ala)-Sar₁₀-(SEQ ID NO: 222));
(β-Ala)-Sar₁₀-H(D-Asp)VP-CP(1Nal)G(Aib)F(1Nal)CP(tBuGly)NRPGC ((β-Ala)-Sar₁₀-(SEQ ID NO: 223));
Ac-Sar₂-H(D-Asp)VP-CP(1Nal)G(Aib)F(1Nal)CP(tBuGly)N(HArg)PGC (Ac-Sar₂-(SEQ ID NO: 224));
Ac-Sar₂-H(D-Asp)VP-CP(1Nal)G(Aib)F(1Nal)CP(tBuGly)N(HArg)P(D-Asp)C (Ac-Sar₂-(SEQ ID NO: 122));
(β-Ala)-Sar₁₀-H(D-Asp)VP-CP(1Nal)G(Aib)F(1Nal)CP(tBuGly)N(HArg)P(D-Asp)C ((β-Ala)-Sar₁₀-(SEQ ID NO: 122));
Ac-(β-Ala)-Sar₁₀-H(D-Asp)VP-CP(1Nal)G(Aib)F(1Nal)CP(tBuGly)N(HArg)P(D-Asp)C (Ac-(β-Ala)-Sar₁₀-(SEQ ID NO: 122));
(β-Ala)-Sar₁₀-H(D-Asp)VP-CP(1Nal)G(Aib)F(1Nal)CP(tBuGly)N(HArg)PGC ((β-Ala)-Sar₁₀-(SEQ ID NO: 224));
Ac-(β-Ala)-Sar₁₀-H(D-Asp)VP-CP(1Nal)G(Aib)F(1Nal)CP(tBuGly)NR(Aib)GC (Ac-(β-Ala)-Sar₁₀-(SEQ ID NO: 123));
(β-Ala)-Sar₁₀-H(D-Asp)VP-CP(1Nal)G(Aib)F(1Nal)CP(tBuGly)N(HArg)(Aib)(D-Asp)C ((β-Ala)-Sar₁₀-(SEQ ID NO: 225));
Ac-(β-Ala)-Sar₁₀-H(D-Asp)VP-CP(1Nal)G(Aib)F(1Nal)CP(tBuGly)NR(Aib)(D-Asp)C (Ac-(β-Ala)-Sar₁₀-(SEQ ID NO: 124));
Ac-Sar₂-H(D-Asp)VP-CP(1Nal)G(Aib)F(1Nal)CPVNR(Aib)GC (Ac-Sar₂-(SEQ ID NO: 226));
Ac-Sar₂-H(D-Asp)VP-CP(1Nal)G(Aib)F(1Nal)CP(tBuGly)NR(Aib)GC (Ac-Sar₂-(SEQ ID NO: 123));
(β-Ala)-Sar₁₀-H(D-Asp)VP-CP(1Nal)G(Aib)F(1Nal)CP(tBuGly)NR(Aib)GC ((β-Ala)-Sar₁₀-(SEQ ID NO: 123));
(β-Ala)-Sar₁₀-H(D-Asp)VP-CP(1Nal)G(Aib)F(1Nal)CP(tBuGly)NR(Aib)(D-Asp)C ((β-Ala)-Sar₁₀-(SEQ ID NO: 124));
(β-Ala)-Sar₁₀-H(D-Asp)VP-CP(1Nal)G(Aib)FWCP(tBuGly)N(HArg)P(D-Asp)C ((β-Ala)-Sar₁₀-(SEQ ID NO: 227));
Ac-Sar₂-H(D-Asp)VP-CP(1Nal)G(Aib)FWCPVNR(Aib)GC (Ac-Sar₂-(SEQ ID NO: 228));

Ac-Sar$_2$-H(D-Asp)VP-CPW(Aza-Gly)PFWCPVNRPGC (Ac-Sar$_2$-(SEQ ID NO: 229));
Ac-Sar$_2$-H(D-Asp)VP-CPWG(Aib)F(1Nal)CPVNR(Aib)GC (Ac-Sar$_2$-(SEQ ID NO: 230));
(β-Ala)-Sar$_{10}$-H(D-Asp)VP-CPWG(Aib)F(1Nal)CP(tBuGly)N(HArg)P(D-Asp)C ((β-Ala)-Sar$_{10}$-(SEQ ID NO: 231));
Ac-Sar$_2$-H(D-Asp)VP-CPWG(Aib)FWCP(tBuGly)NR(Aib)GC (Ac-Sar$_2$-(SEQ ID NO: 232));
(β-Ala)-Sar$_{10}$-H(D-Asp)VP-CPWG(Aib)FWCP(tBuGly)N(HArg)P(D-Asp)C ((β-Ala)-Sar$_{10}$-(SEQ ID NO: 233));
(β-Ala)-Sar$_{10}$-H(D-Asp)VP-CPWGP(HArg)WCP(tBuGly)N(HArg)P(D-Asp)C ((β-Ala)-Sar$_{10}$-(SEQ ID NO: 234));
(β-Ala)-Sar$_{10}$-H(D-Asp)(C5g)P-C(Aib)(1Nal)G(Aib)F(1Nal)CP(tBuGly)NR(Aib)(D-Asp)C ((β-Ala)-Sar$_{10}$-(SEQ ID NO: 125));
Ac-(β-Ala)-Sar$_{10}$-H(D-Asp)(C5g)P-C(Aib)(1Nal)G(Aib)F(1Nal)CP(tBuGly)NR(Aib)(D-Asp)C (Ac-(β-Ala)-Sar$_{10}$-(SEQ ID NO: 125));
(β-Ala)-Sar$_{10}$-H(D-Asp)(C5g)P-C(Aib)WG(Aib)FWCP(tBuGly)NR(Aib)(D-Asp)C ((β-Ala)-Sar$_{10}$-(SEQ ID NO: 235));
(β-Ala)-Sar$_{10}$-H(D-Asp)(C5g)P-CP(1Nal)G(Aib)F(1Nal)CP(tBuGly)N(HArg)P(D-Asp)C ((β-Ala)-Sar$_{10}$-(SEQ ID NO: 126));
Ac-(β-Ala)-Sar$_{10}$-H(D-Asp)(C5g)P-CP(1Nal)G(Aib)F(1Nal)CP(tBuGly)N(HArg)P(D-Asp)C (Ac-(β-Ala)-Sar$_{10}$-(SEQ ID NO: 126));
(β-Ala)-Sar$_{10}$-H(D-Asp)(C5g)P-CP(1Nal)G(Aib)F(1Nal)CP(tBuGly)NR(Aib)GC ((β-Ala)-Sar$_{10}$-(SEQ ID NO: 236));
(β-Ala)-Sar$_{10}$-H(D-Asp)(C5g)T-CP(1Nal)G(Aib)F(1Nal)CP(tBuGly)NR(Aib)GC ((β-Ala)-Sar$_{10}$-(SEQ ID NO: 237));
(β-Ala)-Sar$_{10}$-H(D-Asp)(C5g)T-CP(1Nal)G(Aib)F(1Nal)CP(tBuGly)N(HArg)P(D-Asp)C ((β-Ala)-Sar$_{10}$-(SEQ ID NO: 238));
Ac-Sar$_2$-A(D-Asp)DVT-CPWGPFWCPVNRPGC (Ac-Sar$_2$-(SEQ ID NO: 239));
Ac-Sar$_2$-A(D-Asp)DVT-CP(1Nal)GPFWCPVNRPGC (Ac-Sar$_2$-(SEQ ID NO: 240));
Ac-Sar$_2$-A(D-Asp)DVT-CP(1Nal)GPF(1Nal)CPVNRPGC (Ac-Sar$_2$-(SEQ ID NO: 241));
Ac-Sar$_2$-A(D-Asp)DVT-CP(1Nal)G(Aib)FWCP(tBuGly)N(HArg)PGC (Ac-Sar$_2$-(SEQ ID NO: 242));
Ac-Sar$_2$-H(D-Asp)VT-CP(1Nal)G(Aib)F(1Nal)CP(tBuGly)NR(Aib)GC (Ac-Sar$_2$-(SEQ ID NO: 243));
Ac-CANDWLCSLGWTC (Ac-(SEQ ID NO: 23));
Ac-CMNDWLCALGWTC (Ac-(SEQ ID NO: 24));
Ac-CMNDWLCSAGWTC (Ac-(SEQ ID NO: 25));
Sar$_2$-ACAWGPFWCPVNRPGC (Sar$_2$-(SEQ ID NO: 244));
Sar$_2$-ACPAGPFWCPVNRPGC (Sar$_2$-(SEQ ID NO: 245));
Sar$_2$-ACPWAPFWCPVNRPGC (Sar$_2$-(SEQ ID NO: 246));
Sar$_2$-ACPWGAFWCPVNRPGC (Sar$_2$-(SEQ ID NO: 247));
Sar$_2$-ACPWGPAWCPVNRPGC (Sar$_2$-(SEQ ID NO: 63));
Sar$_2$-ACPWGPFACPVNRPGC (Sar$_2$-(SEQ ID NO: 248));
Sar$_2$-ACPWGPFWCAVNRPGC (Sar$_2$-(SEQ ID NO: 249));
Sar$_2$-ACPWGPFWCPANRPGC (Sar$_2$-(SEQ ID NO: 250));
Sar$_2$-ACPWGPFWCPVARPGC (Sar$_2$-(SEQ ID NO: 81));
Sar$_2$-ACPWGPFWCPVNAPGC (Sar$_2$-(SEQ ID NO: 251));
Sar$_2$-ACPWGPFWCPVNRAGC (Sar$_2$-(SEQ ID NO: 84));
Sar$_2$-ACPWGPFWCPVNRPAC (Sar$_2$-(SEQ ID NO: 91));
Sar$_2$-AC(D-A1)WGPFWCPVNRPGC (Sar$_2$-(SEQ ID NO: 252));
Sar$_2$-ACP(D-Ala)GPFWCPVNRPGC (Sar$_2$-(SEQ ID NO: 253));
Sar$_2$-ACPW(D-Ala)PFWCPVNRPGC (Sar$_2$-(SEQ ID NO: 254));
Sar$_2$-ACPWG(D-Ala)FWCPVNRPGC (Sar$_2$-(SEQ ID NO: 255));
Sar$_2$-ACPWGP(D-Ala)WCPVNRPGC (Sar$_2$-(SEQ ID NO: 256));
Sar$_2$-ACPWGPF(D-Ala)CPVNRPGC (Sar$_2$-(SEQ ID NO: 257));
Sar$_2$-ACPWGPFWC(D-Ala)VNRPGC (Sar$_2$-(SEQ ID NO: 258));
Sar$_2$-ACPWGPFWCP(D-Ala)NRPGC (Sar$_2$-(SEQ ID NO: 259));
Sar$_2$-ACPWGPFWCPV(D-Ala)RPGC (Sar$_2$-(SEQ ID NO: 82));
Sar$_2$-ACPWGPFWCPVN(D-Ala)PGC (Sar$_2$-(SEQ ID NO: 260));
Sar$_2$-ACPWGPFWCPVNR(D-Ala)GC (Sar$_2$-(SEQ ID NO: 85));
Sar$_2$-ACPWGPFWCPVNRP(D-Ala)C (Sar$_2$-(SEQ ID NO: 92));
(β-Ala)-Sar$_{10}$-ACPWAPFWCAVNRPGC ((β-Ala)-Sar$_{10}$-(SEQ ID NO: 261));
Ac-Sar$_2$-A(D-Asp)VTCPWGPAWCPVNRPGC (Ac-Sar$_2$-(SEQ ID NO: 152)); and
(β-Ala)-Sar$_{10}$-H(D-Asp)VPCP(1Nal)A(Aib)F(1Nal)CA(tBuGly)NR(Aib)(D-Asp)C (β-Ala)-Sar$_{10}$-(SEQ ID NO: 262));
or a pharmaceutically acceptable salt thereof.

6. The peptide ligand as defined in claim 5, wherein the peptide ligand comprises an amino acid sequence selected from:
(β-Ala)-Sar$_{10}$-ACPWGPFWCPVNRPGC ((β-Ala)-Sar$_{10}$-(SEQ ID NO: 52));
(β-Ala)-Sar$_{10}$-H(D-Asp)VP-CPWGPFWCPVNRPGC ((β-Ala)-Sar$_{10}$-(SEQ ID NO: 202));
Ac-Sar$_2$-AH(D-Asp)VP-CP(1Nal)GPFWCP(tBuGly)N(HArg)PGC (Ac-Sar$_2$-(SEQ ID NO: 203)); and
(β-Ala)-Sar$_{10}$-ACPWAPFWCAVNRPGC ((β-Ala)-Sar$_{10}$-(SEQ ID NO: 261));
or a pharmaceutically acceptable salt thereof.

7. The peptide ligand as defined in claim 5, wherein the peptide ligand is the free acid or a pharmaceutically acceptable salt selected from a sodium salt, a potassium salt, a calcium salt, and an ammonium salt.

8. The peptide ligand as defined in claim 5, wherein the EphA2 is human EphA2.

9. A pharmaceutical composition which comprises the peptide ligand as defined in claim 5, or a pharmaceutically acceptable salt thereof, in combination with one or more pharmaceutically acceptable excipients.

* * * * *

SEQUENCE LISTING

<160> NUMBER OF SEQ ID NOS: 262

<210> SEQ ID NO 1
<211> LENGTH: 15
<212> TYPE: PRT
<213> ORGANISM: Artificial
<220> FEATURE:
<223> OTHER INFORMATION: Synthetic peptide

<400> SEQUENCE: 1

Ala Cys Met Asn Asp Trp Leu Cys Ser Leu Gly Trp Thr Cys Ala
1               5                   10                  15

<210> SEQ ID NO 2
<211> LENGTH: 14
<212> TYPE: PRT
<213> ORGANISM: Artificial
<220> FEATURE:
<223> OTHER INFORMATION: Synthetic peptide

<400> SEQUENCE: 2

```
Ala Cys Met Asn Asp Trp Leu Cys Ser Leu Gly Trp Thr Cys
1               5                   10
```

<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

```
Ala Cys Met Asn Asp Trp Leu Cys Glu Leu Gly Trp Thr Cys Ala
1               5                   10                  15
```

<210> SEQ ID NO 4
<211> LENGTH: 17
<212> TYPE: PRT
<213> ORGANISM: Artificial
<220> FEATURE:
<223> OTHER INFORMATION: Synthetic peptide

<400> SEQUENCE: 4

```
Ala Cys Thr Arg Gln Gly Ile Trp Cys Ala Leu Gly Phe Glu Pro Cys
1               5                   10                  15
Ala
```

<210> SEQ ID NO 5
<211> LENGTH: 15
<212> TYPE: PRT
<213> ORGANISM: Artificial
<220> FEATURE:
<223> OTHER INFORMATION: Synthetic peptide

<400> SEQUENCE: 5

```
Ala Cys Met Asn Asp Trp Leu Cys Thr Leu Gly Trp Ser Cys Ala
1               5                   10                  15
```

<210> SEQ ID NO 6
<211> LENGTH: 15
<212> TYPE: PRT
<213> ORGANISM: Artificial
<220> FEATURE:
<223> OTHER INFORMATION: Synthetic peptide

<400> SEQUENCE: 6

```
Ala Cys Met Asn Asp Trp Leu Cys Gln Leu Gly Trp Thr Cys Ala
1               5                   10                  15
```

<210> SEQ ID NO 7
<211> LENGTH: 15
<212> TYPE: PRT
<213> ORGANISM: Artificial
<220> FEATURE:
<223> OTHER INFORMATION: Synthetic peptide

<400> SEQUENCE: 7

```
Ala Cys Met Asn Asp Trp Leu Cys Thr Leu Gly Trp Thr Cys Ala
1               5                   10                  15
```

<210> SEQ ID NO 8
<211> LENGTH: 15
<212> TYPE: PRT
<213> ORGANISM: Artificial
<220> FEATURE:
<223> OTHER INFORMATION: Synthetic peptide

<400> SEQUENCE: 8

Ala Cys Met Asn Asp Trp Leu Cys Asp Leu Gly Trp Arg Cys Ala
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic peptide

<400> SEQUENCE: 9

Ala Cys Met Asn Asp Trp Leu Cys Glu Leu Gly Trp Ser Cys Ala
1               5                   10                  15

<210> SEQ ID NO 10
<211> LENGTH: 21
<212> TYPE: PRT
<213> ORGANISM: Artificial
<220> FEATURE:
<223> OTHER INFORMATION: Synthetic peptide

<400> SEQUENCE: 10

Ala Cys Arg Val Ser Pro Glu Tyr Cys Pro Phe Gly Pro Val Trp Cys
1               5                   10                  15

Ala Gly Ala Ala Ala
            20

<210> SEQ ID NO 11
<211> LENGTH: 17
<212> TYPE: PRT
<213> ORGANISM: Artificial
<220> FEATURE:
<223> OTHER INFORMATION: Synthetic peptide

<400> SEQUENCE: 11

Ala Cys Pro Trp Gly Pro Ala Trp Cys Pro Val His Gly Lys Thr Cys
1               5                   10                  15

Ala

<210> SEQ ID NO 12
<211> LENGTH: 17
<212> TYPE: PRT
<213> ORGANISM: Artificial
<220> FEATURE:
<223> OTHER INFORMATION: Synthetic peptide

<400> SEQUENCE: 12

Ala Cys Pro Trp Gly Pro Ala Trp Cys Pro Val Asn Arg Pro Gly Cys
1               5                   10                  15

Ala

<210> SEQ ID NO 13
<211> LENGTH: 21
<212> TYPE: PRT
<213> ORGANISM: Artificial
<220> FEATURE:
<223> OTHER INFORMATION: Synthetic peptide

<400> SEQUENCE: 13

Ala Cys Pro Trp Gly Pro Ala Trp Cys Pro Val Asn Arg Pro Gly Cys
1               5                   10                  15

Ala Gly Ala Ala Ala
            20

```
<210> SEQ ID NO 14
<211> LENGTH: 17
<212> TYPE: PRT
<213> ORGANISM: Artificial
<220> FEATURE:
<223> OTHER INFORMATION: Synthetic peptide

<400> SEQUENCE: 14

Ala Cys Pro Trp Gly Pro Met Trp Cys Pro Val Asn Arg Pro Gly Cys
1               5                   10                  15

Ala

<210> SEQ ID NO 15
<211> LENGTH: 17
<212> TYPE: PRT
<213> ORGANISM: Artificial
<220> FEATURE:
<223> OTHER INFORMATION: Synthetic peptide

<400> SEQUENCE: 15

Ala Cys Pro Trp Gly Pro Asn Trp Cys Pro Val Asn Arg Pro Gly Cys
1               5                   10                  15

Ala

<210> SEQ ID NO 16
<211> LENGTH: 21
<212> TYPE: PRT
<213> ORGANISM: Artificial
<220> FEATURE:
<223> OTHER INFORMATION: Synthetic peptide

<400> SEQUENCE: 16

Ala Gly Glu Met Ala Cys Pro Trp Gly Pro Phe Trp Cys Pro Val Asn
1               5                   10                  15

Arg Pro Gly Cys Ala
            20

<210> SEQ ID NO 17
<211> LENGTH: 20
<212> TYPE: PRT
<213> ORGANISM: Artificial
<220> FEATURE:
<223> OTHER INFORMATION: Synthetic peptide

<400> SEQUENCE: 17

Ala Asp Val Thr Cys Pro Trp Gly Pro Phe Trp Cys Pro Val Asn Arg
1               5                   10                  15

Pro Gly Cys Ala
            20

<210> SEQ ID NO 18
<211> LENGTH: 21
<212> TYPE: PRT
<213> ORGANISM: Artificial
<220> FEATURE:
<223> OTHER INFORMATION: Synthetic peptide

<400> SEQUENCE: 18

Ala Asp Val Arg Thr Cys Pro Trp Gly Pro Phe Trp Cys Pro Val Asn
1               5                   10                  15

Arg Pro Gly Cys Ala
            20
```

```
<210> SEQ ID NO 19
<211> LENGTH: 21
<212> TYPE: PRT
<213> ORGANISM: Artificial
<220> FEATURE:
<223> OTHER INFORMATION: Synthetic peptide

<400> SEQUENCE: 19

Ala Asn Asp Val Thr Cys Pro Trp Gly Pro Phe Trp Cys Pro Val Asn
1               5                   10                  15

Arg Pro Gly Cys Ala
            20

<210> SEQ ID NO 20
<211> LENGTH: 17
<212> TYPE: PRT
<213> ORGANISM: Artificial
<220> FEATURE:
<223> OTHER INFORMATION: Synthetic peptide

<400> SEQUENCE: 20

Ala Cys Val Pro Gln Gly Ile Trp Cys Ala Leu Gln Phe Glu Pro Cys
1               5                   10                  15

Ala

<210> SEQ ID NO 21
<211> LENGTH: 17
<212> TYPE: PRT
<213> ORGANISM: Artificial
<220> FEATURE:
<223> OTHER INFORMATION: Synthetic peptide

<400> SEQUENCE: 21

Ala Cys Gln Lys Gln Gly Leu Trp Cys Ala Leu Gly Phe Glu Pro Cys
1               5                   10                  15

Ala

<210> SEQ ID NO 22
<211> LENGTH: 15
<212> TYPE: PRT
<213> ORGANISM: Artificial
<220> FEATURE:
<223> OTHER INFORMATION: Synthetic peptide

<400> SEQUENCE: 22

Ala Cys Leu Val Asn Asp Asp Cys Phe Tyr Met Gly Leu Cys Ala
1               5                   10                  15

<210> SEQ ID NO 23
<211> LENGTH: 13
<212> TYPE: PRT
<213> ORGANISM: Artificial
<220> FEATURE:
<223> OTHER INFORMATION: Synthetic peptide

<400> SEQUENCE: 23

Cys Ala Asn Asp Trp Leu Cys Ser Leu Gly Trp Thr Cys
1               5                   10

<210> SEQ ID NO 24
<211> LENGTH: 13
<212> TYPE: PRT
<213> ORGANISM: Artificial
<220> FEATURE:
<223> OTHER INFORMATION: Synthetic peptide
```

```
<400> SEQUENCE: 24

Cys Met Asn Asp Trp Leu Cys Ala Leu Gly Trp Thr Cys
1               5                  10

<210> SEQ ID NO 25
<211> LENGTH: 13
<212> TYPE: PRT
<213> ORGANISM: Artificial
<220> FEATURE:
<223> OTHER INFORMATION: Synthetic peptide

<400> SEQUENCE: 25

Cys Met Asn Asp Trp Leu Cys Ser Ala Gly Trp Thr Cys
1               5                  10

<210> SEQ ID NO 26
<211> LENGTH: 15
<212> TYPE: PRT
<213> ORGANISM: Artificial
<220> FEATURE:
<223> OTHER INFORMATION: Synthetic peptide

<400> SEQUENCE: 26

Ala Cys Met Asn Asp Trp Leu Cys Gln Leu Gly Trp Lys Cys Ala
1               5                  10                  15

<210> SEQ ID NO 27
<211> LENGTH: 16
<212> TYPE: PRT
<213> ORGANISM: Artificial
<220> FEATURE:
<223> OTHER INFORMATION: Synthetic peptide

<400> SEQUENCE: 27

Ala Cys Thr Gln Asn Asp Trp Leu Cys Ser Leu Gly Trp Thr Cys Ala
1               5                  10                  15

<210> SEQ ID NO 28
<211> LENGTH: 17
<212> TYPE: PRT
<213> ORGANISM: Artificial
<220> FEATURE:
<223> OTHER INFORMATION: Synthetic peptide

<400> SEQUENCE: 28

Ala Cys Arg Asn Ile Pro Thr Met Cys Pro Phe Gly Pro Val Trp Cys
1               5                  10                  15

Ala

<210> SEQ ID NO 29
<211> LENGTH: 17
<212> TYPE: PRT
<213> ORGANISM: Artificial
<220> FEATURE:
<223> OTHER INFORMATION: Synthetic peptide

<400> SEQUENCE: 29

Ala Cys Arg Val Ser Pro Glu Tyr Cys Pro Phe Gly Pro Val Trp Cys
1               5                  10                  15

Ala

<210> SEQ ID NO 30
<211> LENGTH: 17
<212> TYPE: PRT
<213> ORGANISM: Artificial
```

```
<220> FEATURE:
<223> OTHER INFORMATION: Synthetic peptide

<400> SEQUENCE: 30

Ala Cys Arg Val Ser Pro Glu Tyr Cys Pro Phe Gly Pro Thr Trp Cys
1               5                   10                  15
Ala

<210> SEQ ID NO 31
<211> LENGTH: 17
<212> TYPE: PRT
<213> ORGANISM: Artificial
<220> FEATURE:
<223> OTHER INFORMATION: Synthetic peptide

<400> SEQUENCE: 31

Ala Cys Arg Val Ser Pro Glu Tyr Cys Pro Phe Gly Pro Ser Trp Cys
1               5                   10                  15
Ala

<210> SEQ ID NO 32
<211> LENGTH: 17
<212> TYPE: PRT
<213> ORGANISM: Artificial
<220> FEATURE:
<223> OTHER INFORMATION: Synthetic peptide

<400> SEQUENCE: 32

Ala Cys Arg Val Ser Pro Glu Tyr Cys Pro Phe Gly Pro Glu Trp Cys
1               5                   10                  15
Ala

<210> SEQ ID NO 33
<211> LENGTH: 17
<212> TYPE: PRT
<213> ORGANISM: Artificial
<220> FEATURE:
<223> OTHER INFORMATION: Synthetic peptide

<400> SEQUENCE: 33

Ala Cys Arg Val Ser Pro Glu Tyr Cys Pro Phe Gly Pro Tyr Trp Cys
1               5                   10                  15
Ala

<210> SEQ ID NO 34
<211> LENGTH: 17
<212> TYPE: PRT
<213> ORGANISM: Artificial
<220> FEATURE:
<223> OTHER INFORMATION: Synthetic peptide

<400> SEQUENCE: 34

Ala Cys Arg Val Ser Pro Glu Tyr Cys Pro Phe Gly Pro Leu Trp Cys
1               5                   10                  15
Ala

<210> SEQ ID NO 35
<211> LENGTH: 17
<212> TYPE: PRT
<213> ORGANISM: Artificial
<220> FEATURE:
<223> OTHER INFORMATION: Synthetic peptide

<400> SEQUENCE: 35
```

```
Ala Cys Arg Val Ser Pro Glu Tyr Cys Pro Phe Gly Pro Asp Trp Cys
1               5                   10                  15

Ala

<210> SEQ ID NO 36
<211> LENGTH: 17
<212> TYPE: PRT
<213> ORGANISM: Artificial
<220> FEATURE:
<223> OTHER INFORMATION: Synthetic peptide

<400> SEQUENCE: 36

Ala Cys Pro Trp Gly Pro Ala Trp Cys Pro Val Arg Asp Thr Asn Cys
1               5                   10                  15

Ala

<210> SEQ ID NO 37
<211> LENGTH: 17
<212> TYPE: PRT
<213> ORGANISM: Artificial
<220> FEATURE:
<223> OTHER INFORMATION: Synthetic peptide

<400> SEQUENCE: 37

Ala Cys Pro Trp Gly Pro Ala Trp Cys Pro Val Asn Gly Ala Arg Cys
1               5                   10                  15

Ala

<210> SEQ ID NO 38
<211> LENGTH: 16
<212> TYPE: PRT
<213> ORGANISM: Artificial
<220> FEATURE:
<223> OTHER INFORMATION: Synthetic peptide

<400> SEQUENCE: 38

Ala Cys Pro Trp Gly Pro Ala Trp Cys Pro Val Arg Asn Pro Cys Ala
1               5                   10                  15

<210> SEQ ID NO 39
<211> LENGTH: 16
<212> TYPE: PRT
<213> ORGANISM: Artificial
<220> FEATURE:
<223> OTHER INFORMATION: Synthetic peptide

<400> SEQUENCE: 39

Ala Cys Pro Trp Gly Pro Ala Trp Cys Pro Val Ser Arg Val Cys Ala
1               5                   10                  15

<210> SEQ ID NO 40
<211> LENGTH: 15
<212> TYPE: PRT
<213> ORGANISM: Artificial
<220> FEATURE:
<223> OTHER INFORMATION: Synthetic peptide

<400> SEQUENCE: 40

Ala Cys Pro Trp Gly Pro Ala Trp Cys Pro Val Arg Ser Cys Ala
1               5                   10                  15

<210> SEQ ID NO 41
<211> LENGTH: 16
<212> TYPE: PRT
```

```
<213> ORGANISM: Artificial
<220> FEATURE:
<223> OTHER INFORMATION: Synthetic peptide

<400> SEQUENCE: 41

Ala Cys Pro Trp Gly Pro Ala Trp Cys Pro Val Lys Pro Thr Cys Ala
1               5                   10                  15

<210> SEQ ID NO 42
<211> LENGTH: 17
<212> TYPE: PRT
<213> ORGANISM: Artificial
<220> FEATURE:
<223> OTHER INFORMATION: Synthetic peptide

<400> SEQUENCE: 42

Ala Cys Pro Trp Gly Pro Ala Trp Cys Pro Val Asn Arg Asn Gly Cys
1               5                   10                  15

Ala

<210> SEQ ID NO 43
<211> LENGTH: 21
<212> TYPE: PRT
<213> ORGANISM: Artificial
<220> FEATURE:
<223> OTHER INFORMATION: Synthetic peptide

<400> SEQUENCE: 43

Ala Val His Ile Pro Cys Pro Trp Gly Pro Ser Trp Cys Pro Val Asn
1               5                   10                  15

Arg Pro Gly Cys Ala
            20

<210> SEQ ID NO 44
<211> LENGTH: 21
<212> TYPE: PRT
<213> ORGANISM: Artificial
<220> FEATURE:
<223> OTHER INFORMATION: Synthetic peptide

<400> SEQUENCE: 44

Ala Glu Gly Leu Pro Cys Pro Trp Gly Pro Phe Trp Cys Pro Val Asn
1               5                   10                  15

Arg Pro Gly Cys Ala
            20

<210> SEQ ID NO 45
<211> LENGTH: 20
<212> TYPE: PRT
<213> ORGANISM: Artificial
<220> FEATURE:
<223> OTHER INFORMATION: Synthetic peptide

<400> SEQUENCE: 45

Ala Asp His Ala Cys Pro Trp Gly Pro Phe Trp Cys Pro Val Asn Arg
1               5                   10                  15

Pro Gly Cys Ala
            20

<210> SEQ ID NO 46
<211> LENGTH: 20
<212> TYPE: PRT
<213> ORGANISM: Artificial
<220> FEATURE:
<223> OTHER INFORMATION: Synthetic peptide
```

```
<400> SEQUENCE: 46

Ala Asp Val His Cys Pro Trp Gly Pro Phe Trp Cys Pro Val Asn Arg
1               5                   10                  15

Pro Gly Cys Ala
            20

<210> SEQ ID NO 47
<211> LENGTH: 21
<212> TYPE: PRT
<213> ORGANISM: Artificial
<220> FEATURE:
<223> OTHER INFORMATION: Synthetic peptide

<400> SEQUENCE: 47

Ala His Asp Val Pro Cys Pro Trp Gly Pro Phe Trp Cys Pro Val Asn
1               5                   10                  15

Arg Pro Gly Cys Ala
            20

<210> SEQ ID NO 48
<211> LENGTH: 21
<212> TYPE: PRT
<213> ORGANISM: Artificial
<220> FEATURE:
<223> OTHER INFORMATION: Synthetic peptide

<400> SEQUENCE: 48

Ala Arg Asp Asp Pro Cys Pro Trp Gly Pro Phe Trp Cys Pro Val Asn
1               5                   10                  15

Arg Pro Gly Cys Ala
            20

<210> SEQ ID NO 49
<211> LENGTH: 17
<212> TYPE: PRT
<213> ORGANISM: Artificial
<220> FEATURE:
<223> OTHER INFORMATION: Synthetic peptide

<400> SEQUENCE: 49

Ala Cys Thr Thr Gly Ser Ile Trp Cys Ala Leu Gln Phe Glu Pro Cys
1               5                   10                  15

Ala

<210> SEQ ID NO 50
<211> LENGTH: 17
<212> TYPE: PRT
<213> ORGANISM: Artificial
<220> FEATURE:
<223> OTHER INFORMATION: Synthetic peptide

<400> SEQUENCE: 50

Ala Cys Val Pro Gln Gly Ile Trp Cys Ala Leu Arg Tyr Glu Pro Cys
1               5                   10                  15

Ala

<210> SEQ ID NO 51
<211> LENGTH: 17
<212> TYPE: PRT
<213> ORGANISM: Artificial
<220> FEATURE:
<223> OTHER INFORMATION: Synthetic peptide
```

<400> SEQUENCE: 51

Ala Cys Pro Trp Gly Pro Phe Trp Cys Pro Val Asn Arg Pro Gly Cys
1               5                   10                  15

Ala

<210> SEQ ID NO 52
<211> LENGTH: 16
<212> TYPE: PRT
<213> ORGANISM: Artificial
<220> FEATURE:
<223> OTHER INFORMATION: Synthetic peptide

<400> SEQUENCE: 52

Ala Cys Pro Trp Gly Pro Phe Trp Cys Pro Val Asn Arg Pro Gly Cys
1               5                   10                  15

<210> SEQ ID NO 53
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is HyP

<400> SEQUENCE: 53

Ala Cys Xaa Trp Gly Pro Phe Trp Cys Pro Val Asn Arg Pro Gly Cys
1               5                   10                  15

<210> SEQ ID NO 54
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is Aib

<400> SEQUENCE: 54

Ala Cys Xaa Trp Gly Pro Phe Trp Cys Pro Val Asn Arg Pro Gly Cys
1               5                   10                  15

<210> SEQ ID NO 55
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is 4FlPro

<400> SEQUENCE: 55

Ala Cys Xaa Trp Gly Pro Phe Trp Cys Pro Val Asn Arg Pro Gly Cys
1               5                   10                  15

<210> SEQ ID NO 56
<211> LENGTH: 16
<212> TYPE: PRT
<213> ORGANISM: Artificial
<220> FEATURE:
<223> OTHER INFORMATION: Synthetic peptide
<220> FEATURE:

```
<221> NAME/KEY: Xaa
<222> LOCATION: (4)..(4)
<223> OTHER INFORMATION: Xaa is 1Nal

<400> SEQUENCE: 56

Ala Cys Pro Xaa Gly Pro Phe Trp Cys Pro Val Asn Arg Pro Gly Cys
1               5                   10                  15

<210> SEQ ID NO 57
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 2Nal

<400> SEQUENCE: 57

Ala Cys Pro Xaa Gly Pro Phe Trp Cys Pro Val Asn Arg Pro Gly Cys
1               5                   10                  15

<210> SEQ ID NO 58
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is Aze

<400> SEQUENCE: 58

Ala Cys Pro Trp Gly Xaa Phe Trp Cys Pro Val Asn Arg Pro Gly Cys
1               5                   10                  15

<210> SEQ ID NO 59
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is HyP

<400> SEQUENCE: 59

Ala Cys Pro Trp Gly Xaa Phe Trp Cys Pro Val Asn Arg Pro Gly Cys
1               5                   10                  15

<210> SEQ ID NO 60
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is Aib

<400> SEQUENCE: 60

Ala Cys Pro Trp Gly Xaa Phe Trp Cys Pro Val Asn Arg Pro Gly Cys
1               5                   10                  15

<210> SEQ ID NO 61
```

```
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is 4FlPro

<400> SEQUENCE: 61

Ala Cys Pro Trp Gly Xaa Phe Trp Cys Pro Val Asn Arg Pro Gly Cys
1               5                   10                  15

<210> SEQ ID NO 62
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is Pip

<400> SEQUENCE: 62

Ala Cys Pro Trp Gly Xaa Phe Trp Cys Pro Val Asn Arg Pro Gly Cys
1               5                   10                  15

<210> SEQ ID NO 63
<211> LENGTH: 16
<212> TYPE: PRT
<213> ORGANISM: Artificial
<220> FEATURE:
<223> OTHER INFORMATION: Synthetic peptide

<400> SEQUENCE: 63

Ala Cys Pro Trp Gly Pro Ala Trp Cys Pro Val Asn Arg Pro Gly Cys
1               5                   10                  15

<210> SEQ ID NO 64
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is 4Pal

<400> SEQUENCE: 64

Ala Cys Pro Trp Gly Pro Xaa Trp Cys Pro Val Asn Arg Pro Gly Cys
1               5                   10                  15

<210> SEQ ID NO 65
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is 4BrPhe

<400> SEQUENCE: 65

Ala Cys Pro Trp Gly Pro Xaa Trp Cys Pro Val Asn Arg Pro Gly Cys
1               5                   10                  15
```

<210> SEQ ID NO 66
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is 4MeOPhe

<400> SEQUENCE: 66

Ala Cys Pro Trp Gly Pro Xaa Trp Cys Pro Val Asn Arg Pro Gly Cys
1               5                   10                  15

<210> SEQ ID NO 67
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is HPhe

<400> SEQUENCE: 67

Ala Cys Pro Trp Gly Pro Xaa Trp Cys Pro Val Asn Arg Pro Gly Cys
1               5                   10                  15

<210> SEQ ID NO 68
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is 4,4-BPA

<400> SEQUENCE: 68

Ala Cys Pro Trp Gly Pro Xaa Trp Cys Pro Val Asn Arg Pro Gly Cys
1               5                   10                  15

<210> SEQ ID NO 69
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is NO2Phe5

<400> SEQUENCE: 69

Ala Cys Pro Trp Gly Pro Xaa Trp Cys Pro Val Asn Arg Pro Gly Cys
1               5                   10                  15

<210> SEQ ID NO 70
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is 3,4-DCPhe

<400> SEQUENCE: 70

Ala Cys Pro Trp Gly Pro Xaa Trp Cys Pro Val Asn Arg Pro Gly Cys
1               5                   10                  15

<210> SEQ ID NO 71
<211> LENGTH: 16
<212> TYPE: PRT
<213> ORGANISM: Artificial
<220> FEATURE:
<223> OTHER INFORMATION: Synthetic peptide

<400> SEQUENCE: 71

Ala Cys Pro Trp Gly Pro Tyr Trp Cys Pro Val Asn Arg Pro Gly Cys
1               5                   10                  15

<210> SEQ ID NO 72
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is 3PaI

<400> SEQUENCE: 72

Ala Cys Pro Trp Gly Pro Xaa Trp Cys Pro Val Asn Arg Pro Gly Cys
1               5                   10                  15

<210> SEQ ID NO 73
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is Phg

<400> SEQUENCE: 73

Ala Cys Pro Trp Gly Pro Xaa Trp Cys Pro Val Asn Arg Pro Gly Cys
1               5                   10                  15

<210> SEQ ID NO 74
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is 1Nal

<400> SEQUENCE: 74

Ala Cys Pro Trp Gly Pro Xaa Trp Cys Pro Val Asn Arg Pro Gly Cys
1               5                   10                  15

<210> SEQ ID NO 75
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa

```
<222> LOCATION: (7)..(7)
<223> OTHER INFORMATION: Xaa is 2Nal

<400> SEQUENCE: 75

Ala Cys Pro Trp Gly Pro Xaa Trp Cys Pro Val Asn Arg Pro Gly Cys
1               5                   10                  15

<210> SEQ ID NO 76
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (8)..(8)
<223> OTHER INFORMATION: Xaa is 1Nal

<400> SEQUENCE: 76

Ala Cys Pro Trp Gly Pro Phe Xaa Cys Pro Val Asn Arg Pro Gly Cys
1               5                   10                  15

<210> SEQ ID NO 77
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (10)..(10)
<223> OTHER INFORMATION: Xaa is Aze

<400> SEQUENCE: 77

Ala Cys Pro Trp Gly Pro Phe Trp Cys Xaa Val Asn Arg Pro Gly Cys
1               5                   10                  15

<210> SEQ ID NO 78
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (10)..(10)
<223> OTHER INFORMATION: Xaa is HyP

<400> SEQUENCE: 78

Ala Cys Pro Trp Gly Pro Phe Trp Cys Xaa Val Asn Arg Pro Gly Cys
1               5                   10                  15

<210> SEQ ID NO 79
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (10)..(10)
<223> OTHER INFORMATION: Xaa is 4FlPro

<400> SEQUENCE: 79

Ala Cys Pro Trp Gly Pro Phe Trp Cys Xaa Val Asn Arg Pro Gly Cys
1               5                   10                  15

<210> SEQ ID NO 80
<211> LENGTH: 16
```

<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (11)..(11)
<223> OTHER INFORMATION: Xaa is tBuGly

<400> SEQUENCE: 80

Ala Cys Pro Trp Gly Pro Phe Trp Cys Pro Xaa Asn Arg Pro Gly Cys
1               5                   10                  15

<210> SEQ ID NO 81
<211> LENGTH: 16
<212> TYPE: PRT
<213> ORGANISM: Artificial
<220> FEATURE:
<223> OTHER INFORMATION: Synthetic peptide

<400> SEQUENCE: 81

Ala Cys Pro Trp Gly Pro Phe Trp Cys Pro Val Ala Arg Pro Gly Cys
1               5                   10                  15

<210> SEQ ID NO 82
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (12)..(12)
<223> OTHER INFORMATION: Xaa is D-Ala

<400> SEQUENCE: 82

Ala Cys Pro Trp Gly Pro Phe Trp Cys Pro Val Xaa Arg Pro Gly Cys
1               5                   10                  15

<210> SEQ ID NO 83
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (13)..(13)
<223> OTHER INFORMATION: Xaa is HArg

<400> SEQUENCE: 83

Ala Cys Pro Trp Gly Pro Phe Trp Cys Pro Val Asn Xaa Pro Gly Cys
1               5                   10                  15

<210> SEQ ID NO 84
<211> LENGTH: 16
<212> TYPE: PRT
<213> ORGANISM: Artificial
<220> FEATURE:
<223> OTHER INFORMATION: Synthetic peptide

<400> SEQUENCE: 84

Ala Cys Pro Trp Gly Pro Phe Trp Cys Pro Val Asn Arg Ala Gly Cys
1               5                   10                  15

<210> SEQ ID NO 85
<211> LENGTH: 16
<212> TYPE: PRT
<213> ORGANISM: Artificial

```
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is D-Ala

<400> SEQUENCE: 85

Ala Cys Pro Trp Gly Pro Phe Trp Cys Pro Val Asn Arg Xaa Gly Cys
1               5                   10                  15

<210> SEQ ID NO 86
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Aze

<400> SEQUENCE: 86

Ala Cys Pro Trp Gly Pro Phe Trp Cys Pro Val Asn Arg Xaa Gly Cys
1               5                   10                  15

<210> SEQ ID NO 87
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is HyP

<400> SEQUENCE: 87

Ala Cys Pro Trp Gly Pro Phe Trp Cys Pro Val Asn Arg Xaa Gly Cys
1               5                   10                  15

<210> SEQ ID NO 88
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Pip

<400> SEQUENCE: 88

Ala Cys Pro Trp Gly Pro Phe Trp Cys Pro Val Asn Arg Xaa Gly Cys
1               5                   10                  15

<210> SEQ ID NO 89
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is 4FlPro

<400> SEQUENCE: 89

Ala Cys Pro Trp Gly Pro Phe Trp Cys Pro Val Asn Arg Xaa Gly Cys
1               5                   10                  15
```

<210> SEQ ID NO 90
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Aib

<400> SEQUENCE: 90

Ala Cys Pro Trp Gly Pro Phe Trp Cys Pro Val Asn Arg Xaa Gly Cys
1               5                   10                  15

<210> SEQ ID NO 91
<211> LENGTH: 16
<212> TYPE: PRT
<213> ORGANISM: Artificial
<220> FEATURE:
<223> OTHER INFORMATION: Synthetic peptide

<400> SEQUENCE: 91

Ala Cys Pro Trp Gly Pro Phe Trp Cys Pro Val Asn Arg Pro Ala Cys
1               5                   10                  15

<210> SEQ ID NO 92
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is D-Ala

<400> SEQUENCE: 92

Ala Cys Pro Trp Gly Pro Phe Trp Cys Pro Val Asn Arg Pro Xaa Cys
1               5                   10                  15

<210> SEQ ID NO 93
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is Aib
<220> FEATURE:
<221> NAME/KEY: Xaa
<222> LOCATION: (4)..(4)
<223> OTHER INFORMATION: Xaa is 1Nal2

<400> SEQUENCE: 93

Ala Cys Xaa Xaa Gly Pro Phe Trp Cys Pro Val Asn Arg Pro Gly Cys
1               5                   10                  15

<210> SEQ ID NO 94
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)

<223> OTHER INFORMATION: Xaa is Aib
<220> FEATURE:
<221> NAME/KEY: Xaa
<222> LOCATION: (8)..(8)
<223> OTHER INFORMATION: Xaa is 1Nal

<400> SEQUENCE: 94

Ala Cys Xaa Trp Gly Pro Phe Xaa Cys Pro Val Asn Arg Pro Gly Cys
1               5                   10                  15

<210> SEQ ID NO 95
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (12)..(12)
<223> OTHER INFORMATION: Xaa is D-Ala

<400> SEQUENCE: 95

Ala Cys Pro Xaa Gly Pro Phe Trp Cys Pro Val Xaa Arg Pro Gly Cys
1               5                   10                  15

<210> SEQ ID NO 96
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (15)..(15)
<223> OTHER INFORMATION: Xaa is D-Ala

<400> SEQUENCE: 96

Ala Cys Pro Xaa Gly Pro Phe Trp Cys Pro Val Asn Arg Pro Xaa Cys
1               5                   10                  15

<210> SEQ ID NO 97
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (12)..(12)
<223> OTHER INFORMATION: Xaa is D-Ala

<400> SEQUENCE: 97

Ala Cys Pro Trp Gly Pro Phe Xaa Cys Pro Val Xaa Arg Pro Gly Cys
1               5                   10                  15

<210> SEQ ID NO 98
<211> LENGTH: 16
<212> TYPE: PRT
<213> ORGANISM: Artificial

```
<220> FEATURE:
<223> OTHER INFORMATION: Synthetic peptide
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (15)..(15)
<223> OTHER INFORMATION: Xaa is D-Ala

<400> SEQUENCE: 98

Ala Cys Pro Trp Gly Pro Phe Xaa Cys Pro Val Asn Arg Pro Xaa Cys
1               5                   10                  15

<210> SEQ ID NO 99
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (6)..(6)
<223> OTHER INFORMATION: Xaa is Aib

<400> SEQUENCE: 99

Ala Cys Pro Xaa Gly Xaa Phe Trp Cys Pro Val Asn Arg Pro Gly Cys
1               5                   10                  15

<210> SEQ ID NO 100
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (8)..(8)
<223> OTHER INFORMATION: Xaa is 1Nal

<400> SEQUENCE: 100

Ala Cys Pro Xaa Gly Pro Phe Xaa Cys Pro Val Asn Arg Pro Gly Cys
1               5                   10                  15

<210> SEQ ID NO 101
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (11)..(11)
<223> OTHER INFORMATION: Xaa is tBuGly

<400> SEQUENCE: 101

Ala Cys Pro Xaa Gly Pro Phe Trp Cys Pro Xaa Asn Arg Pro Gly Cys
1               5                   10                  15
```

```
<210> SEQ ID NO 102
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (13)..(13)
<223> OTHER INFORMATION: Xaa is HArg

<400> SEQUENCE: 102

Ala Cys Pro Xaa Gly Pro Phe Trp Cys Pro Val Asn Xaa Pro Gly Cys
1               5                   10                  15

<210> SEQ ID NO 103
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (8)..(8)
<223> OTHER INFORMATION: Xaa is 1Nal

<400> SEQUENCE: 103

Ala Cys Pro Trp Gly Xaa Phe Xaa Cys Pro Val Asn Arg Pro Gly Cys
1               5                   10                  15

<210> SEQ ID NO 104
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is Aib
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (12)..(12)
<223> OTHER INFORMATION: Xaa is D-Ala

<400> SEQUENCE: 104

Ala Cys Xaa Xaa Gly Pro Phe Trp Cys Pro Val Xaa Arg Pro Gly Cys
1               5                   10                  15

<210> SEQ ID NO 105
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is Aib
<220> FEATURE:
```

```
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (15)..(15)
<223> OTHER INFORMATION: Xaa is D-Ala

<400> SEQUENCE: 105

Ala Cys Xaa Xaa Gly Pro Phe Trp Cys Pro Val Asn Arg Pro Xaa Cys
1               5                   10                  15

<210> SEQ ID NO 106
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (11)..(11)
<223> OTHER INFORMATION: Xaa is tBuGly

<400> SEQUENCE: 106

Ala Cys Pro Xaa Gly Xaa Phe Trp Cys Pro Xaa Asn Arg Pro Gly Cys
1               5                   10                  15

<210> SEQ ID NO 107
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (12)..(12)
<223> OTHER INFORMATION: Xaa is D-Ala

<400> SEQUENCE: 107

Ala Cys Pro Xaa Gly Xaa Phe Trp Cys Pro Val Xaa Arg Pro Gly Cys
1               5                   10                  15

<210> SEQ ID NO 108
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (6)..(6)
<223> OTHER INFORMATION: Xaa is Aib
<220> FEATURE:
```

-continued

```
<221> NAME/KEY: Xaa
<222> LOCATION: (15)..(15)
<223> OTHER INFORMATION: Xaa is D-Ala

<400> SEQUENCE: 108

Ala Cys Pro Xaa Gly Xaa Phe Trp Cys Pro Val Asn Arg Pro Xaa Cys
1               5                   10                  15

<210> SEQ ID NO 109
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (11)..(11)
<223> OTHER INFORMATION: Xaa is tBuGly
<220> FEATURE:
<221> NAME/KEY: Xaa
<222> LOCATION: (12)..(12)
<223> OTHER INFORMATION: Xaa is D-Ala

<400> SEQUENCE: 109

Ala Cys Pro Xaa Gly Pro Phe Trp Cys Pro Xaa Xaa Arg Pro Gly Cys
1               5                   10                  15

<210> SEQ ID NO 110
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (11)..(11)
<223> OTHER INFORMATION: Xaa is tBuGly
<220> FEATURE:
<221> NAME/KEY: Xaa
<222> LOCATION: (13)..(13)
<223> OTHER INFORMATION: Xaa is HArg

<400> SEQUENCE: 110

Ala Cys Pro Xaa Gly Pro Phe Trp Cys Pro Xaa Asn Xaa Pro Gly Cys
1               5                   10                  15

<210> SEQ ID NO 111
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (11)..(11)
<223> OTHER INFORMATION: Xaa is tBuGly
<220> FEATURE:
<221> NAME/KEY: Xaa
<222> LOCATION: (14)..(14)
<223> OTHER INFORMATION: Xaa is Aib
```

```
<400> SEQUENCE: 111

Ala Cys Pro Xaa Gly Pro Phe Trp Cys Pro Xaa Asn Arg Xaa Gly Cys
1               5                   10                  15

<210> SEQ ID NO 112
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa ia 1Nal
<220> FEATURE:
<221> NAME/KEY: Xaa
<222> LOCATION: (11)..(11)
<223> OTHER INFORMATION: Xaa ia tBuGly
<220> FEATURE:
<221> NAME/KEY: Xaa
<222> LOCATION: (15)..(15)
<223> OTHER INFORMATION: Xaa ia D-Ala

<400> SEQUENCE: 112

Ala Cys Pro Xaa Gly Pro Phe Trp Cys Pro Xaa Asn Arg Pro Xaa Cys
1               5                   10                  15

<210> SEQ ID NO 113
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (12)..(12)
<223> OTHER INFORMATION: Xaa is D-Ala
<220> FEATURE:
<221> NAME/KEY: Xaa
<222> LOCATION: (13)..(13)
<223> OTHER INFORMATION: Xaa is HArg

<400> SEQUENCE: 113

Ala Cys Pro Xaa Gly Pro Phe Trp Cys Pro Val Xaa Xaa Pro Gly Cys
1               5                   10                  15

<210> SEQ ID NO 114
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (13)..(13)
<223> OTHER INFORMATION: Xaa is HArg
<220> FEATURE:
<221> NAME/KEY: Xaa
<222> LOCATION: (15)..(15)
<223> OTHER INFORMATION: Xaa is D-Ala

<400> SEQUENCE: 114

Ala Cys Pro Xaa Gly Pro Phe Trp Cys Pro Val Asn Xaa Pro Xaa Cys
1               5                   10                  15
```

```
<210> SEQ ID NO 115
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is Aib
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (14)..(14)
<223> OTHER INFORMATION: Xaa is Aib

<400> SEQUENCE: 115

Ala Cys Xaa Xaa Gly Xaa Phe Trp Cys Pro Val Asn Arg Xaa Gly Cys
1               5                   10                  15

<210> SEQ ID NO 116
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (11)..(11)
<223> OTHER INFORMATION: Xaa is tBuGly
<220> FEATURE:
<221> NAME/KEY: Xaa
<222> LOCATION: (13)..(13)
<223> OTHER INFORMATION: Xaa is HArg

<400> SEQUENCE: 116

Ala Cys Pro Xaa Gly Xaa Phe Trp Cys Pro Xaa Asn Xaa Pro Gly Cys
1               5                   10                  15

<210> SEQ ID NO 117
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (11)..(11)
<223> OTHER INFORMATION: Xaa is tBuGly
<220> FEATURE:
```

<221> NAME/KEY: Xaa
<222> LOCATION: (14)..(14)
<223> OTHER INFORMATION: Xaa is Aib

<400> SEQUENCE: 117

Ala Cys Pro Xaa Gly Xaa Phe Trp Cys Pro Xaa Asn Arg Xaa Gly Cys
1               5                   10                  15

<210> SEQ ID NO 118
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (11)..(11)
<223> OTHER INFORMATION: Xaa is tBuGly
<220> FEATURE:
<221> NAME/KEY: Xaa
<222> LOCATION: (13)..(13)
<223> OTHER INFORMATION: Xaa is HArg
<220> FEATURE:
<221> NAME/KEY: Xaa
<222> LOCATION: (14)..(14)
<223> OTHER INFORMATION: Xaa is Aib

<400> SEQUENCE: 118

Ala Cys Pro Xaa Gly Pro Phe Trp Cys Pro Xaa Asn Xaa Xaa Gly Cys
1               5                   10                  15

<210> SEQ ID NO 119
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp

<400> SEQUENCE: 119

His Xaa Val Pro Cys Pro Trp Gly Pro Phe Trp Cys Pro Val Asn Arg
1               5                   10                  15

Pro Gly Cys Ala
            20

<210> SEQ ID NO 120
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa

```
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 120

His Xaa Val Pro Cys Xaa Xaa Gly Xaa Phe Xaa Cys Pro Xaa Asn Xaa
1               5                   10                  15
Pro Xaa Cys

<210> SEQ ID NO 121
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib
<220> FEATURE:
<221> NAME/KEY: Xaa
<222> LOCATION: (18)..(18)
<223> OTHER INFORMATION: Xaa is D-Asp

<400> SEQUENCE: 121

His Xaa Val Pro Cys Xaa Xaa Gly Xaa Phe Xaa Cys Pro Xaa Asn Arg
1               5                   10                  15
Xaa Xaa Cys

<210> SEQ ID NO 122
<211> LENGTH: 20
<212> TYPE: PRT
<213> ORGANISM: Artificial
<220> FEATURE:
```

```
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: Xaa
<222> LOCATION: (9)..(9)
<223> OTHER INFORMATION: Xaa is Aib
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: Xaa
<222> LOCATION: (16)..(16)
<223> OTHER INFORMATION: Xaa is HArg
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: Xaa
<222> LOCATION: (18)..(18)
<223> OTHER INFORMATION: Xaa is D-Asp
<220> FEATURE:
<221> NAME/KEY: misc_feature
<222> LOCATION: (19)..(19)
<223> OTHER INFORMATION: Xaa can be any naturally occurring amino acid

<400> SEQUENCE: 122

His Xaa Val Pro Xaa Cys Pro Xaa Gly Xaa Phe Xaa Cys Pro Xaa Asn
1               5                   10                  15

Xaa Pro Xaa Cys
            20

<210> SEQ ID NO 123
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
```

-continued

<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 123

His Xaa Val Pro Cys Pro Xaa Gly Xaa Phe Xaa Cys Pro Xaa Asn Arg
1               5                   10                  15

Xaa Gly Cys

<210> SEQ ID NO 124
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib
<220> FEATURE:
<221> NAME/KEY: Xaa
<222> LOCATION: (18)..(18)
<223> OTHER INFORMATION: Xaa is D-Asp

<400> SEQUENCE: 124

His Xaa Val Pro Cys Pro Xaa Gly Xaa Phe Xaa Cys Pro Xaa Asn Arg
1               5                   10                  15

Xaa Xaa Cys

<210> SEQ ID NO 125
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)

```
<223> OTHER INFORMATION: Xaa is D-Asp
<220> FEATURE:
<221> NAME/KEY: Xaa
<222> LOCATION: (3)..(3)
<223> OTHER INFORMATION: Xaa is C5g
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib
<220> FEATURE:
<221> NAME/KEY: Xaa
<222> LOCATION: (18)..(18)
<223> OTHER INFORMATION: Xaa is D-Asp

<400> SEQUENCE: 125

His Xaa Xaa Pro Cys Xaa Xaa Gly Xaa Phe Xaa Cys Pro Xaa Asn Arg
1               5                   10                  15

Xaa Xaa Cys

<210> SEQ ID NO 126
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is C5g
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
```

<223> OTHER INFORMATION: Xaa is D-Asp

<400> SEQUENCE: 126

His Xaa Xaa Pro Cys Pro Xaa Gly Xaa Phe Xaa Cys Pro Xaa Asn Xaa
1               5                   10                  15

Pro Xaa Cys

<210> SEQ ID NO 127
<211> LENGTH: 19
<212> TYPE: PRT
<213> ORGANISM: Artificial
<220> FEATURE:
<223> OTHER INFORMATION: Synthetic peptide

<400> SEQUENCE: 127

Ala Asp Val His Cys Pro Trp Gly Pro Phe Trp Cys Pro Val Asn Arg
1               5                   10                  15

Pro Gly Cys

<210> SEQ ID NO 128
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is 3,3-DPA

<400> SEQUENCE: 128

Ala Asp Val His Cys Pro Xaa Gly Pro Phe Trp Cys Pro Val Asn Arg
1               5                   10                  15

Pro Gly Cys Ala
            20

<210> SEQ ID NO 129
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 1Nal

<400> SEQUENCE: 129

Ala Asp Val His Cys Pro Xaa Gly Pro Phe Trp Cys Pro Val Asn Arg
1               5                   10                  15

Pro Gly Cys Ala
            20

<210> SEQ ID NO 130
<211> LENGTH: 20
<212> TYPE: PRT
<213> ORGANISM: Artificial
<220> FEATURE:
<223> OTHER INFORMATION: Synthetic Peptide

<400> SEQUENCE: 130

Ala Asp Val His Cys Pro Trp Ala Pro Phe Trp Cys Pro Val Asn Arg
1               5                   10                  15

Pro Gly Cys Ala
            20

<210> SEQ ID NO 131
<211> LENGTH: 20
<212> TYPE: PRT
<213> ORGANISM: Artificial
<220> FEATURE:
<223> OTHER INFORMATION: Synthetic peptide

<400> SEQUENCE: 131

Ala Asp Val His Cys Pro Trp Gly Ala Phe Trp Cys Pro Val Asn Arg
1               5                   10                  15

Pro Gly Cys Ala
            20

<210> SEQ ID NO 132
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (9)..(9)
<223> OTHER INFORMATION: Xaa is Aib

<400> SEQUENCE: 132

Ala Asp Val His Cys Pro Trp Gly Xaa Phe Trp Cys Pro Val Asn Arg
1               5                   10                  15

Pro Gly Cys Ala
            20

<210> SEQ ID NO 133
<211> LENGTH: 21
<212> TYPE: PRT
<213> ORGANISM: Artificial
<220> FEATURE:
<223> OTHER INFORMATION: Synthetic peptide

<400> SEQUENCE: 133

Ala Asp Val His Cys Pro Trp Gly Pro Phe Trp Cys Ala Pro Val Asn
1               5                   10                  15

Arg Pro Gly Cys Ala
            20

<210> SEQ ID NO 134
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is D-Ala

<400> SEQUENCE: 134

Ala Asp Val His Cys Pro Trp Gly Pro Phe Trp Cys Pro Val Xaa Arg
1               5                   10                  15

Pro Gly Cys Ala
            20

<210> SEQ ID NO 135
<211> LENGTH: 20
<212> TYPE: PRT
<213> ORGANISM: Artificial
<220> FEATURE:

```
<223> OTHER INFORMATION: Synthetic peptide
<220> FEATURE:
<221> NAME/KEY: Xaa
<222> LOCATION: (16)..(16)
<223> OTHER INFORMATION: Xaa is D-Ala

<400> SEQUENCE: 135

Ala Asp Val His Cys Pro Trp Gly Pro Phe Trp Cys Pro Val Asn Xaa
1               5                   10                  15

Pro Gly Cys Ala
            20

<210> SEQ ID NO 136
<211> LENGTH: 19
<212> TYPE: PRT
<213> ORGANISM: Artificial
<220> FEATURE:
<223> OTHER INFORMATION: Synthetic peptide

<400> SEQUENCE: 136

Ala Asp Val Thr Cys Pro Trp Gly Pro Phe Trp Cys Pro Val Asn Arg
1               5                   10                  15

Pro Gly Cys

<210> SEQ ID NO 137
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp

<400> SEQUENCE: 137

Ala Xaa Val Thr Cys Pro Trp Gly Pro Phe Trp Cys Pro Val Asn Arg
1               5                   10                  15

Pro Gly Cys

<210> SEQ ID NO 138
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is D-Asp

<400> SEQUENCE: 138

Ala Xaa Xaa Thr Cys Pro Trp Gly Pro Phe Trp Cys Pro Val Asn Arg
1               5                   10                  15

Pro Gly Cys

<210> SEQ ID NO 139
<211> LENGTH: 19
<212> TYPE: PRT
<213> ORGANISM: Artificial
<220> FEATURE:
<223> OTHER INFORMATION: Synthetic peptide
<220> FEATURE:
```

```
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is Cba

<400> SEQUENCE: 139

Ala Xaa Xaa Thr Cys Pro Trp Gly Pro Phe Trp Cys Pro Val Asn Arg
1               5                   10                  15

Pro Gly Cys

<210> SEQ ID NO 140
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is Cpa

<400> SEQUENCE: 140

Ala Xaa Xaa Thr Cys Pro Trp Gly Pro Phe Trp Cys Pro Val Asn Arg
1               5                   10                  15

Pro Gly Cys

<210> SEQ ID NO 141
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is Cpg

<400> SEQUENCE: 141

Ala Xaa Xaa Thr Cys Pro Trp Gly Pro Phe Trp Cys Pro Val Asn Arg
1               5                   10                  15

Pro Gly Cys

<210> SEQ ID NO 142
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is C5g

<400> SEQUENCE: 142
```

Ala Xaa Xaa Val Thr Cys Pro Trp Gly Pro Phe Trp Cys Pro Val Asn
1               5                   10                  15

Arg Pro Gly Cys
            20

<210> SEQ ID NO 143
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is tBuGly

<400> SEQUENCE: 143

Ala Asp Xaa Thr Cys Pro Trp Gly Pro Phe Trp Cys Pro Val Asn Arg
1               5                   10                  15

Pro Gly Cys

<210> SEQ ID NO 144
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is AC3C

<400> SEQUENCE: 144

Ala Xaa Val Thr Cys Xaa Trp Gly Pro Phe Trp Cys Pro Val Asn Arg
1               5                   10                  15

Pro Gly Cys

<210> SEQ ID NO 145
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is AC4C

<400> SEQUENCE: 145

Ala Xaa Val Thr Cys Xaa Trp Gly Pro Phe Trp Cys Pro Val Asn Arg
1               5                   10                  15

Pro Gly Cys

<210> SEQ ID NO 146
<211> LENGTH: 19
<212> TYPE: PRT
<213> ORGANISM: Artificial
<220> FEATURE:
<223> OTHER INFORMATION: Synthetic peptide
<220> FEATURE:

```
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is AC5C

<400> SEQUENCE: 146

Ala Xaa Val Thr Cys Xaa Trp Gly Pro Phe Trp Cys Pro Val Asn Arg
1               5                   10                  15

Pro Gly Cys

<210> SEQ ID NO 147
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is 4BenzylPro

<400> SEQUENCE: 147

Ala Xaa Val Thr Cys Xaa Trp Gly Pro Phe Trp Cys Pro Val Asn Arg
1               5                   10                  15

Pro Gly Cys

<210> SEQ ID NO 148
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is 4PhenylPro

<400> SEQUENCE: 148

Ala Xaa Val Thr Cys Xaa Trp Gly Pro Phe Trp Cys Pro Val Asn Arg
1               5                   10                  15

Pro Gly Cys

<210> SEQ ID NO 149
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal

<400> SEQUENCE: 149
```

```
Ala Xaa Val Thr Cys Pro Xaa Gly Pro Phe Trp Cys Pro Val Asn Arg
1               5                   10                  15

Pro Gly Cys

<210> SEQ ID NO 150
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (10)..(10)
<223> OTHER INFORMATION: Xaa is HArg

<400> SEQUENCE: 150

Ala Xaa Val Thr Cys Pro Trp Gly Pro Xaa Trp Cys Pro Val Asn Arg
1               5                   10                  15

Pro Gly Cys

<210> SEQ ID NO 151
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp

<400> SEQUENCE: 151

Ala Xaa Val Thr Cys Pro Trp Gly Pro Asn Trp Cys Pro Val Asn Arg
1               5                   10                  15

Pro Gly Cys

<210> SEQ ID NO 152
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp

<400> SEQUENCE: 152

Ala Xaa Val Thr Cys Pro Trp Gly Pro Ala Trp Cys Pro Val Asn Arg
1               5                   10                  15

Pro Gly Cys

<210> SEQ ID NO 153
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp

<400> SEQUENCE: 153
```

```
Ala Xaa Val Thr Cys Pro Trp Gly Pro Phe Trp Cys Pro Leu Asn Arg
1               5                   10                  15

Pro Gly Cys
```

<210> SEQ ID NO 154
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (18)..(18)
<223> OTHER INFORMATION: Xaa is D-Asp

<400> SEQUENCE: 154

```
Ala Xaa Val Thr Cys Pro Trp Gly Pro Phe Trp Cys Pro Val Asn Arg
1               5                   10                  15

Pro Xaa Cys
```

<210> SEQ ID NO 155
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 155

```
Ala Xaa Val Thr Cys Pro Trp Gly Pro Phe Trp Cys Pro Val Asn Xaa
1               5                   10                  15

Pro Xaa Cys
```

<210> SEQ ID NO 156
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (16)..(16)
<223> OTHER INFORMATION: Xaa is Aib
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: Xaa
<222> LOCATION: (18)..(18)
<223> OTHER INFORMATION: Xaa is D-Asp

```
<400> SEQUENCE: 156

Ala Xaa Val Thr Cys Pro Trp Gly Pro Phe Trp Cys Pro Val Asn Arg
1               5                   10                  15

Xaa Xaa Cys

<210> SEQ ID NO 157
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (17)..(17)
<223> OTHER INFORMATION: Xaa is Aib

<400> SEQUENCE: 157

Ala Xaa Val Thr Cys Pro Xaa Gly Xaa Phe Trp Cys Pro Val Asn Arg
1               5                   10                  15

Xaa Gly Cys

<210> SEQ ID NO 158
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (17)..(17)
<223> OTHER INFORMATION: Xaa is Aib

<400> SEQUENCE: 158

Ala Xaa Val Thr Cys Pro Trp Gly Xaa Phe Xaa Cys Pro Val Asn Arg
1               5                   10                  15

Xaa Gly Cys

<210> SEQ ID NO 159
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
```

```
<222> LOCATION: (2)..(2)
<223> OTHER INFORMATION: Xaa is D-Asp
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 159

Ala Xaa Val Thr Cys Pro Trp Gly Xaa Phe Trp Cys Pro Xaa Asn Arg
1               5                   10                  15

Xaa Gly Cys

<210> SEQ ID NO 160
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (17)..(17)
<223> OTHER INFORMATION: Xaa is Aib

<400> SEQUENCE: 160

Ala Xaa Val Thr Cys Pro Xaa Gly Xaa Phe Xaa Cys Pro Val Asn Arg
1               5                   10                  15

Xaa Gly Cys

<210> SEQ ID NO 161
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
```

```
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg

<400> SEQUENCE: 161

Ala Xaa Val Thr Cys Pro Xaa Gly Xaa Phe Xaa Cys Pro Xaa Asn Xaa
1               5                   10                  15

Pro Gly Cys

<210> SEQ ID NO 162
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 162

Ala Xaa Val Thr Cys Pro Xaa Gly Xaa Phe Xaa Cys Pro Xaa Asn Arg
1               5                   10                  15

Xaa Gly Cys

<210> SEQ ID NO 163
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
```

```
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 163

Ala Xaa Val Thr Cys Pro Xaa Gly Xaa Phe Xaa Cys Pro Xaa Asn Xaa
1               5                   10                  15

Pro Xaa Cys

<210> SEQ ID NO 164
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: Xaa is D-Asp

<400> SEQUENCE: 164

Xaa Val Thr Cys Pro Trp Gly Pro Phe Trp Cys Pro Val Asn Arg Pro
1               5                   10                  15

Gly Cys

<210> SEQ ID NO 165
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: Xaa is D-Asp
<220> FEATURE:
<221> NAME/KEY: Xaa
<222> LOCATION: (6)..(6)
<223> OTHER INFORMATION: Xaa is 1Nal
<220> FEATURE:
<221> NAME/KEY: Xaa
<222> LOCATION: (8)..(8)
<223> OTHER INFORMATION: Xaa is Aib
<220> FEATURE:
<221> NAME/KEY: Xaa
<222> LOCATION: (10)..(10)
<223> OTHER INFORMATION: Xaa is 1Nal
<220> FEATURE:
<221> NAME/KEY: Xaa
<222> LOCATION: (13)..(13)
<223> OTHER INFORMATION: Xaa is tBuGly
<220> FEATURE:
<221> NAME/KEY: Xaa
<222> LOCATION: (16)..(16)
<223> OTHER INFORMATION: Xaa is Aib

<400> SEQUENCE: 165

Xaa Val Thr Cys Pro Xaa Gly Xaa Phe Xaa Cys Pro Xaa Asn Arg Xaa
1               5                   10                  15

Gly Cys
```

```
<210> SEQ ID NO 166
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (8)..(8)
<223> OTHER INFORMATION: Xaa is 1Nal

<400> SEQUENCE: 166

Ala His Asp Val Pro Cys Pro Xaa Gly Pro Phe Trp Cys Pro Val Asn
1               5                   10                  15

Arg Pro Gly Cys Ala
            20

<210> SEQ ID NO 167
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (8)..(8)
<223> OTHER INFORMATION: Xaa is 1Nal

<400> SEQUENCE: 167

Ala His Asp Val Pro Cys Pro Xaa Gly Pro Phe Trp Cys Pro Val Asn
1               5                   10                  15

Arg Pro Gly Cys
            20

<210> SEQ ID NO 168
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (12)..(12)
<223> OTHER INFORMATION: Xaa is 1Nal

<400> SEQUENCE: 168

Ala His Asp Val Pro Cys Pro Trp Gly Pro Phe Xaa Cys Pro Val Asn
1               5                   10                  15

Arg Pro Gly Cys
            20

<210> SEQ ID NO 169
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (15)..(15)
<223> OTHER INFORMATION: Xaa is tBuGly

<400> SEQUENCE: 169

Ala His Asp Val Pro Cys Pro Xaa Gly Pro Phe Trp Cys Pro Xaa Asn
1               5                   10                  15
```

Arg Pro Gly Cys
            20

<210> SEQ ID NO 170
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (10)..(10)
<223> OTHER INFORMATION: Xaa is Aib
<220> FEATURE:
<221> NAME/KEY: Xaa
<222> LOCATION: (15)..(15)
<223> OTHER INFORMATION: Xaa is tBuGly
<220> FEATURE:
<221> NAME/KEY: Xaa
<222> LOCATION: (17)..(17)
<223> OTHER INFORMATION: Xaa is HArg

<400> SEQUENCE: 170

Ala His Asp Val Pro Cys Pro Xaa Gly Xaa Phe Trp Cys Pro Xaa Asn
1               5                   10                  15

Xaa Pro Gly Cys
            20

<210> SEQ ID NO 171
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (10)..(10)
<223> OTHER INFORMATION: Xaa is Aib
<220> FEATURE:
<221> NAME/KEY: Xaa
<222> LOCATION: (15)..(15)
<223> OTHER INFORMATION: Xaa is tBuGly
<220> FEATURE:
<221> NAME/KEY: Xaa
<222> LOCATION: (18)..(18)
<223> OTHER INFORMATION: Xaa is Aib

<400> SEQUENCE: 171

Ala His Asp Val Pro Cys Pro Xaa Gly Xaa Phe Trp Cys Pro Xaa Asn
1               5                   10                  15

Arg Xaa Gly Cys
            20

<210> SEQ ID NO 172
<211> LENGTH: 20
<212> TYPE: PRT
<213> ORGANISM: Artificial
<220> FEATURE:
<223> OTHER INFORMATION: Synthetic peptide

<400> SEQUENCE: 172

Ala His Asp Val Pro Cys Pro Trp Gly Pro Phe Trp Cys Pro Val Asn

```
1               5                   10                  15

Arg Pro Gly Cys
            20

<210> SEQ ID NO 173
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: Xaa is D-Ala

<400> SEQUENCE: 173

Xaa His Asp Val Pro Cys Pro Trp Gly Pro Phe Trp Cys Pro Val Asn
1               5                   10                  15

Arg Pro Gly Cys
            20

<210> SEQ ID NO 174
<211> LENGTH: 20
<212> TYPE: PRT
<213> ORGANISM: Artificial
<220> FEATURE:
<223> OTHER INFORMATION: Synthetic peptide

<400> SEQUENCE: 174

Ala Ala Asp Val Pro Cys Pro Trp Gly Pro Phe Trp Cys Pro Val Asn
1               5                   10                  15

Arg Pro Gly Cys
            20

<210> SEQ ID NO 175
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-His

<400> SEQUENCE: 175

Ala Xaa Asp Val Pro Cys Pro Trp Gly Pro Phe Trp Cys Pro Val Asn
1               5                   10                  15

Arg Pro Gly Cys
            20

<210> SEQ ID NO 176
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-His

<400> SEQUENCE: 176

Ala Xaa Asp Val Cys Pro Trp Gly Pro Phe Trp Cys Pro Val Asn Arg
1               5                   10                  15

Pro Gly Cys
```

```
<210> SEQ ID NO 177
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Ala

<400> SEQUENCE: 177

Ala Xaa Asp Val Pro Cys Pro Trp Gly Pro Phe Trp Cys Pro Val Asn
1               5                   10                  15

Arg Pro Gly Cys
            20

<210> SEQ ID NO 178
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp

<400> SEQUENCE: 178

Ala Xaa Asp Val Pro Cys Pro Trp Gly Pro Phe Trp Cys Pro Val Asn
1               5                   10                  15

Arg Pro Gly Cys
            20

<210> SEQ ID NO 179
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is Thi

<400> SEQUENCE: 179

Ala Xaa Asp Val Pro Cys Pro Trp Gly Pro Phe Trp Cys Pro Val Asn
1               5                   10                  15

Arg Pro Gly Cys
            20

<210> SEQ ID NO 180
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is ThiAz

<400> SEQUENCE: 180

Ala Xaa Asp Val Pro Cys Pro Trp Gly Pro Phe Trp Cys Pro Val Asn
1               5                   10                  15

Arg Pro Gly Cys
```

```
            20

<210> SEQ ID NO 181
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is 2FuAla

<400> SEQUENCE: 181

Ala Xaa Asp Val Pro Cys Pro Trp Gly Pro Phe Trp Cys Pro Val Asn
1               5                   10                  15

Arg Pro Gly Cys
            20

<210> SEQ ID NO 182
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-His
<220> FEATURE:
<221> NAME/KEY: Xaa
<222> LOCATION: (4)..(4)
<223> OTHER INFORMATION: Xaa is tBuGly

<400> SEQUENCE: 182

Ala Xaa Asp Xaa Pro Cys Pro Trp Gly Pro Phe Trp Cys Pro Val Asn
1               5                   10                  15

Arg Pro Gly Cys
            20

<210> SEQ ID NO 183
<211> LENGTH: 20
<212> TYPE: PRT
<213> ORGANISM: Artificial
<220> FEATURE:
<223> OTHER INFORMATION: Synthetic peptide

<400> SEQUENCE: 183

Ala His Ala Val Pro Cys Pro Trp Gly Pro Phe Trp Cys Pro Val Asn
1               5                   10                  15

Arg Pro Gly Cys
            20

<210> SEQ ID NO 184
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is D-Ala

<400> SEQUENCE: 184

Ala His Xaa Val Pro Cys Pro Trp Gly Pro Phe Trp Cys Pro Val Asn
1               5                   10                  15
```

Arg Pro Gly Cys
            20

<210> SEQ ID NO 185
<211> LENGTH: 20
<212> TYPE: PRT
<213> ORGANISM: Artificial
<220> FEATURE:
<223> OTHER INFORMATION: Synthetic peptide

<400> SEQUENCE: 185

Ala His Glu Val Pro Cys Pro Trp Gly Pro Phe Trp Cys Pro Val Asn
1               5                   10                  15

Arg Pro Gly Cys
            20

<210> SEQ ID NO 186
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is D-Glu

<400> SEQUENCE: 186

Ala His Xaa Val Pro Cys Pro Trp Gly Pro Phe Trp Cys Pro Val Asn
1               5                   10                  15

Arg Pro Gly Cys
            20

<210> SEQ ID NO 187
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is D-Asp

<400> SEQUENCE: 187

Ala His Xaa Val Pro Cys Pro Trp Gly Pro Phe Trp Cys Pro Val Asn
1               5                   10                  15

Arg Pro Gly Cys
            20

<210> SEQ ID NO 188
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is D-Asp
<220> FEATURE:
<221> NAME/KEY: Xaa
<222> LOCATION: (4)..(4)
<223> OTHER INFORMATION: Xaa is tBuGly

<400> SEQUENCE: 188

Ala His Xaa Xaa Pro Cys Pro Trp Gly Pro Phe Trp Cys Pro Val Asn
1               5                   10                  15

Arg Pro Gly Cys
            20

<210> SEQ ID NO 189
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is D-Asp
<220> FEATURE:
<221> NAME/KEY: Xaa
<222> LOCATION: (5)..(5)
<223> OTHER INFORMATION: Xaa is Sar

<400> SEQUENCE: 189

Ala His Xaa Val Xaa Cys Pro Trp Gly Pro Phe Trp Cys Pro Val Asn
1               5                   10                  15

Arg Pro Gly Cys
            20

<210> SEQ ID NO 190
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is D-Asp
<220> FEATURE:
<221> NAME/KEY: Xaa
<222> LOCATION: (5)..(5)
<223> OTHER INFORMATION: Xaa is Aib

<400> SEQUENCE: 190

Ala His Xaa Val Xaa Cys Pro Trp Gly Pro Phe Trp Cys Pro Val Asn
1               5                   10                  15

Arg Pro Gly Cys
            20

<210> SEQ ID NO 191
<211> LENGTH: 20
<212> TYPE: PRT
<213> ORGANISM: Artificial
<220> FEATURE:
<223> OTHER INFORMATION: Synthetic peptide

<400> SEQUENCE: 191

Ala His Asp Ala Pro Cys Pro Trp Gly Pro Phe Trp Cys Pro Val Asn
1               5                   10                  15

Arg Pro Gly Cys
            20

<210> SEQ ID NO 192
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is D-Ala

```
<400> SEQUENCE: 192

Ala His Asp Xaa Pro Cys Pro Trp Gly Pro Phe Trp Cys Pro Val Asn
1               5                   10                  15

Arg Pro Gly Cys
            20

<210> SEQ ID NO 193
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is Aib

<400> SEQUENCE: 193

Ala His Asp Xaa Pro Cys Pro Trp Gly Pro Phe Trp Cys Pro Val Asn
1               5                   10                  15

Arg Pro Gly Cys
            20

<210> SEQ ID NO 194
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is tBuGly

<400> SEQUENCE: 194

Ala His Asp Xaa Pro Cys Pro Trp Gly Pro Phe Trp Cys Pro Val Asn
1               5                   10                  15

Arg Pro Gly Cys
            20

<210> SEQ ID NO 195
<211> LENGTH: 20
<212> TYPE: PRT
<213> ORGANISM: Artificial
<220> FEATURE:
<223> OTHER INFORMATION: Synthetic peptide

<400> SEQUENCE: 195

Ala His Asp Val Ala Cys Pro Trp Gly Pro Phe Trp Cys Pro Val Asn
1               5                   10                  15

Arg Pro Gly Cys
            20

<210> SEQ ID NO 196
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is D-Ala

<400> SEQUENCE: 196
```

```
Ala His Asp Val Xaa Cys Pro Trp Gly Pro Phe Trp Cys Pro Val Asn
1               5                   10                  15

Arg Pro Gly Cys
            20

<210> SEQ ID NO 197
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is Aib

<400> SEQUENCE: 197

Ala His Asp Val Xaa Cys Pro Trp Gly Pro Phe Trp Cys Pro Val Asn
1               5                   10                  15

Arg Pro Gly Cys
            20

<210> SEQ ID NO 198
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is Aze

<400> SEQUENCE: 198

Ala His Asp Val Xaa Cys Pro Trp Gly Pro Phe Trp Cys Pro Val Asn
1               5                   10                  15

Arg Pro Gly Cys
            20

<210> SEQ ID NO 199
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is Pip

<400> SEQUENCE: 199

Ala His Asp Val Xaa Cys Pro Trp Gly Pro Phe Trp Cys Pro Val Asn
1               5                   10                  15

Arg Pro Gly Cys
            20

<210> SEQ ID NO 200
<211> LENGTH: 19
<212> TYPE: PRT
<213> ORGANISM: Artificial
<220> FEATURE:
<223> OTHER INFORMATION: Synthetic peptide

<400> SEQUENCE: 200

His Asp Val Pro Cys Pro Trp Gly Pro Phe Trp Cys Pro Val Asn Arg
1               5                   10                  15
```

Pro Gly Cys

```
<210> SEQ ID NO 201
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: Xaa is D-His

<400> SEQUENCE: 201

Xaa Asp Val Pro Cys Pro Trp Gly Pro Phe Trp Cys Pro Val Asn Arg
1               5                   10                  15

Pro Gly Cys

<210> SEQ ID NO 202
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp

<400> SEQUENCE: 202

His Xaa Val Pro Cys Pro Trp Gly Pro Phe Trp Cys Pro Val Asn Arg
1               5                   10                  15

Pro Gly Cys

<210> SEQ ID NO 203
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is D-Asp
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (15)..(15)
<223> OTHER INFORMATION: Xaa is tBuGly
<220> FEATURE:
<221> NAME/KEY: Xaa
<222> LOCATION: (17)..(17)
<223> OTHER INFORMATION: Xaa is HArg

<400> SEQUENCE: 203

Ala His Xaa Val Pro Cys Pro Xaa Gly Pro Phe Trp Cys Pro Xaa Asn
1               5                   10                  15

Xaa Pro Gly Cys
            20

<210> SEQ ID NO 204
<211> LENGTH: 20
<212> TYPE: PRT
<213> ORGANISM: Artificial
<220> FEATURE:
<223> OTHER INFORMATION: Synthetic peptide
```

```
<220> FEATURE:
<221> NAME/KEY: Xaa
<222> LOCATION: (2)..(2)
<223> OTHER INFORMATION: Xaa is D-His
<220> FEATURE:
<221> NAME/KEY: Xaa
<222> LOCATION: (11)..(11)
<223> OTHER INFORMATION: Xaa is Psi-Ala

<400> SEQUENCE: 204

Ala Xaa Asp Val Pro Cys Pro Trp Gly Pro Xaa Trp Cys Pro Val Asn
1               5                   10                  15

Arg Pro Gly Cys
            20

<210> SEQ ID NO 205
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-His
<220> FEATURE:
<221> NAME/KEY: Xaa
<222> LOCATION: (15)..(15)
<223> OTHER INFORMATION: Xaa is HArg

<400> SEQUENCE: 205

Ala Xaa Asp Val Pro Cys Pro Trp Gly Pro Phe Trp Cys Pro Xaa Asn
1               5                   10                  15

Arg Pro Gly Cys
            20

<210> SEQ ID NO 206
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-His
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (15)..(15)
<223> OTHER INFORMATION: Xaa is tBuGly
<220> FEATURE:
<221> NAME/KEY: Xaa
<222> LOCATION: (17)..(17)
<223> OTHER INFORMATION: Xaa is HArg

<400> SEQUENCE: 206

Ala Xaa Asp Val Pro Cys Pro Xaa Gly Pro Phe Trp Cys Pro Xaa Asn
1               5                   10                  15

Xaa Pro Gly Cys
            20

<210> SEQ ID NO 207
<211> LENGTH: 20
<212> TYPE: PRT
<213> ORGANISM: Artificial
<220> FEATURE:
```

```
<223> OTHER INFORMATION: Synthetic peptide
<220> FEATURE:
<221> NAME/KEY: Xaa
<222> LOCATION: (2)..(2)
<223> OTHER INFORMATION: Xaa is D-His
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (10)..(10)
<223> OTHER INFORMATION: Xaa is Aib
<220> FEATURE:
<221> NAME/KEY: Xaa
<222> LOCATION: (12)..(12)
<223> OTHER INFORMATION: Xaa is 1Nal
<220> FEATURE:
<221> NAME/KEY: Xaa
<222> LOCATION: (15)..(15)
<223> OTHER INFORMATION: Xaa is tBuGly
<220> FEATURE:
<221> NAME/KEY: Xaa
<222> LOCATION: (17)..(17)
<223> OTHER INFORMATION: Xaa is HArg

<400> SEQUENCE: 207

Ala Xaa Asp Val Pro Cys Pro Xaa Gly Xaa Phe Xaa Cys Pro Xaa Asn
1               5                   10                  15

Xaa Pro Gly Cys
            20

<210> SEQ ID NO 208
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-His
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (10)..(10)
<223> OTHER INFORMATION: Xaa is Aib
<220> FEATURE:
<221> NAME/KEY: Xaa
<222> LOCATION: (12)..(12)
<223> OTHER INFORMATION: Xaa is 1Nal
<220> FEATURE:
<221> NAME/KEY: Xaa
<222> LOCATION: (15)..(15)
<223> OTHER INFORMATION: Xaa is tBuGly
<220> FEATURE:
<221> NAME/KEY: Xaa
<222> LOCATION: (18)..(18)
<223> OTHER INFORMATION: Xaa is Aib

<400> SEQUENCE: 208

Ala Xaa Asp Val Pro Cys Pro Xaa Gly Xaa Phe Xaa Cys Pro Xaa Asn
1               5                   10                  15

Arg Xaa Gly Cys
            20

<210> SEQ ID NO 209
<211> LENGTH: 20
<212> TYPE: PRT
<213> ORGANISM: Artificial
```

```
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-His
<220> FEATURE:
<221> NAME/KEY: Xaa
<222> LOCATION: (10)..(10)
<223> OTHER INFORMATION: Xaa is Aib
<220> FEATURE:
<221> NAME/KEY: Xaa
<222> LOCATION: (15)..(15)
<223> OTHER INFORMATION: Xaa is tBuGly
<220> FEATURE:
<221> NAME/KEY: Xaa
<222> LOCATION: (18)..(18)
<223> OTHER INFORMATION: Xaa is Aib

<400> SEQUENCE: 209

Ala Xaa Asp Val Pro Cys Pro Trp Gly Xaa Phe Trp Cys Pro Xaa Asn
1               5                   10                  15

Arg Xaa Gly Cys
            20

<210> SEQ ID NO 210
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly

<400> SEQUENCE: 210

His Xaa Val Pro Cys Xaa Xaa Gly Xaa Phe Xaa Cys Pro Xaa Asn Arg
1               5                   10                  15

Pro Gly Cys

<210> SEQ ID NO 211
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
```

```
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg

<400> SEQUENCE: 211

His Xaa Val Pro Cys Xaa Xaa Gly Xaa Phe Xaa Cys Pro Xaa Asn Xaa
1               5                   10                  15

Pro Gly Cys

<210> SEQ ID NO 212
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (17)..(17)
<223> OTHER INFORMATION: Xaa is Aib
<220> FEATURE:
<221> NAME/KEY: Xaa
<222> LOCATION: (18)..(18)
<223> OTHER INFORMATION: Xaa is D-Asp

<400> SEQUENCE: 212

His Xaa Val Pro Cys Xaa Xaa Gly Xaa Phe Xaa Cys Pro Xaa Asn Xaa
1               5                   10                  15
```

-continued

Xaa Xaa Cys

<210> SEQ ID NO 213
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 213

His Xaa Val Pro Cys Xaa Xaa Gly Xaa Phe Xaa Cys Pro Xaa Asn Arg
1               5                   10                  15

Xaa Gly Cys

<210> SEQ ID NO 214
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)

<223> OTHER INFORMATION: Xaa is D-Asp

<400> SEQUENCE: 214

His Xaa Val Pro Cys Xaa Xaa Gly Xaa Phe Trp Cys Pro Xaa Asn Xaa
1               5                   10                  15

Pro Xaa Cys

<210> SEQ ID NO 215
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (10)..(10)
<223> OTHER INFORMATION: Xaa is HArg
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 215

His Xaa Val Pro Cys Xaa Xaa Gly Pro Xaa Xaa Cys Pro Xaa Asn Arg
1               5                   10                  15

Xaa Gly Cys

<210> SEQ ID NO 216
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (10)..(10)
<223> OTHER INFORMATION: Xaa is HArg
<220> FEATURE:
<221> NAME/KEY: Xaa
<222> LOCATION: (11)..(11)
<223> OTHER INFORMATION: Xaa is 1Nal -continued

```
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 216

His Xaa Val Pro Cys Xaa Xaa Gly Pro Xaa Xaa Cys Pro Xaa Asn Xaa
1               5                   10                  15

Pro Xaa Cys

<210> SEQ ID NO 217
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (10)..(10)
<223> OTHER INFORMATION: Xaa is HArg
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 217

His Xaa Val Pro Cys Xaa Trp Gly Pro Xaa Xaa Cys Pro Xaa Asn Xaa
1               5                   10                  15

Pro Xaa Cys

<210> SEQ ID NO 218
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
```

```
<221> NAME/KEY: Xaa
<222> LOCATION: (10)..(10)
<223> OTHER INFORMATION: Xaa is HArg
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 218

His Xaa Val Pro Cys Xaa Trp Gly Pro Xaa Trp Cys Pro Xaa Asn Xaa
1               5                   10                  15

Pro Xaa Cys

<210> SEQ ID NO 219
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is D-Ala
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 219

His Xaa Val Pro Cys Xaa Xaa Gly Xaa Phe Xaa Cys Pro Xaa Asn Xaa
1               5                   10                  15

Pro Xaa Cys

<210> SEQ ID NO 220
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
```

```
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (10)..(10)
<223> OTHER INFORMATION: Xaa is HArg
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 220

His Xaa Val Pro Cys Pro Xaa Gly Xaa Xaa Xaa Cys Pro Xaa Asn Arg
1               5                   10                  15

Xaa Gly Cys

<210> SEQ ID NO 221
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (10)..(10)
<223> OTHER INFORMATION: Xaa is HArg
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib
<220> FEATURE:
<221> NAME/KEY: Xaa
<222> LOCATION: (18)..(18)
<223> OTHER INFORMATION: Xaa is D-Asp

<400> SEQUENCE: 221

His Xaa Val Pro Cys Pro Xaa Gly Xaa Xaa Xaa Cys Pro Xaa Asn Arg
1               5                   10                  15
```

Xaa Xaa Cys

<210> SEQ ID NO 222
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (10)..(10)
<223> OTHER INFORMATION: Xaa is HArg
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 222

His Xaa Val Pro Cys Pro Xaa Gly Xaa Xaa Xaa Cys Pro Xaa Asn Xaa
1               5                   10                  15

Pro Xaa Cys

<210> SEQ ID NO 223
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly

<400> SEQUENCE: 223

```
His Xaa Val Pro Cys Pro Xaa Gly Xaa Phe Xaa Cys Pro Xaa Asn Arg
1               5                   10                  15

Pro Gly Cys

<210> SEQ ID NO 224
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg

<400> SEQUENCE: 224

His Xaa Val Pro Cys Pro Xaa Gly Xaa Phe Xaa Cys Pro Xaa Asn Xaa
1               5                   10                  15

Pro Gly Cys

<210> SEQ ID NO 225
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (17)..(17)
<223> OTHER INFORMATION: Xaa is Aib
```

```
<220> FEATURE:
<221> NAME/KEY: Xaa
<222> LOCATION: (18)..(18)
<223> OTHER INFORMATION: Xaa is D-Asp

<400> SEQUENCE: 225

His Xaa Val Pro Cys Pro Xaa Gly Xaa Phe Xaa Cys Pro Xaa Asn Xaa
1               5                   10                  15

Xaa Xaa Cys

<210> SEQ ID NO 226
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (17)..(17)
<223> OTHER INFORMATION: Xaa is Aib

<400> SEQUENCE: 226

His Xaa Val Pro Cys Pro Xaa Gly Xaa Phe Xaa Cys Pro Val Asn Arg
1               5                   10                  15

Xaa Gly Cys

<210> SEQ ID NO 227
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp
```

<400> SEQUENCE: 227

His Xaa Val Pro Cys Pro Xaa Gly Xaa Phe Trp Cys Pro Xaa Asn Xaa
1               5                   10                  15

Pro Xaa Cys

<210> SEQ ID NO 228
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (17)..(17)
<223> OTHER INFORMATION: Xaa is Aib

<400> SEQUENCE: 228

His Xaa Val Pro Cys Pro Xaa Gly Xaa Phe Trp Cys Pro Val Asn Arg
1               5                   10                  15

Xaa Gly Cys

<210> SEQ ID NO 229
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (8)..(8)
<223> OTHER INFORMATION: Xaa is Aza-Gly

<400> SEQUENCE: 229

His Xaa Val Pro Cys Pro Trp Xaa Pro Phe Trp Cys Pro Val Asn Arg
1               5                   10                  15

Pro Gly Cys

<210> SEQ ID NO 230
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)

```
<223> OTHER INFORMATION: Xaa is 1Nal
<220> FEATURE:
<221> NAME/KEY: Xaa
<222> LOCATION: (17)..(17)
<223> OTHER INFORMATION: Xaa is Aib

<400> SEQUENCE: 230

His Xaa Val Pro Cys Pro Trp Gly Xaa Phe Xaa Cys Pro Val Asn Arg
1               5                   10                  15

Xaa Gly Cys

<210> SEQ ID NO 231
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 231

His Xaa Val Pro Cys Pro Trp Gly Xaa Phe Xaa Cys Pro Xaa Asn Xaa
1               5                   10                  15

Pro Xaa Cys

<210> SEQ ID NO 232
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 232

His Xaa Val Pro Cys Pro Trp Gly Xaa Phe Trp Cys Pro Xaa Asn Arg
```

1               5                   10                  15

Xaa Gly Cys

<210> SEQ ID NO 233
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 233

His Xaa Val Pro Cys Pro Trp Gly Xaa Phe Trp Cys Pro Xaa Asn Xaa
1               5                   10                  15

Pro Xaa Cys

<210> SEQ ID NO 234
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (10)..(10)
<223> OTHER INFORMATION: Xaa is HArg
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 234

His Xaa Val Pro Cys Pro Trp Gly Pro Xaa Trp Cys Pro Xaa Asn Xaa
1               5                   10                  15

Pro Xaa Cys

<210> SEQ ID NO 235
<211> LENGTH: 19
<212> TYPE: PRT
<213> ORGANISM: Artificial

```
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is C5g
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib
<220> FEATURE:
<221> NAME/KEY: Xaa
<222> LOCATION: (18)..(18)
<223> OTHER INFORMATION: Xaa is D-Asp

<400> SEQUENCE: 235

His Xaa Xaa Pro Cys Xaa Trp Gly Xaa Phe Trp Cys Pro Xaa Asn Arg
 1               5                  10                  15

Xaa Xaa Cys

<210> SEQ ID NO 236
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is C5g
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 236

His Xaa Xaa Pro Cys Pro Xaa Gly Xaa Phe Xaa Cys Pro Xaa Asn Arg
 1               5                  10                  15
```

Xaa Gly Cys

<210> SEQ ID NO 237
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is C5g
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 237

His Xaa Xaa Thr Cys Pro Xaa Gly Xaa Phe Xaa Cys Pro Xaa Asn Arg
1               5                   10                  15

Xaa Gly Cys

<210> SEQ ID NO 238
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (3)..(3)
<223> OTHER INFORMATION: Xaa is C5g
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)

```
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 238

His Xaa Xaa Thr Cys Pro Xaa Gly Xaa Phe Xaa Cys Pro Xaa Asn Xaa
1               5                   10                  15

Pro Xaa Cys

<210> SEQ ID NO 239
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp

<400> SEQUENCE: 239

Ala Xaa Asp Val Thr Cys Pro Trp Gly Pro Phe Trp Cys Pro Val Asn
1               5                   10                  15

Arg Pro Gly Cys
            20

<210> SEQ ID NO 240
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (8)..(8)
<223> OTHER INFORMATION: Xaa is 1Nal

<400> SEQUENCE: 240

Ala Xaa Asp Val Thr Cys Pro Xaa Gly Pro Phe Trp Cys Pro Val Asn
1               5                   10                  15

Arg Pro Gly Cys
            20

<210> SEQ ID NO 241
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (12)..(12)
<223> OTHER INFORMATION: Xaa is 1Nal

<400> SEQUENCE: 241
```

```
Ala Xaa Asp Val Thr Cys Pro Xaa Gly Pro Phe Xaa Cys Pro Val Asn
1               5                   10                  15

Arg Pro Gly Cys
            20
```

<210> SEQ ID NO 242
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (8)..(8)
<223> OTHER INFORMATION: Xaa is 1Nal
<220> FEATURE:
<221> NAME/KEY: Xaa
<222> LOCATION: (10)..(10)
<223> OTHER INFORMATION: Xaa is Aib
<220> FEATURE:
<221> NAME/KEY: Xaa
<222> LOCATION: (15)..(15)
<223> OTHER INFORMATION: Xaa is tBuGly
<220> FEATURE:
<221> NAME/KEY: Xaa
<222> LOCATION: (17)..(17)
<223> OTHER INFORMATION: Xaa is HArg

<400> SEQUENCE: 242

```
Ala Xaa Asp Val Thr Cys Pro Xaa Gly Xaa Phe Trp Cys Pro Xaa Asn
1               5                   10                  15

Xaa Pro Gly Cys
            20
```

<210> SEQ ID NO 243
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib

<400> SEQUENCE: 243

```
His Xaa Val Thr Cys Pro Xaa Gly Xaa Phe Xaa Cys Pro Xaa Asn Arg
1               5                   10                  15
```

Xaa Gly Cys

<210> SEQ ID NO 244
<211> LENGTH: 16
<212> TYPE: PRT
<213> ORGANISM: Artificial
<220> FEATURE:
<223> OTHER INFORMATION: Synthetic peptide

<400> SEQUENCE: 244

Ala Cys Ala Trp Gly Pro Phe Trp Cys Pro Val Asn Arg Pro Gly Cys
1               5                   10                  15

<210> SEQ ID NO 245
<211> LENGTH: 16
<212> TYPE: PRT
<213> ORGANISM: Artificial
<220> FEATURE:
<223> OTHER INFORMATION: Synthetic peptide

<400> SEQUENCE: 245

Ala Cys Pro Ala Gly Pro Phe Trp Cys Pro Val Asn Arg Pro Gly Cys
1               5                   10                  15

<210> SEQ ID NO 246
<211> LENGTH: 16
<212> TYPE: PRT
<213> ORGANISM: Artificial
<220> FEATURE:
<223> OTHER INFORMATION: Synthetic peptide

<400> SEQUENCE: 246

Ala Cys Pro Trp Ala Pro Phe Trp Cys Pro Val Asn Arg Pro Gly Cys
1               5                   10                  15

<210> SEQ ID NO 247
<211> LENGTH: 16
<212> TYPE: PRT
<213> ORGANISM: Artificial
<220> FEATURE:
<223> OTHER INFORMATION: Synthetic peptide

<400> SEQUENCE: 247

Ala Cys Pro Trp Gly Ala Phe Trp Cys Pro Val Asn Arg Pro Gly Cys
1               5                   10                  15

<210> SEQ ID NO 248
<211> LENGTH: 16
<212> TYPE: PRT
<213> ORGANISM: Artificial
<220> FEATURE:
<223> OTHER INFORMATION: Synthetic peptide

<400> SEQUENCE: 248

Ala Cys Pro Trp Gly Pro Phe Ala Cys Pro Val Asn Arg Pro Gly Cys
1               5                   10                  15

<210> SEQ ID NO 249
<211> LENGTH: 16
<212> TYPE: PRT
<213> ORGANISM: Artificial
<220> FEATURE:
<223> OTHER INFORMATION: Synthetic peptide

<400> SEQUENCE: 249

Ala Cys Pro Trp Gly Pro Phe Trp Cys Ala Val Asn Arg Pro Gly Cys
1               5                   10                  15

<210> SEQ ID NO 250
<211> LENGTH: 16
<212> TYPE: PRT
<213> ORGANISM: Artificial
<220> FEATURE:
<223> OTHER INFORMATION: Synthetic peptide

<400> SEQUENCE: 250

Ala Cys Pro Trp Gly Pro Phe Trp Cys Pro Ala Asn Arg Pro Gly Cys
1               5                   10                  15

<210> SEQ ID NO 251
<211> LENGTH: 16
<212> TYPE: PRT
<213> ORGANISM: Artificial
<220> FEATURE:
<223> OTHER INFORMATION: Synthetic peptide

<400> SEQUENCE: 251

Ala Cys Pro Trp Gly Pro Phe Trp Cys Pro Val Asn Ala Pro Gly Cys
1               5                   10                  15

<210> SEQ ID NO 252
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is D-Ala

<400> SEQUENCE: 252

Ala Cys Xaa Trp Gly Pro Phe Trp Cys Pro Val Asn Arg Pro Gly Cys
1               5                   10                  15

<210> SEQ ID NO 253
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is D-Ala

<400> SEQUENCE: 253

Ala Cys Pro Xaa Gly Pro Phe Trp Cys Pro Val Asn Arg Pro Gly Cys
1               5                   10                  15

<210> SEQ ID NO 254
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is D-Ala

<400> SEQUENCE: 254

Ala Cys Pro Trp Xaa Pro Phe Trp Cys Pro Val Asn Arg Pro Gly Cys
1               5                   10                  15

```
<210> SEQ ID NO 255
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is D-Ala

<400> SEQUENCE: 255

Ala Cys Pro Trp Gly Xaa Phe Trp Cys Pro Val Asn Arg Pro Gly Cys
1               5                  10                  15

<210> SEQ ID NO 256
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is D-Ala

<400> SEQUENCE: 256

Ala Cys Pro Trp Gly Pro Xaa Trp Cys Pro Val Asn Arg Pro Gly Cys
1               5                  10                  15

<210> SEQ ID NO 257
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (8)..(8)
<223> OTHER INFORMATION: Xaa is D-Ala

<400> SEQUENCE: 257

Ala Cys Pro Trp Gly Pro Phe Xaa Cys Pro Val Asn Arg Pro Gly Cys
1               5                  10                  15

<210> SEQ ID NO 258
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (10)..(10)
<223> OTHER INFORMATION: Xaa is D-Ala

<400> SEQUENCE: 258

Ala Cys Pro Trp Gly Pro Phe Trp Cys Xaa Val Asn Arg Pro Gly Cys
1               5                  10                  15

<210> SEQ ID NO 259
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (11)..(11)
<223> OTHER INFORMATION: Xaa is D-Ala
```

-continued

<400> SEQUENCE: 259

Ala Cys Pro Trp Gly Pro Phe Trp Cys Pro Xaa Asn Arg Pro Gly Cys
1               5                   10                  15

<210> SEQ ID NO 260
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (13)..(13)
<223> OTHER INFORMATION: Xaa is D-Ala

<400> SEQUENCE: 260

Ala Cys Pro Trp Gly Pro Phe Trp Cys Pro Val Asn Xaa Pro Gly Cys
1               5                   10                  15

<210> SEQ ID NO 261
<211> LENGTH: 16
<212> TYPE: PRT
<213> ORGANISM: Artificial
<220> FEATURE:
<223> OTHER INFORMATION: Synthetic peptide

<400> SEQUENCE: 261

Ala Cys Pro Trp Ala Pro Phe Trp Cys Ala Val Asn Arg Pro Gly Cys
1               5                   10                  15

<210> SEQ ID NO 262
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (17)..(17)
<223> OTHER INFORMATION: Xaa is Aib
<220> FEATURE:
<221> NAME/KEY: Xaa
<222> LOCATION: (18)..(18)
<223> OTHER INFORMATION: Xaa is D-Asp

<400> SEQUENCE: 262

His Xaa Val Pro Cys Pro Xaa Ala Xaa Phe Xaa Cys Ala Xaa Asn Arg
1               5                   10                  15

Xaa Xaa Cys